(12) United States Patent
Khuu et al.

(10) Patent No.: US 11,040,174 B2
(45) Date of Patent: Jun. 22, 2021

(54) MULTI-DIRECTION STEERABLE HANDLES FOR STEERING CATHETERS

(71) Applicant: Edwards Lifesciences Corporation, Irvine, CA (US)

(72) Inventors: Bao Khuu, Irvine, CA (US); Matthew T. Winston, Aliso Viejo, CA (US); Asher L. Metchik, Rolling Hills Estates, CA (US); Eric Robert Dixon, Villa Park, CA (US); Sergio Delgado, Irvine, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 801 days.

(21) Appl. No.: 15/813,510

(22) Filed: Nov. 15, 2017

(65) Prior Publication Data
US 2019/0083748 A1 Mar. 21, 2019

Related U.S. Application Data

(60) Provisional application No. 62/560,576, filed on Sep. 19, 2017.

(51) Int. Cl.
*A61M 25/01* (2006.01)
*A61B 1/005* (2006.01)
*A61B 17/00* (2006.01)

(52) U.S. Cl.
CPC ....... *A61M 25/0136* (2013.01); *A61B 1/0052* (2013.01); *A61B 1/0057* (2013.01);
(Continued)

(58) Field of Classification Search
CPC .......... A61M 25/0136; A61M 25/0147; A61M 25/0138; A61M 25/0141; A61M 25/0144;
(Continued)

(56) References Cited

U.S. PATENT DOCUMENTS 3,874,388 A 4/1975 King et al.
4,340,091 A 7/1982 Skelton et al.
(Continued)

FOREIGN PATENT DOCUMENTS

CN 1142351 A 2/1997
CN 103565518 B 9/2015
(Continued)

OTHER PUBLICATIONS

Int'l. Search Report for PCT/US17/23034, Completed May 23, 2017.
(Continued)

*Primary Examiner* — Nathan R Price
*Assistant Examiner* — John A Doubrava
(74) *Attorney, Agent, or Firm* — Thomas C. Richardson

(57) ABSTRACT

Disclosed herein are steerable catheter assemblies and methods of steering catheters. Some embodiments include a catheter with first and second oppositely disposed pull wires and third and fourth oppositely disposed pull wires that flex the catheter, a control handle coupled to the catheter, a first follower connected to the first pull wire, a second follower connected to the second pull wire, a first driver coupled to the control handle and coupled to the first and second followers, a third follower connected to the third pull wire, a fourth follower connected to the fourth pull wire, and a second driver coupled to the control handle and coupled to the third and fourth followers. Rotation of the first driver moves the first and second followers in opposite directions. Rotation of the second driver moves the third and fourth followers in opposite directions.

19 Claims, 49 Drawing Sheets

(52) U.S. Cl.
CPC ... *A61M 25/0147* (2013.01); *A61B 17/00234* (2013.01); *A61M 25/0138* (2013.01); *A61M 25/0141* (2013.01); *A61M 25/0144* (2013.01)

(58) Field of Classification Search
CPC . A61B 1/0052; A61B 1/0057; A61B 17/0057; A61B 17/00234
See application file for complete search history.

(56) References Cited

U.S. PATENT DOCUMENTS

| | | | |
|---|---|---|---|
| 4,506,669 | A | 3/1985 | Blake, III |
| 4,590,937 | A | 5/1986 | Deniega |
| 4,693,248 | A | 9/1987 | Failla |
| 4,803,983 | A | 2/1989 | Siegel |
| 5,125,895 | A | 6/1992 | Buchbinder et al. |
| 5,171,252 | A | 12/1992 | Friedland |
| 5,195,962 | A | 3/1993 | Martin et al. |
| 5,292,326 | A | 3/1994 | Green et al. |
| 5,327,905 | A | 7/1994 | Avitall |
| 5,363,861 | A | 11/1994 | Edwards et al. |
| 5,370,685 | A | 12/1994 | Stevens |
| 5,389,077 | A | 2/1995 | Melinyshyn et al. |
| 5,411,552 | A | 5/1995 | Andersen et al. |
| 5,450,860 | A | 9/1995 | O'Connor |
| 5,456,674 | A | 10/1995 | Bos et al. |
| 5,465,716 | A | 11/1995 | Avitall |
| 5,474,057 | A | 12/1995 | Makower et al. |
| 5,478,353 | A | 12/1995 | Yoon |
| 5,487,746 | A | 1/1996 | Yu et al. |
| 5,565,004 | A | 10/1996 | Christoudias |
| 5,607,462 | A | 3/1997 | Imran |
| 5,609,598 | A | 3/1997 | Laufer et al. |
| 5,611,794 | A | 3/1997 | Sauer et al. |
| 5,626,607 | A | 5/1997 | Malecki et al. |
| 5,666,970 | A | 9/1997 | Smith |
| 5,695,504 | A | 12/1997 | Gifford, III et al. |
| 5,716,417 | A | 2/1998 | Girard et al. |
| 5,727,569 | A | 3/1998 | Benetti et al. |
| 5,741,297 | A | 4/1998 | Simon |
| 5,782,746 | A | 7/1998 | Wright |
| 5,797,960 | A | 8/1998 | Stevens et al. |
| 5,836,311 | A | 11/1998 | Borst et al. |
| 5,843,076 | A | 12/1998 | Webster, Jr. et al. |
| 5,855,590 | A | 1/1999 | Malecki et al. |
| 5,885,271 | A | 3/1999 | Hamilton et al. |
| 5,888,247 | A | 3/1999 | Benetti |
| 5,891,017 | A | 4/1999 | Swindle et al. |
| 5,891,088 | A * | 4/1999 | Thompson ........ A61M 25/0136 604/524 |
| 5,891,112 | A | 4/1999 | Samson |
| 5,894,843 | A | 4/1999 | Benetti et al. |
| 5,921,979 | A | 7/1999 | Kovac et al. |
| 5,944,738 | A | 8/1999 | Amplatz et al. |
| 5,957,835 | A | 9/1999 | Anderson et al. |
| 5,972,020 | A | 10/1999 | Carpentier et al. |
| 5,980,534 | A | 11/1999 | Gimpelson |
| 6,004,329 | A | 12/1999 | Myers et al. |
| 6,010,531 | A | 1/2000 | Donlon et al. |
| 6,017,358 | A | 1/2000 | Yoon et al. |
| 6,086,600 | A | 7/2000 | Kortenbach |
| 6,120,496 | A | 9/2000 | Whayne et al. |
| 6,132,370 | A | 10/2000 | Furnish et al. |
| 6,146,355 | A | 11/2000 | Biggs |
| 6,162,239 | A | 12/2000 | Manhes |
| 6,165,183 | A | 12/2000 | Kuehn et al. |
| 6,182,664 | B1 | 2/2001 | Cosgrove |
| 6,193,732 | B1 | 2/2001 | Frantzen et al. |
| 6,193,734 | B1 | 2/2001 | Bolduc et al. |
| 6,200,315 | B1 | 3/2001 | Gaiser et al. |
| 6,228,032 | B1 * | 5/2001 | Eaton ................ A61B 1/0052 600/463 |
| 6,241,743 | B1 | 6/2001 | Levin et al. |
| 6,269,819 | B1 | 8/2001 | Oz et al. |
| 6,269,829 | B1 | 8/2001 | Chen et al. |
| 6,312,447 | B1 | 11/2001 | Grimes |
| 6,461,366 | B1 | 10/2002 | Seguin |
| 6,468,285 | B1 | 10/2002 | Hsu et al. |
| 6,508,806 | B1 | 1/2003 | Hoste |
| 6,508,825 | B1 | 1/2003 | Selmon et al. |
| 6,530,933 | B1 | 3/2003 | Yeung et al. |
| 6,537,290 | B2 | 3/2003 | Adams et al. |
| 6,544,215 | B1 | 4/2003 | Bencini et al. |
| 6,626,930 | B1 | 9/2003 | Allen et al. |
| 6,629,534 | B1 | 10/2003 | St. Goar et al. |
| 6,719,767 | B1 | 4/2004 | Kimblad |
| 6,764,510 | B2 | 7/2004 | Vidlund et al. |
| 6,770,083 | B2 | 8/2004 | Seguin |
| 6,837,867 | B2 | 1/2005 | Kortelling |
| 6,855,137 | B2 | 2/2005 | Bon |
| 6,913,614 | B2 | 7/2005 | Marino et al. |
| 6,939,337 | B2 | 9/2005 | Parker et al. |
| 6,945,956 | B2 | 9/2005 | Waldhauser et al. |
| 7,048,754 | B2 | 5/2006 | Martin et al. |
| 7,101,395 | B2 | 9/2006 | Tremulis et al. |
| 7,125,421 | B2 | 10/2006 | Tremulis et al. |
| 7,288,097 | B2 | 10/2007 | Seguin |
| 7,371,210 | B2 | 5/2008 | Brock et al. |
| 7,464,712 | B2 | 12/2008 | Oz et al. |
| 7,509,959 | B2 | 3/2009 | Oz et al. |
| 7,569,062 | B1 | 8/2009 | Kuehn et al. |
| 7,682,369 | B2 | 3/2010 | Seguin |
| 7,731,706 | B2 | 6/2010 | Potter |
| 7,744,609 | B2 | 6/2010 | Allen et al. |
| 7,748,389 | B2 | 7/2010 | Salahieh et al. |
| 7,753,932 | B2 | 7/2010 | Gingrich et al. |
| 7,758,596 | B2 | 7/2010 | Oz et al. |
| 7,780,723 | B2 | 8/2010 | Taylor |
| 7,803,185 | B2 | 9/2010 | Gabbay |
| 7,824,443 | B2 | 11/2010 | Salahieh et al. |
| 7,981,123 | B2 | 7/2011 | Seguin |
| 7,988,724 | B2 | 8/2011 | Salahieh et al. |
| 8,048,024 | B2 | 11/2011 | Tah et al. |
| 8,052,750 | B2 | 11/2011 | Tuval et al. |
| 8,070,805 | B2 | 12/2011 | Vidlund et al. |
| 8,096,985 | B2 | 1/2012 | Legaspi et al. |
| 8,104,149 | B1 | 1/2012 | McGarity |
| 8,133,239 | B2 | 3/2012 | Oz et al. |
| 8,147,542 | B2 | 4/2012 | Maisano et al. |
| 8,172,856 | B2 | 5/2012 | Eigler et al. |
| 8,206,437 | B2 | 6/2012 | Bonhoeffer et al. |
| 8,216,301 | B2 | 7/2012 | Bonhoeffer et al. |
| 8,303,653 | B2 | 11/2012 | Bonhoeffer et al. |
| 8,313,525 | B2 | 11/2012 | Tuval et al. |
| 8,348,995 | B2 | 1/2013 | Tuval et al. |
| 8,348,996 | B2 | 1/2013 | Tuval et al. |
| 8,414,643 | B2 | 4/2013 | Tuval et al. |
| 8,425,404 | B2 | 4/2013 | Wilson et al. |
| 8,449,599 | B2 | 5/2013 | Chau et al. |
| 8,449,606 | B2 | 5/2013 | Eliasen et al. |
| 8,460,368 | B2 | 6/2013 | Taylor et al. |
| 8,470,028 | B2 | 6/2013 | Thornton et al. |
| 8,480,730 | B2 | 7/2013 | Maurer et al. |
| 8,540,767 | B2 | 9/2013 | Zhang |
| 8,579,965 | B2 | 11/2013 | Bonhoeffer et al. |
| 8,585,756 | B2 | 11/2013 | Bonhoeffer et al. |
| 8,617,087 | B2 | 12/2013 | Schultz |
| 8,641,604 | B2 | 2/2014 | Golden et al. |
| 8,652,202 | B2 | 2/2014 | Alon et al. |
| 8,668,733 | B2 | 3/2014 | Haug et al. |
| 8,676,290 | B2 | 3/2014 | Tegg |
| 8,721,665 | B2 | 5/2014 | Oz et al. |
| 8,740,918 | B2 | 6/2014 | Seguin |
| 8,771,347 | B2 | 7/2014 | DeBoer et al. |
| 8,778,017 | B2 | 7/2014 | Eliasen et al. |
| 8,834,357 | B2 | 9/2014 | Oskin et al. |
| 8,834,564 | B2 | 9/2014 | Tuval et al. |
| 8,840,560 | B2 | 9/2014 | Hossack et al. |
| 8,840,663 | B2 | 9/2014 | Salahieh et al. |
| 8,876,894 | B2 | 11/2014 | Tuval et al. |
| 8,876,895 | B2 | 11/2014 | Tuval et al. |
| 8,945,177 | B2 | 2/2015 | Dell et al. |
| 9,033,916 | B2 | 5/2015 | Schultz |
| 9,034,032 | B2 | 5/2015 | McLean et al. |

(56) References Cited

U.S. PATENT DOCUMENTS

| | | |
|---|---|---|
| 9,162,036 B2 | 10/2015 | Caples et al. |
| 9,198,757 B2 | 12/2015 | Schroeder et al. |
| 9,220,507 B1 | 12/2015 | Patel et al. |
| 9,259,317 B2 | 2/2016 | Wilson et al. |
| 9,282,972 B1 | 3/2016 | Patel et al. |
| 9,301,834 B2 | 4/2016 | Tuval et al. |
| 9,308,360 B2 | 4/2016 | Bishop et al. |
| 9,387,071 B2 | 7/2016 | Tuval et al. |
| 9,427,327 B2 | 8/2016 | Parrish |
| 9,439,763 B2 | 9/2016 | Geist et al. |
| 9,510,837 B2 | 12/2016 | Seguin |
| 9,510,946 B2 | 12/2016 | Chau et al. |
| 9,572,660 B2 | 2/2017 | Braido et al. |
| 9,642,704 B2 | 5/2017 | Tuval et al. |
| 9,700,445 B2 | 7/2017 | Martin et al. |
| 9,775,963 B2 | 10/2017 | Miller |
| D809,139 S | 1/2018 | Marsot et al. |
| 9,889,002 B2 | 2/2018 | Bonhoeffer et al. |
| 9,949,824 B2 | 4/2018 | Bonhoeffer et al. |
| 10,076,327 B2 | 9/2018 | Ellis et al. |
| 10,076,415 B1 | 9/2018 | Metchik et al. |
| 10,105,221 B2 | 10/2018 | Siegel |
| 10,105,222 B1 | 10/2018 | Metchik et al. |
| 10,111,751 B1 | 10/2018 | Metchik et al. |
| 10,123,873 B1 | 11/2018 | Metchik et al. |
| 10,130,475 B1 | 11/2018 | Metchik et al. |
| 10,136,993 B1 | 11/2018 | Metchik et al. |
| 10,159,570 B1 | 12/2018 | Metchik et al. |
| 10,226,309 B2 | 3/2019 | Ho et al. |
| 10,231,837 B1 | 3/2019 | Metchik et al. |
| 10,238,493 B1 | 3/2019 | Metchik et al. |
| 10,238,494 B2 | 3/2019 | McNiven et al. |
| 10,238,495 B2 | 3/2019 | Marsot et al. |
| 10,299,924 B2 | 5/2019 | Kizuka |
| 10,376,673 B2 | 8/2019 | Van Hoven et al. |
| 2001/0005787 A1 | 6/2001 | Oz et al. |
| 2002/0013571 A1 | 1/2002 | Goldfarb et al. |
| 2002/0107531 A1 | 8/2002 | Schreck et al. |
| 2002/0173811 A1 | 11/2002 | Tu et al. |
| 2002/0183787 A1 | 12/2002 | Wahr et al. |
| 2003/0144573 A1 | 7/2003 | Heilman et al. |
| 2003/0187467 A1 | 10/2003 | Schreck |
| 2003/0208231 A1 | 11/2003 | Williamson et al. |
| 2004/0003819 A1 | 1/2004 | St. Goar et al. |
| 2004/0034365 A1 | 2/2004 | Lentz et al. |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0127981 A1 | 7/2004 | Rahdert et al. |
| 2004/0127982 A1 | 7/2004 | Machold et al. |
| 2004/0147943 A1 | 7/2004 | Kobayashi |
| 2004/0181206 A1 | 9/2004 | Chiu et al. |
| 2004/0181238 A1 | 9/2004 | Zarbatany et al. |
| 2004/0210307 A1 | 10/2004 | Khairkhahan |
| 2004/0220593 A1 | 11/2004 | Greenhalgh |
| 2005/0010287 A1 | 1/2005 | Macoviak et al. |
| 2005/0049618 A1 | 3/2005 | Masuda et al. |
| 2005/0137690 A1 | 6/2005 | Salahieh et al. |
| 2005/0143767 A1 | 6/2005 | Kimura et al. |
| 2005/0165429 A1 | 7/2005 | Douglas et al. |
| 2005/0216039 A1 | 9/2005 | Lederman |
| 2005/0251183 A1 | 11/2005 | Buckman et al. |
| 2005/0288786 A1 | 12/2005 | Chanduszko |
| 2006/0020275 A1 | 1/2006 | Goldfarb et al. |
| 2006/0089671 A1 | 4/2006 | Goldfarb et al. |
| 2006/0100649 A1 | 5/2006 | Hart |
| 2006/0122647 A1 | 6/2006 | Callaghan et al. |
| 2006/0142694 A1 | 6/2006 | Bednarek et al. |
| 2006/0178700 A1 | 8/2006 | Quinn |
| 2006/0224169 A1 | 10/2006 | Weisenburgh et al. |
| 2007/0010800 A1 | 1/2007 | Weitzner et al. |
| 2007/0010877 A1 | 1/2007 | Salahieh et al. |
| 2007/0016286 A1 | 1/2007 | Herrmann et al. |
| 2007/0021779 A1 | 1/2007 | Garvin et al. |
| 2007/0032807 A1 | 2/2007 | Ortiz et al. |
| 2007/0093857 A1 | 4/2007 | Rogers et al. |
| 2007/0093890 A1 | 4/2007 | Eliasen et al. |
| 2007/0156197 A1 | 7/2007 | Root et al. |
| 2007/0191154 A1 | 8/2007 | Genereux et al. |
| 2007/0197858 A1 | 8/2007 | Goldfarb et al. |
| 2007/0198038 A1 | 8/2007 | Cohen et al. |
| 2007/0265700 A1 | 11/2007 | Eliasen et al. |
| 2007/0282414 A1 | 12/2007 | Soltis et al. |
| 2007/0293943 A1 | 12/2007 | Quinn |
| 2007/0299387 A1 | 12/2007 | Williams et al. |
| 2007/0299424 A1 | 12/2007 | Cumming et al. |
| 2008/0009882 A1 | 1/2008 | Drysen |
| 2008/0039743 A1 | 2/2008 | Fox et al. |
| 2008/0039953 A1 | 2/2008 | Davis et al. |
| 2008/0065149 A1 | 3/2008 | Thielen et al. |
| 2008/0077144 A1 | 3/2008 | Crofford |
| 2008/0091169 A1 | 4/2008 | Heideman et al. |
| 2008/0140089 A1 | 6/2008 | Kogiso et al. |
| 2008/0147093 A1 | 6/2008 | Roskopf et al. |
| 2008/0147112 A1 | 6/2008 | Sheets et al. |
| 2008/0167713 A1 | 7/2008 | Bolling |
| 2008/0177300 A1 | 7/2008 | Mas et al. |
| 2008/0208332 A1 | 8/2008 | Lamphere et al. |
| 2008/0221672 A1 | 9/2008 | Lamphere et al. |
| 2008/0255427 A1 | 10/2008 | Satake et al. |
| 2008/0281411 A1 | 11/2008 | Berreklouw |
| 2008/0287862 A1 | 11/2008 | Weitzner et al. |
| 2008/0294247 A1 | 11/2008 | Yang et al. |
| 2008/0312506 A1 | 12/2008 | Spivey et al. |
| 2008/0319455 A1 | 12/2008 | Harris et al. |
| 2009/0005863 A1 | 1/2009 | Goetz et al. |
| 2009/0024110 A1 | 1/2009 | Heideman et al. |
| 2009/0131880 A1 | 5/2009 | Speziali et al. |
| 2009/0156995 A1 | 6/2009 | Martin et al. |
| 2009/0163934 A1 | 6/2009 | Raschdorf, Jr. et al. |
| 2009/0166913 A1 | 7/2009 | Guo et al. |
| 2009/0177266 A1 | 7/2009 | Powell et al. |
| 2009/0275902 A1 | 11/2009 | Heeps et al. |
| 2009/0287304 A1 | 11/2009 | Dahlgren et al. |
| 2010/0022823 A1 | 1/2010 | Goldfarb et al. |
| 2010/0057192 A1 | 3/2010 | Celermajer |
| 2010/0069834 A1 | 3/2010 | Schultz |
| 2010/0094317 A1 | 4/2010 | Goldfarb et al. |
| 2010/0106141 A1 | 4/2010 | Osypka et al. |
| 2010/0121434 A1 | 5/2010 | Paul et al. |
| 2010/0249497 A1 | 9/2010 | Peine et al. |
| 2010/0298929 A1 | 11/2010 | Thornton et al. |
| 2010/0324595 A1 | 12/2010 | Linder et al. |
| 2011/0082538 A1 | 4/2011 | Dahlgren et al. |
| 2011/0137410 A1 | 6/2011 | Hacohen |
| 2011/0168180 A1* | 7/2011 | Lugtigheid ......... A61M 16/208 128/205.14 |
| 2011/0245855 A1 | 10/2011 | Matsuoka et al. |
| 2011/0257723 A1 | 10/2011 | McNamara |
| 2011/0295281 A1 | 12/2011 | Mizumoto et al. |
| 2012/0022633 A1 | 1/2012 | Olson et al. |
| 2012/0089125 A1 | 4/2012 | Scheibe et al. |
| 2012/0109160 A1 | 5/2012 | Martinez et al. |
| 2012/0116419 A1 | 5/2012 | Sigmon, Jr. |
| 2012/0209318 A1 | 8/2012 | Qadeer |
| 2012/0277853 A1 | 11/2012 | Rothstein |
| 2013/0035759 A1 | 2/2013 | Gross et al. |
| 2013/0041314 A1 | 2/2013 | Dillon |
| 2013/0066341 A1 | 3/2013 | Ketai et al. |
| 2013/0066342 A1 | 3/2013 | Dell et al. |
| 2013/0072945 A1 | 3/2013 | Terada |
| 2013/0073034 A1 | 3/2013 | Wilson et al. |
| 2013/0110254 A1 | 5/2013 | Osborne |
| 2013/0190798 A1 | 7/2013 | Kapadia |
| 2013/0190861 A1 | 7/2013 | Chau et al. |
| 2013/0268069 A1 | 10/2013 | Zakai et al. |
| 2013/0282059 A1 | 10/2013 | Ketai et al. |
| 2013/0304197 A1 | 11/2013 | Buchbinder et al. |
| 2013/0325110 A1 | 12/2013 | Khalil et al. |
| 2014/0031928 A1 | 1/2014 | Murphy et al. |
| 2014/0046433 A1 | 2/2014 | Kovalsky |
| 2014/0046434 A1 | 2/2014 | Rolando et al. |
| 2014/0052237 A1 | 2/2014 | Lane et al. |
| 2014/0058411 A1 | 2/2014 | Soutorine et al. |

(56) References Cited

U.S. PATENT DOCUMENTS

| | | |
|---|---|---|
| 2014/0067048 A1 | 3/2014 | Chau et al. |
| 2014/0067052 A1 | 3/2014 | Chau et al. |
| 2014/0094903 A1 | 4/2014 | Miller et al. |
| 2014/0107571 A1 | 4/2014 | Golden et al. |
| 2014/0135685 A1 | 5/2014 | Kabe et al. |
| 2014/0194975 A1 | 7/2014 | Quill et al. |
| 2014/0200662 A1 | 7/2014 | Eftel et al. |
| 2014/0207231 A1 | 7/2014 | Hacohen et al. |
| 2014/0236198 A1 | 8/2014 | Goldfarb et al. |
| 2014/0243968 A1 | 8/2014 | Padala |
| 2014/0251042 A1 | 9/2014 | Asselin et al. |
| 2014/0260724 A1 | 9/2014 | Currier et al. |
| 2014/0277404 A1 | 9/2014 | Wilson et al. |
| 2014/0277411 A1 | 9/2014 | Bortlein et al. |
| 2014/0316428 A1 | 10/2014 | Golan |
| 2014/0324164 A1 | 10/2014 | Gross et al. |
| 2014/0330368 A1 | 11/2014 | Gloss et al. |
| 2014/0336751 A1 | 11/2014 | Kramer |
| 2014/0371843 A1 | 12/2014 | Wilson et al. |
| 2015/0039084 A1 | 2/2015 | Levi et al. |
| 2015/0057704 A1 | 2/2015 | Takahashi |
| 2015/0094802 A1 | 4/2015 | Buchbinder et al. |
| 2015/0100116 A1 | 4/2015 | Mohl et al. |
| 2015/0105808 A1 | 4/2015 | Gordon et al. |
| 2015/0148896 A1 | 5/2015 | Karapetian et al. |
| 2015/0157268 A1 | 6/2015 | Winshtein et al. |
| 2015/0196390 A1 | 7/2015 | Ma et al. |
| 2015/0223793 A1 | 8/2015 | Goldfarb et al. |
| 2015/0230919 A1 | 8/2015 | Chau et al. |
| 2015/0231366 A1 | 8/2015 | Davies et al. |
| 2015/0238313 A1 | 8/2015 | Spence et al. |
| 2015/0257757 A1 | 9/2015 | Powers et al. |
| 2015/0257877 A1 | 9/2015 | Hernandez |
| 2015/0257883 A1 | 9/2015 | Basude et al. |
| 2015/0313592 A1 | 11/2015 | Coillard-Lavirotte et al. |
| 2015/0351904 A1 | 12/2015 | Cooper et al. |
| 2015/0366666 A1 | 12/2015 | Khairkhahan et al. |
| 2016/0008131 A1 | 1/2016 | Christianson et al. |
| 2016/0022970 A1 | 1/2016 | Forcucci et al. |
| 2016/0106539 A1 | 4/2016 | Buchbinder et al. |
| 2016/0113762 A1 | 4/2016 | Clague et al. |
| 2016/0113764 A1 | 4/2016 | Sheahan et al. |
| 2016/0113766 A1 | 4/2016 | Ganesan et al. |
| 2016/0155987 A1 | 6/2016 | Yoo et al. |
| 2016/0174979 A1 | 6/2016 | Wei |
| 2016/0174981 A1 | 6/2016 | Fago et al. |
| 2016/0242906 A1 | 8/2016 | Morriss et al. |
| 2016/0287387 A1 | 10/2016 | Wei |
| 2016/0317290 A1 | 11/2016 | Chau et al. |
| 2016/0331523 A1 | 11/2016 | Chau et al. |
| 2016/0354082 A1 | 12/2016 | Oz et al. |
| 2017/0020521 A1 | 1/2017 | Krone et al. |
| 2017/0035561 A1 | 2/2017 | Rowe et al. |
| 2017/0035566 A1 | 2/2017 | Krone et al. |
| 2017/0042456 A1 | 2/2017 | Budiman |
| 2017/0042678 A1 | 2/2017 | Ganesan et al. |
| 2017/0049455 A1 | 2/2017 | Seguin |
| 2017/0100236 A1 | 4/2017 | Robertson et al. |
| 2017/0224955 A1 | 8/2017 | Douglas et al. |
| 2017/0239048 A1 | 8/2017 | Goldfarb et al. |
| 2017/0252154 A1 | 9/2017 | Tubishevitz et al. |
| 2017/0281330 A1 | 10/2017 | Liljegren et al. |
| 2017/0348102 A1 | 12/2017 | Cousins et al. |
| 2018/0008311 A1 | 1/2018 | Shiroff et al. |
| 2018/0021044 A1 | 1/2018 | Miller et al. |
| 2018/0021129 A1 | 1/2018 | Peterson et al. |
| 2018/0021134 A1 | 1/2018 | McNiven et al. |
| 2018/0078271 A1 | 3/2018 | Thrasher, III |
| 2018/0126124 A1 | 5/2018 | Winston et al. |
| 2018/0146964 A1 | 5/2018 | Garcia et al. |
| 2018/0146966 A1 | 5/2018 | Hernandez et al. |
| 2018/0153552 A1 | 6/2018 | King et al. |
| 2018/0161159 A1 | 6/2018 | Lee et al. |
| 2018/0168803 A1 | 6/2018 | Pesce et al. |
| 2018/0221147 A1 | 8/2018 | Ganesan et al. |
| 2018/0235657 A1 | 8/2018 | Abunassar |
| 2018/0243086 A1 | 8/2018 | Barbarino et al. |
| 2018/0258665 A1 | 9/2018 | Reddy et al. |
| 2018/0263767 A1 | 9/2018 | Chau et al. |
| 2018/0296326 A1 | 10/2018 | Dixon et al. |
| 2018/0296327 A1 | 10/2018 | Dixon et al. |
| 2018/0296328 A1 | 10/2018 | Dixon et al. |
| 2018/0296329 A1 | 10/2018 | Dixon et al. |
| 2018/0296330 A1 | 10/2018 | Dixon et al. |
| 2018/0296331 A1 | 10/2018 | Dixon et al. |
| 2018/0296332 A1 | 10/2018 | Dixon et al. |
| 2018/0296333 A1 | 10/2018 | Dixon et al. |
| 2018/0296334 A1 | 10/2018 | Dixon et al. |
| 2018/0325661 A1 | 11/2018 | Delgado et al. |
| 2018/0325671 A1 | 11/2018 | Abunassar et al. |
| 2018/0333259 A1 | 11/2018 | Dibie |
| 2018/0344457 A1 | 12/2018 | Gross et al. |
| 2018/0353181 A1 | 12/2018 | Wei |
| 2019/0000613 A1 | 1/2019 | Delgado et al. |
| 2019/0000623 A1 | 1/2019 | Pan et al. |
| 2019/0008642 A1 | 1/2019 | Delgado et al. |
| 2019/0008643 A1 | 1/2019 | Delgado et al. |
| 2019/0015199 A1 | 1/2019 | Delgado et al. |
| 2019/0015200 A1 | 1/2019 | Delgado et al. |
| 2019/0015207 A1 | 1/2019 | Delgado et al. |
| 2019/0015208 A1 | 1/2019 | Delgado et al. |
| 2019/0021851 A1 | 1/2019 | Delgado et al. |
| 2019/0021852 A1 | 1/2019 | Delgado et al. |
| 2019/0029498 A1 | 1/2019 | Mankowski et al. |
| 2019/0029810 A1 | 1/2019 | Delgado et al. |
| 2019/0029813 A1 | 1/2019 | Delgado et al. |
| 2019/0030285 A1 | 1/2019 | Prabhu et al. |
| 2019/0053810 A1 | 2/2019 | Griffin |
| 2019/0060058 A1 | 2/2019 | Delgado et al. |
| 2019/0060059 A1 | 2/2019 | Delgado et al. |
| 2019/0060072 A1 | 2/2019 | Zeng |
| 2019/0060073 A1 | 2/2019 | Delgado et al. |
| 2019/0060074 A1 | 2/2019 | Delgado et al. |
| 2019/0060075 A1 | 2/2019 | Delgado et al. |
| 2019/0069991 A1 | 3/2019 | Metchik et al. |
| 2019/0069992 A1 | 3/2019 | Delgado et al. |
| 2019/0069993 A1 | 3/2019 | Delgado et al. |
| 2019/0105156 A1 | 4/2019 | He et al. |
| 2019/0111239 A1 | 4/2019 | Bolduc et al. |
| 2019/0142589 A1 | 5/2019 | Basude |
| 2019/0159782 A1 | 5/2019 | Kamaraj et al. |
| 2019/0167197 A1 | 6/2019 | Abunassar et al. |
| 2019/0209323 A1 | 7/2019 | Metchik et al. |
| 2019/0261995 A1 | 8/2019 | Goldfarb et al. |
| 2019/0261996 A1 | 8/2019 | Goldfarb et al. |
| 2019/0261997 A1 | 8/2019 | Goldfarb et al. |
| 2019/0314155 A1 | 10/2019 | Franklin et al. |
| 2020/0113683 A1 | 4/2020 | Dale et al. |

FOREIGN PATENT DOCUMENTS

| | | |
|---|---|---|
| EP | 0098100 A2 | 1/1984 |
| FR | 2146050 A5 | 2/1973 |
| FR | 9711600 | 3/1997 |
| WO | 2017015632 A1 | 1/2017 |
| WO | 2017165229 A1 | 9/2017 |
| WO | 2018013856 A1 | 1/2018 |
| WO | 2018050200 A1 | 3/2018 |
| WO | 2018050203 A1 | 3/2018 |
| WO | 2018195015 A1 | 10/2018 |
| WO | 2018195201 A1 | 10/2018 |
| WO | 2018195215 A2 | 10/2018 |
| WO | 2019139904 A1 | 7/2019 |

OTHER PUBLICATIONS

Al Zaibag et al., "Percutaneous Balloon Valvotomy in Tricuspid Stenosis", British Heart Journal, vol. 57, No. 1, Jan. 1987.

Al-Khaja et al., "Eleven years' experience with Carpentier-Edwards biological valves in relation to survival and complications", European Journal of Cardio-Thoracic Surgery, vol. 3, No. 4, pp. 305-311, Jul. 1, 1989, Springer-Verlag, Berlin, Germany.

(56) References Cited

OTHER PUBLICATIONS

Almagor et al., "Balloon Expandable Stent Implantation in Stenotic Right Heart Valved Conduits", Journal of the American College of Cardiology, vol. 16, No. 5, pp. 1310-1314, Nov. 15, 1990.
Andersen, et al., "Transluminal implantation of artificial heart valves. Description of a new expandable aortic valve and initial results with implantation by catheter technique in closed chest pigs", European Heart Journal, vol. 13, No. 5, pp. 704-708, May 1, 1992, The European Society of Cardiology, Oxford University Press, United Kingdom.
Andersen, H.R. "History of Percutaneous Aortic Valve Prosthesis," Herz, vol. 34., No. 5, pp. 343-346, Aug. 2009, Urban & Vogel, Germany.
Batista RJ et al., "Partial left ventriculectomy to treat end-stage heart disease", Ann Thorac Surg., vol. 64, Issue—3, pp. 634-638, Sep. 1997.
Beall AC Jr. et al.,"Clinical experience with a dacron velour-covered teflon-disc mitral-valve prosthesis", Ann Thorac Surg., vol. 5, Issue 5, pp. 402-410, May 1968.
Benchimol et al., "Simultaneous left ventricular echocardiography and aortic blood velocity during rapid right ventricular pacing in man", The American Journal of the Medical Sciences, vol. 273, No. 1, pp. 55-62, Jan.-Feb. 1977; Elsevier, United States.
Dake et al., "Transluminal Placement of Endovascular Stent-Grafts for the Treatment of Descending Thoracic Aortic Aneurysms", The New England Journal of Medicine, vol. 331, No. 26, pp. 1729-1734, Dec. 29, 1994.
Dotter et al., "Transluminal Treatment of Arteriosclerotic Obstruction: Description of a New Technic and a Preliminary Report of Its Application", Circulation, vol. XXX, No. 30, pp. 654-670, Nov. 1, 1964, Lippincott Williams & Wilkins, Philadelphia, PA.
Fucci et al., "Improved results with mitral valve repair using new surgical techniques", Eur J Cardiothorac Surg. 1995;Issue 9, vol. 11, pp. 621-626.
Inoune et al., "Clinical application of transvenous mitral commissurotomy by a new balloon catheter," The Journal of Thoracic and Cardiovascular Surgery,vol. 87, No. 3, pp. 394-402, Mar. 1984, Elsevier, United States.
Kolata, Gina "Device That Opens Clogged Arteries Gets a Failing Grade in a New Study", The New York Times, Jan. 3, 1991, pp. 1-2 [online], [retrieved on Jul. 29, 2009]. Retrieved from the Internet <URL:http://www.nytimes.com/1991/01/03/health/device-that-opens-clogged-arteries-gets-a-faili . . . .
Lawrence, Jr., et al., "Percutaneous Endovascular Graft: Experimental Evaluation", Cardiovascular Radiology 163, pp. 357-360, May 1987.
Maisano F et al., 'The edge-to-edge technique: a simplified method to correct mitral insufficiency', Eur J Cardiothorac Surg., vol. 13, Issue—3, pp. 240-245, Mar. 1998.
Pavcnik et al. "Development and Initial Experimental Evaluation of a Prosthetic Aortic Valve for Transcatheter Placement," Radiology, vol. 183, No. 1, pp. 151-154, Apr. 1, 1992. Elsevier, United States.

Porstmann et al., "Der Verschluß des Ductus Arteriosus Persistens Ohne Thorakotomie", Thoraxchirurgie Vaskuläre Chirurgie, Band 15, Heft 2, Stuttgart, im Apr. 1967, pp. 199-203.
Praz et al., "Compassionate use of the PASCAL transcatheter mitral valve repair system for patients with severe mitral regurgitation: a multicentre, prospective, observational, first-in-man study," Lancet, vol. 390, pp. 773-780, Aug. 19, 2017, Lancet, United States.
Rashkind et al., "Creation of an Atrial Septal Defect Without Thoracotomy: A Pallative Approach to Complete Transposition of the Great Arteries", The Journal of the American Medical Association, vol. 196, No. 11, pp. 173-174, Jun. 13, 1956.
Rashkind et al., "Historical Aspects of Interventional Cardiology: Past, Present, and Future", vol. 13, No. 4, pp. 363-367, Dec. 1986, Texas Heart Institute Journal, Interventional Cardiology, Houston, TX.
Reul RM et al., "Mitral valve reconstruction for mitral insufficiency", Prog Cardiovasc Dis., vol. 39, Issue—6, May-Jun. 1997.
Rösch et al., "The Birth, Early Years and Future of Interventional Radiology," Journal of Vascular and Interventional Radiology, vol. 14, No. 7, pp. 841-853, Jul. 1, 2003, Elsevier, United States.
Sabbah et al., "Mechanical Factors in the Degeneration of Porcine Bioprosthetic Valves: An Overview", Journal of Cardiac Surgery, vol. 4, No. 4, pp. 302-309, Dec. 1989.
Selby et al., "Experience with New Retrieval Forceps for Foreign Body Removal in the Vascular, Urinary, and Biliary Systems", Radiology, vol. 176, No. 2, pp. 535-538, Jul. 31, 1990, Radiological Society of North America, Oak Brook, IL.
Serruys et al., "Stenting of coronary arteries. Are we the sorcerer's apprentice?", European Heart Journal, vol. 10, No. 9 pp. 774-782, Sep. 1, 1989, The European Society of Cardiology, Oxford University Press, United Kingdom.
Sigwart, Ulrich, "An Overview of Intravascular Stents: Old and New," Textbook of Interventional Cardiology, Second Edition, chapter 48, pp. 803-815, © 1994, W.B. Saunders Company, Philadelphia, PA.
Uchida et al., "Modifications of Gianturco Expandable Wire Stents", Technical Note, American Roentgen Ray Society, pp. 1185-1187, May 1988.
Umaña JP et al., "'Bow-tie' mitral valve repair: an adjuvant technique for ischemic mitral regurgitation', Ann Thorac Surg., vol. 66, Issue—6, pp. 1640-1646, Nov. 1998.
Urban, Philip MD, "Coronary Artery Stenting", pp. 5-47, © 1991, ISBN: 2-88049-054-5, Editions Medecine et Hygiene, Geneva, Switzerland.
Watt et al., "Intravenous adenosine in the treatment of supraventricular rachycardia: a dose-ranging study and interaction with dipyridamole", British Journal of Clinical Pharmacology, vol. 21, No. 2, pp. 227-230, Feb. 1986, British Pharmacological Society, London, United Kingdom.
Wheatley, David J., "Valve Prosthesis", Rob & Smith's Operative Surgery—Cardiac Surgery, vol. 91, No. 2, pp. 415-424, Feb. 1, 1987, Butterworth Scientific, London, UK.

\* cited by examiner

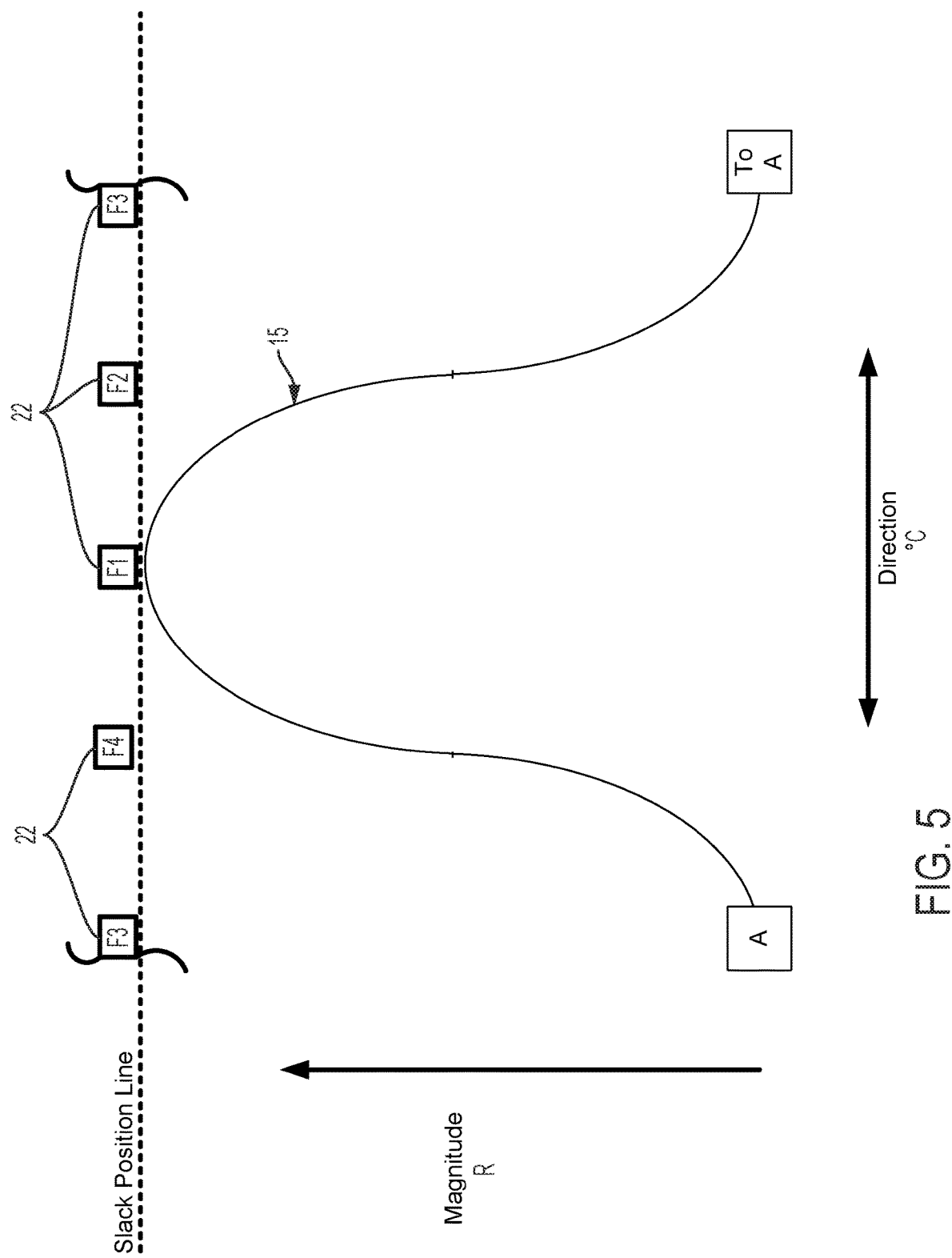

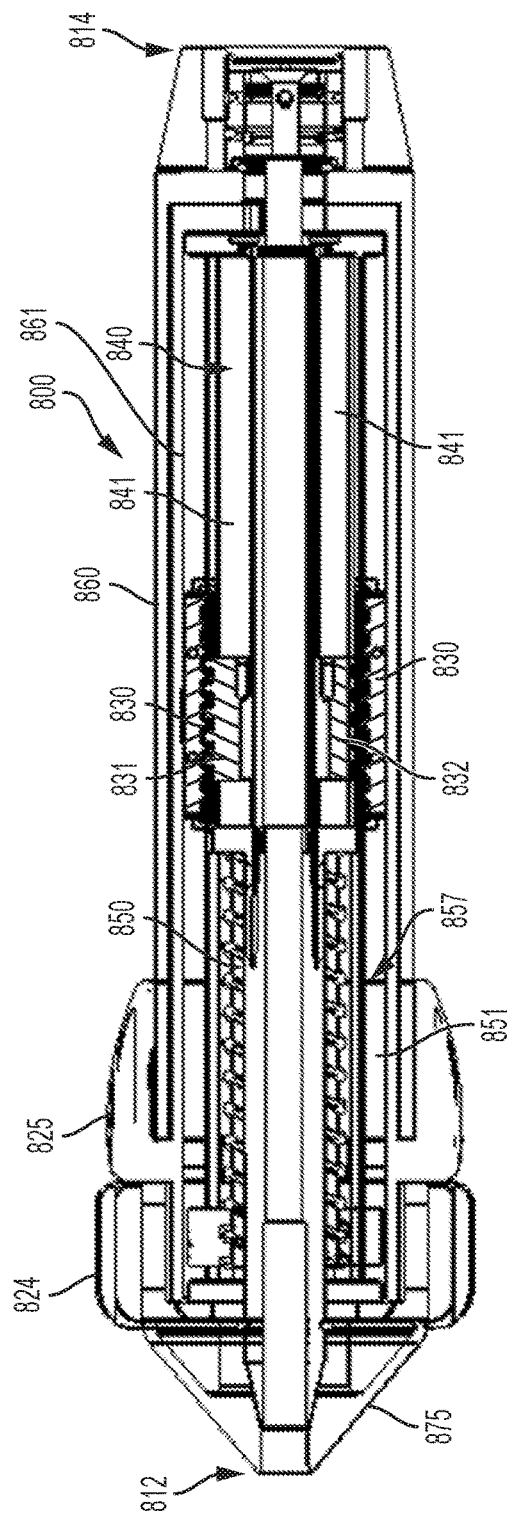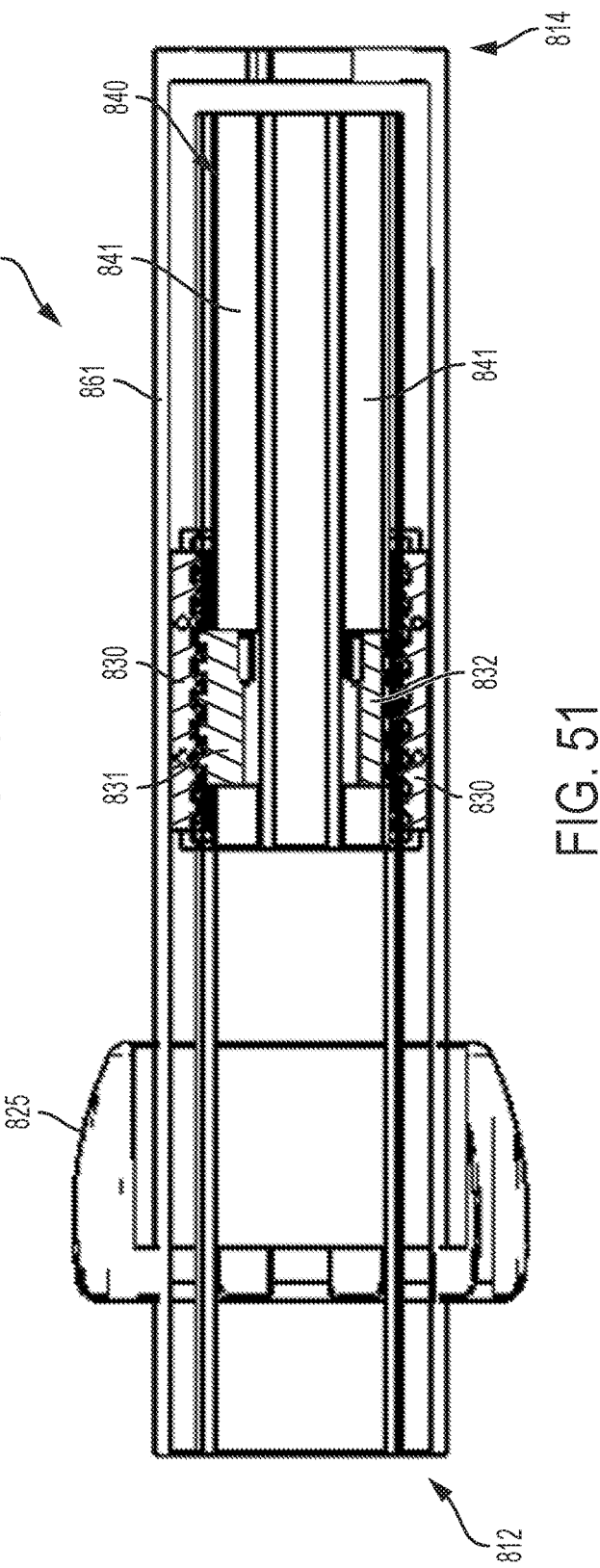

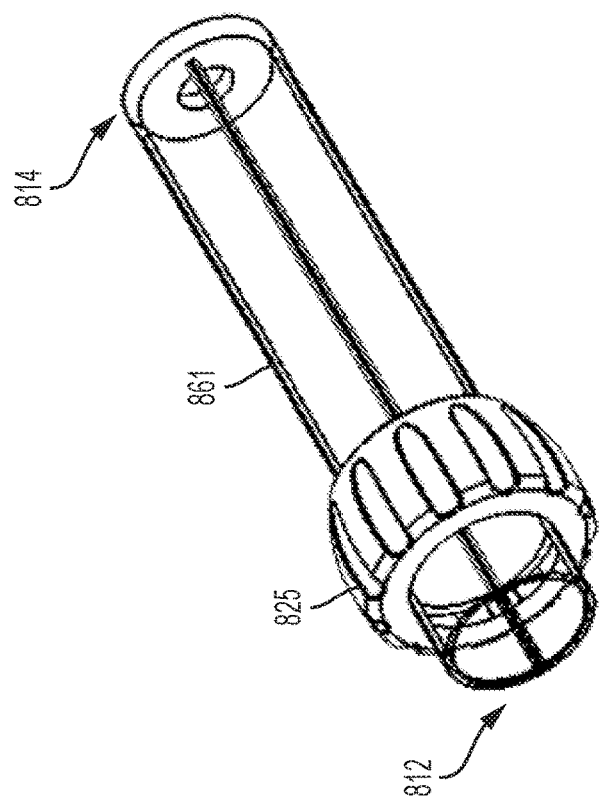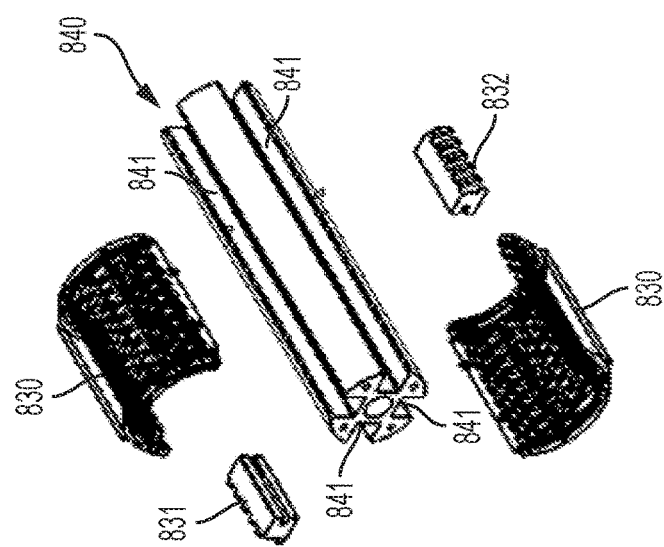
FIG. 52

MULTI-DIRECTION STEERABLE HANDLES FOR STEERING CATHETERS

RELATED APPLICATIONS

This application claims the benefit of U.S. Provisional Patent Application No. 62/560,576 filed Sep. 19, 2017, which is incorporated by reference herein in its entirety.

FIELD

The present disclosure concerns steerable catheter assemblies for steering an attached catheter or other transluminal device.

BACKGROUND

Transvascular techniques have been developed for introducing and implanting prosthetic devices, such as heart valves, into a patient's body using a flexible transvascular catheter in a manner that is less invasive than open heart surgery. Typical catheter control systems only allow for limited flexing of the distal end of the catheter, such as in two orthogonal axes perpendicular to the longitudinal axis of the catheter. For example, a conventional catheter control handle may include a lever or dial coupled to a pull wire running along one side of the catheter, such that actuating the lever or dial causes the distal tip of the catheter to flex radially to one side of the longitudinal axis. To cause the distal tip to flex in other directions, it is typically required to actuate additional levers/dials that are coupled to other pull wires. Thus, a plurality of actuation devices typically have to be actuated at the same time in careful combinations or sequences to generate a desired degree of radial flex in a desired circumferential direction. In this way catheter flex magnitude control and catheter flex direction control are integrated such that it can be difficult to control and not intuitive to understand.

SUMMARY

Disclosed herein are steerable catheter assemblies and methods for steering catheters. Some embodiments include a catheter with first and second oppositely disposed pull wires and third and fourth oppositely disposed pull wires that flex the catheter, a control handle coupled to the catheter, a first follower connected to the first pull wire, a second follower connected to the second pull wire, a first driver coupled to the control handle and coupled to the first and second followers, a third follower connected to the third pull wire, a fourth follower connected to the fourth pull wire, and a second driver coupled to the control handle and coupled to the third and fourth followers. Rotation of the first driver moves the first and second followers in opposite directions. Rotation of the second driver moves the third and fourth followers in opposite directions.

The first driver can comprise a first planetary gear that engages first and second drive screws, such that one adjustment of the first planetary gear turns the first and second drive screws, which can engage with the first and second followers, and the first and second followers move in opposite axial directions. The second driver comprises a second planetary gear that engages third and fourth drive screws, such that one adjustment of the second planetary gear turns the third and fourth drive screws, which can engage with the third and fourth followers, and the third and fourth followers move in opposite axial directions.

The application discloses methods of steering a catheter by rotating a first driver to move first and second followers in opposite directions, wherein the first and second followers are connected to first and second catheter flex wires, and rotating a second driver to move third and fourth followers in opposite directions, wherein the third and fourth followers are connected to third and fourth catheter flex wires. The first and second followers can be moved in opposite directions by first and second opposite handed screws that are rotated in the same direction. The third and fourth followers can be moved in opposite directions by third and fourth opposite handed screws that are rotated in the same direction.

The foregoing and other objects, features, and advantages of the disclosed technology will become more apparent from the following detailed description, which proceeds with reference to the accompanying figures.

BRIEF DESCRIPTION OF THE DRAWINGS

FIGS. 5-15 are graphical illustrations of various cam and cam follower arrangements, indicating catheter flex magnitude and direction as a function of cam and cam follower movements for different user inputs and cam shapes;

FIG. 50 shows a cut-away view of the multi-direction control handle of FIG. 47 taken along the plane indicated by lines 50-50 in FIG. 47;

FIG. 51 shows a cut-away view of the control handle of FIG. 50 with the driver components removed;

FIG. 52 shows an exploded view of the control handle of FIG. 50 with the driver component removed;

DETAILED DESCRIPTION

As used herein, the singular forms "a," "an," and "the" refer to one or more than one, unless the context clearly dictates otherwise.

As used herein, the term "includes" means "comprises." For example, a device that includes or comprises A and B contains A and B but can optionally contain C or other components other than A and B. A device that includes or comprises A or B can contain A or B or A and B, and optionally one or more other components such as C.

Figure 1:
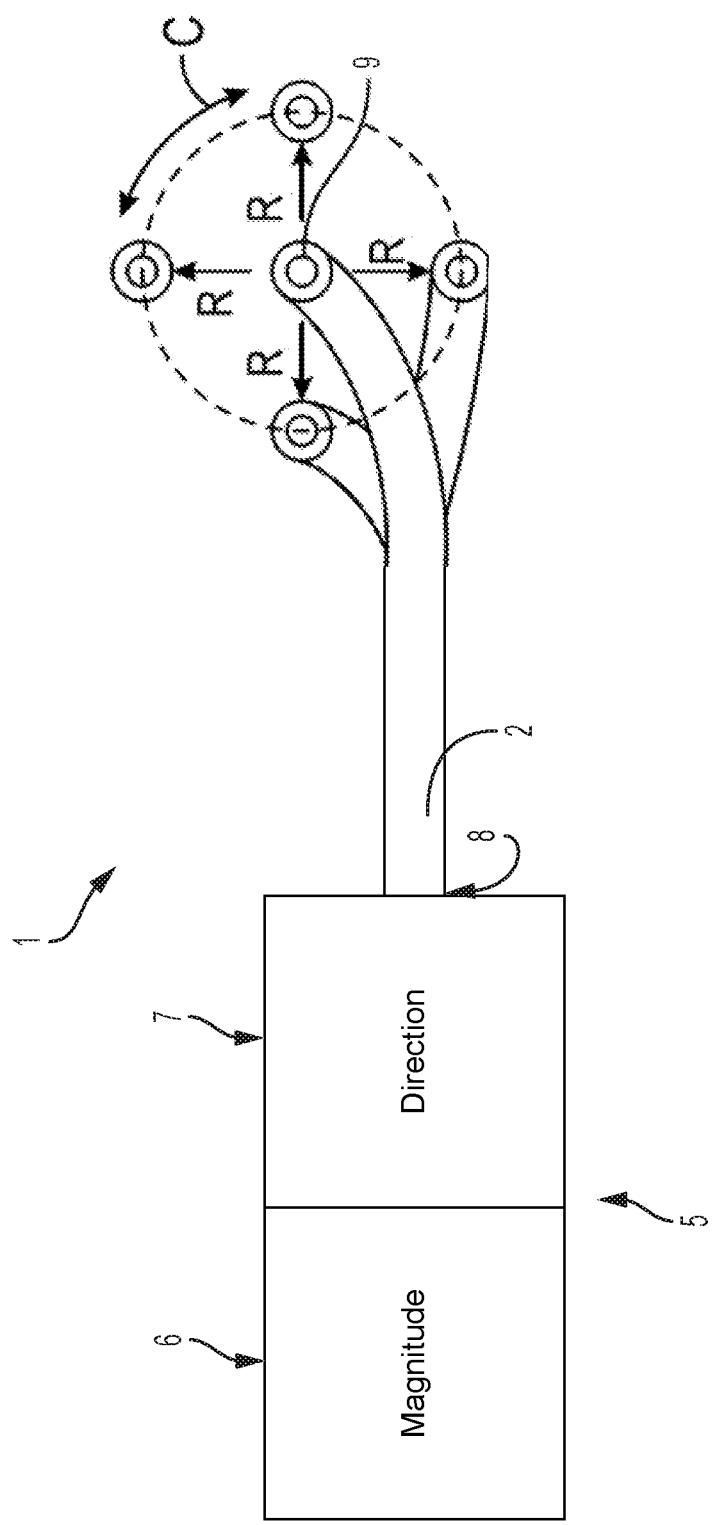
FIG. 1 is a schematic illustration of a steerable catheter assembly including independent magnitude and direction control of the attached catheter.

Referring to FIG. 1, the present application relates to steerable catheter assemblies 1 that utilize various mechanisms to accomplish independent control of catheter flex magnitude and catheter flex direction to provide improved steerability of an attached catheter 2. Utilizing a mechanism for determining a circumferential angle and radial magnitude of catheter flex independently from one another gives the user more direct, intuitive, and fine control of catheter steering. The embodiment pictured in FIG. 1 shows a catheter 2 that defines a longitudinal axis extending between proximal end 8 and distal end 9. The catheter 2 further defines a circumference C (shown in FIG. 1) that further defines a radius R surrounding the longitudinal axis. The catheter 2 can flex radially and is controlled by control handle 5, which can include independent controls for flex magnitude 6, which determines the variable radial distance R of flex of the distal end 9 of the catheter 2, and flex direction 7, which is the circumferential angle in which flex of the distal end 9 of the catheter 2 occurs.

FIG. 1 illustrates the flex magnitude control 6 and flex direction control 7 conceptually, as these controls can take a number of forms and use a variety of mechanisms further described herein. Flex magnitude control 6 and flex direction control 7 may be any knob, lever, switch, dial, device that receives a manual input or a digital input, or other device that is suitable to receive an input from a user to actuate flex magnitude and flex direction control at a distal end 9 of a catheter 2 or other transluminal device. In embodiments disclosed herein, flex magnitude control 6 and flex direction control 7 determine tension in at least two pull wires (not pictured in FIG. 1). In embodiments described herein, at least two pull wires are attached to control handle 5 and distal end 9 of catheter 2 such that increased tension in a first pull wire in relation to tension in other pull wires pulls the distal end 9 of catheter 2 in the direction of one or more of the wires.

In one exemplary method, starting with the attached catheter having a straightened distal tip, the user can adjust the flex magnitude control 6 a sufficient amount to cause the distal tip of the catheter to flex radially to a desired angle from the longitudinal axis of the straightened position (e.g., to a flex angle of 30 degrees from straight). This flex can be purely radial, with no circumferential motion (e.g., the radial flex can occur while the distal tip is at a fixed circumferential angle of zero degrees). Then, the user can adjust the flex direction control 7 to cause the distal tip of the catheter to gradually change the circumferential angle in which the distal tip is radially flexed. For example, adjusting the flex direction control 7 in one way can cause a clockwise change in the circumferential angle of the distal tip, while adjusting the flex direction control 7 in an opposite way can cause counter-clockwise change in the circumferential angle. This change in the circumferential angle can be made while maintaining the degree of radial flex of the distal tip. Furthermore, when the flex direction control 7 is used to change the circumferential angle of the distal tip flex, the catheter itself does not need to be rotated inside the patient. Instead, the distal tip of the catheter is simply flexed in a different circumferential direction from straight while the rest of the catheter can remain stationary.

In another exemplary method, starting with the attached catheter having a straightened distal tip, the user can first adjust the flex direction control 7 to rotate the cam 14 to a selected circumferential position corresponding with the desired flex direction of the distal tip of the catheter 2 (e.g., 270 degrees clockwise from a designated reference point). Then, the user can adjust the flex magnitude control 6 a sufficient amount to cause the distal tip of the catheter to flex radially in the desired direction to a desired angle from the longitudinal axis of the straightened position (e.g., to a flex angle of 30 degrees from straight). This flex can be purely radial, with no circumferential motion (e.g., the radial flex from zero to 30 degrees can occur while the distal tip is at the fixed circumferential angle of 270 degrees).

Figure 2:
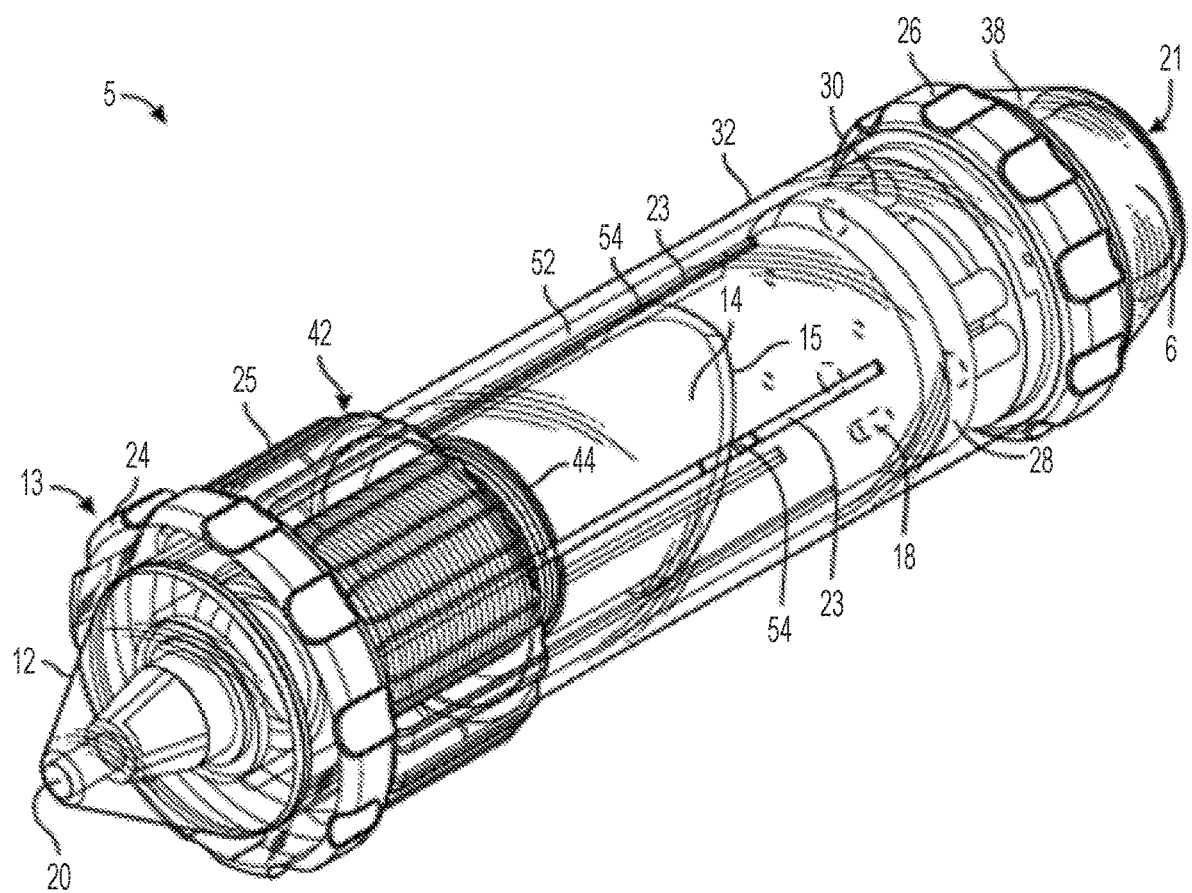
FIG. 2 is a perspective view of an exemplary cam-and-follower-controlled, multi-direction control handle for a steerable catheter assembly.
Figure 3:
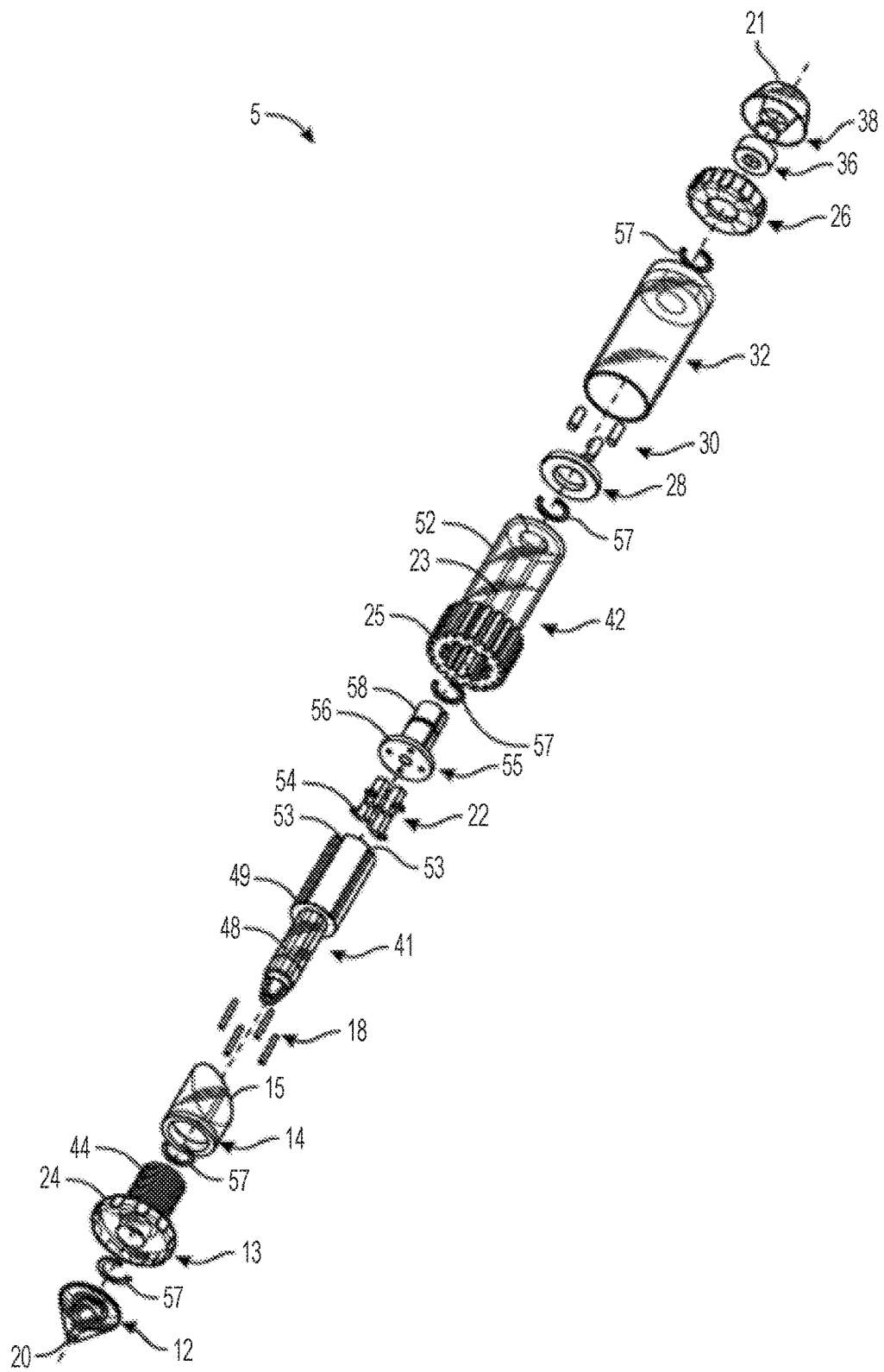
FIG. 3 is an exploded perspective view of the control handle of FIG. 2.

FIGS. 2 and 3 illustrate an embodiment of a catheter control handle 5 that provides cam-controlled multi-directional steerability for an attached catheter 2 (not pictured in FIGS. 2 and 3, but see FIG. 1). A distal end 20 of the handle can be coupled to a catheter 2 (see catheter 2 in FIG. 1) or other elongated and steerable tubular or transluminal device for insertion into a patient, while a proximal end 21 may include luminal access for passage of other devices, pull wires, and/or fluids through the handle 5 and the attached catheter.

The handle 5 of FIGS. 2 and 3 can comprise a cam member 14 having a sloped cam contact surface 15 along which followers 22 slide. The followers 22 are constrained to only axial motion such that they act as cam followers. Followers 22 of the embodiment pictured in FIGS. 2 and 3 are sliders though other suitable types of followers, as described further herein, will also function with various other embodiments of the present invention. The followers 22 can be coupled to pull wires (not pictured in FIGS. 2 and 3) running along sides of the catheter 2 (see FIG. 1) such that axial motion of the followers 22 in slots 23 applies/adjusts tension on the attached pull wires. Any number of followers 22 and pull wires can be included.

The handle 5 in FIGS. 2 and 3 can include a first knob 24 (referred to herein as the "flex knob") that causes axial translation of the cam 14 with respect to a longitudinal axis extending between distal end 20 and proximal end 21. The flex knob 24 acts as the flex magnitude control (6 of FIG. 1). The handle 5 in FIGS. 2 and 3 can further include a second knob 25 (referred to herein as the "steering knob") that causes circumferential rotation of the cam 14 with respect to the longitudinal axis of the handle 5. The steering knob 25 acts as the flex direction control (7 of FIG. 1). The handle 5 of FIGS. 2 and 3 can further optionally include a third knob 26 (referred to herein as the "clutch knob") that serves as a clutch or break to lock in the rotational position of the cam 14 selected by the steering knob 25 while allowing adjustment to the axial position of the cam via the flex knob 24.

By rotating the flex knob 24, the user can cause the cam 14 to move axially relative to the rest of the handle 5, which causes all of the followers 22 that are engaged with the cam to move axially a corresponding distance, which in turn causes all of the pull wires attached to the followers 22 to increase or decrease in tension together, resulting in a change in the magnitude of the radial flex of the distal tip (9 in FIG. 1) of the attached catheter, without changing the circumferential angle of the flexed catheter tip (9 in FIG. 1) with respect to the longitudinal axis of the catheter.

By rotating the steering knob 25, the user can cause the cam 14 and its sloped contact surface 15 to rotate around the central longitudinal axis of the handle, causing one or more of the followers 22 to move distally in the slots 23 and one or more other sliders 22 to move proximally in the slots 23, depending on which part of the sloped contact surface 15 is in contact with each follower 22. This can cause increased tension in one or more pull wires and simultaneous reduction in tension in one or more other pull wires, which results in the flexed distal tip of the attached catheter pivoting about its longitudinal axis and changing the circumferential angle in which it is radially flexed (without rotating the whole catheter inside the patient).

Accordingly, each of the flex knob 24 and the steering knob 25 can individually adjust some or all of the followers 22 depending on which followers 22 engage the sloped contact surface 15 of cam 14. Each of the knobs 24 and 25 can generate independent, yet complimentary, resultant adjustment to the distal tip of the catheter.

The flex knob 24 and the steering knob 25 can be rotated at the same time or individually. For example, in an exemplary method, the two knobs can be rotated at the same time (in either the same rotational direction or in opposite rotational directions). Simultaneous rotation of the two knobs can cause the cam 14 to slide axially and rotate circumferentially at the same time, which causes the distal tip of the catheter (9 in FIG. 1) to both change its magnitude of flex and change the circumferential direction of the flex. The handle 5 can be manually operated with one hand or with two hands. Since the knobs 24 and 25 are close to each other, the user can operate both knobs with one hand while holding the handle 5.

As shown in FIGS. 2 and 3, the handle 5 can include a distal nose cone 12, a flex component 13 that can include the flex knob 24 and a threaded body 44, the cam 14, pins 18, a stationary follower guide 41 including a distal body 48 and a proximal body 49 with follower grooves 53, followers 22 each having an outwardly projecting slider pin 54, a back plug 55 with a disk portion 56 and a proximal shaft 58, a positioning component 42 including the steering knob 25 and a proximal cylinder 52 with slots/grooves 53, a washer 28, spacers 30, an outer sheath 32, the clutch knob 26, proximal gasket 36, and proximal end cap 38 forming the proximal end 21. Various retainers/fasteners (e.g., retaining rings 57) can also be included. As shown in FIG. 3, the followers 22 can slide axially along the grooves 53 while their slider pins 54 project out to the radial dimension of the cam 14. The cam 14 is positioned between the proximal body 49 and the proximal cylinder 52, such that the slider pins 54 contact the follower contact surface 15 of the cam 14. The cam 14 can be coupled to the positioning component 42 such that rotation of the steering knob 25 causes the cam to rotate, while at the same time the proximal cylinder 52 allows the cam 14 to slide axially between the stationary slider guide 41 and the positioning component 42.

The threaded body 44 of the flex component 13 can be positioned around the distal body 48 of the stationary slider guide 41 and also engaged to the cam 14 such that rotation of the flex component 13 drives the cam axially relative to the stationary slider guide 41 and the cylinder 52 of the positioning component 42.

The clutch knob 26 can have an engaged position and a disengaged position. When in the engaged position, the steering knob 25 can be locked such that the circumferential angle of the distal tip of the attached catheter is fixed, while allowing the flex knob 24 to drive the cam 14 axially and change the magnitude of flex of the distal tip of the attached catheter. Clutch knob 26 can be configured in an alternate embodiment such that in an engaged position, flex knob 24 is locked holding the magnitude of flex of the attached catheter constant while allowing steering knob 25 to rotate the cam 14 circumferentially and change the circumferential angle of flex. When the clutch knob 26 is in the disengaged position, both the flex knob 24 and the steering knob 25 are functional. In another embodiment, the handle 5 includes two clutch knobs, one for locking the steering knob 25 and one for locking the flex knob 24.

Each of the followers 22 can be attached to one end of a pull wire that runs distally through the handle 5, out the distal end 20, and along the attached catheter. The handle 5 can include 2 or more followers 22 and associated pull wires. Four followers 22 are included in the illustrated embodiment, each spaced about 90 degrees apart from each other circumferentially, though as discussed further below, alternate numbers of followers arranged in different circumferential spacing arrangements can be used to affect control characteristics of the steerable catheter assembly.

Figure 43:
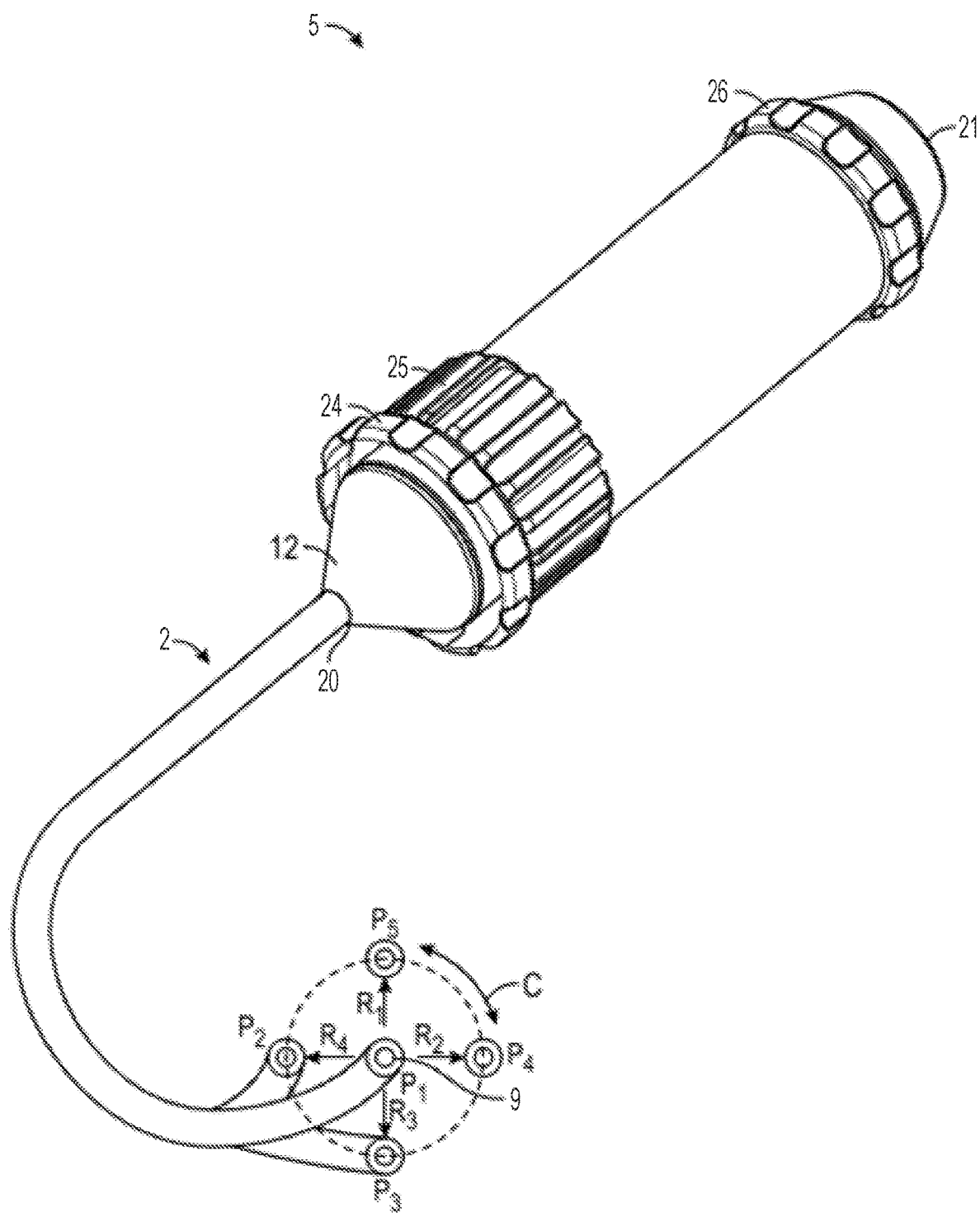
FIG. 43 is a perspective view of an exemplary embodiment of a steerable catheter assembly having a multi-direction control handle and an attached catheter.

With reference to FIG. 43, which shows the control handle embodiment of FIGS. 2 and 3 with an attached steerable catheter 2, rotating the flex knob 24 causes the catheter 2 to flex in a radial direction, such as any of the four exemplary radial directions R1, R2, R3, and R4 labeled in FIG. 43, or any direction in between the labeled directions. When the cam member 16 is in its distal position, i.e. not engaged with any followers 22, the catheter 2 can be relaxed and/or not flexed, such as is shown by the position P1 in FIG. 43. When the cam member is driven axially, however, moving the followers 22 with it, the attached pull wires are tensed, causing the catheter 2 to flex radially, for example, to any of the flexed positions labeled P1, P2, P3, or P4 in FIG. 43. The circumferential angle in which the catheter 2 flexes is determined by the position of the steering knob 25. The rotational position of the steering knob 25 can correspond to circumferential motion of the flexed catheter 2 in the circumferential direction, labeled with double-headed arrow C in FIG. 43. For example, if the catheter 2 is currently in the flexed position P4, rotation of the steering knob 25 (while the flex knob is stationary) can move the catheter 2 to position P3 or to position P5 along the dashed line (while the catheter 2 does not rotate about its central longitudinal axis). If the catheter 2 is currently in the unflexed position P1, rotation of the steering knob 25 may not cause any motion of the catheter 2 (not even rotation of the catheter 2 about its central longitudinal axis), but can determine in which radial direction (e.g., R1, R2, R3, and R4) the catheter 2 will flex when the flex knob 24 is subsequently rotated. By adjusting the flex knob 24 and the steering knob 25 in combination (simultaneously or one at a time), the catheter 2 can be steered to any flex position within the dashed circle in FIG. 43 (assuming the dashed circle represents the maximum degree of flex), without rotating the catheter 2 about its central longitudinal axis within a patient's body.

Figure 4:
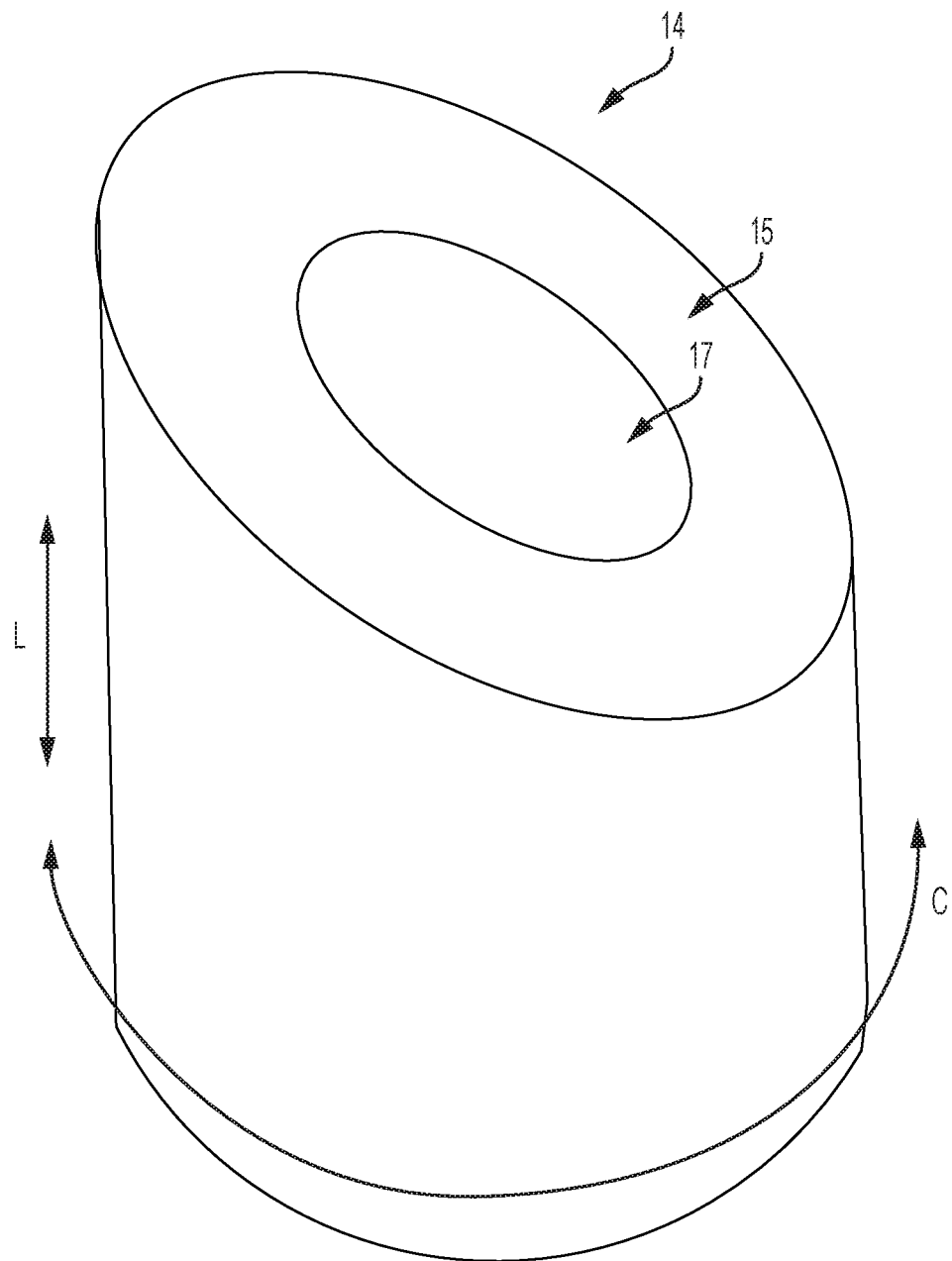
FIG. 4 is a perspective view of an exemplary cam structure.
Figure 4A:
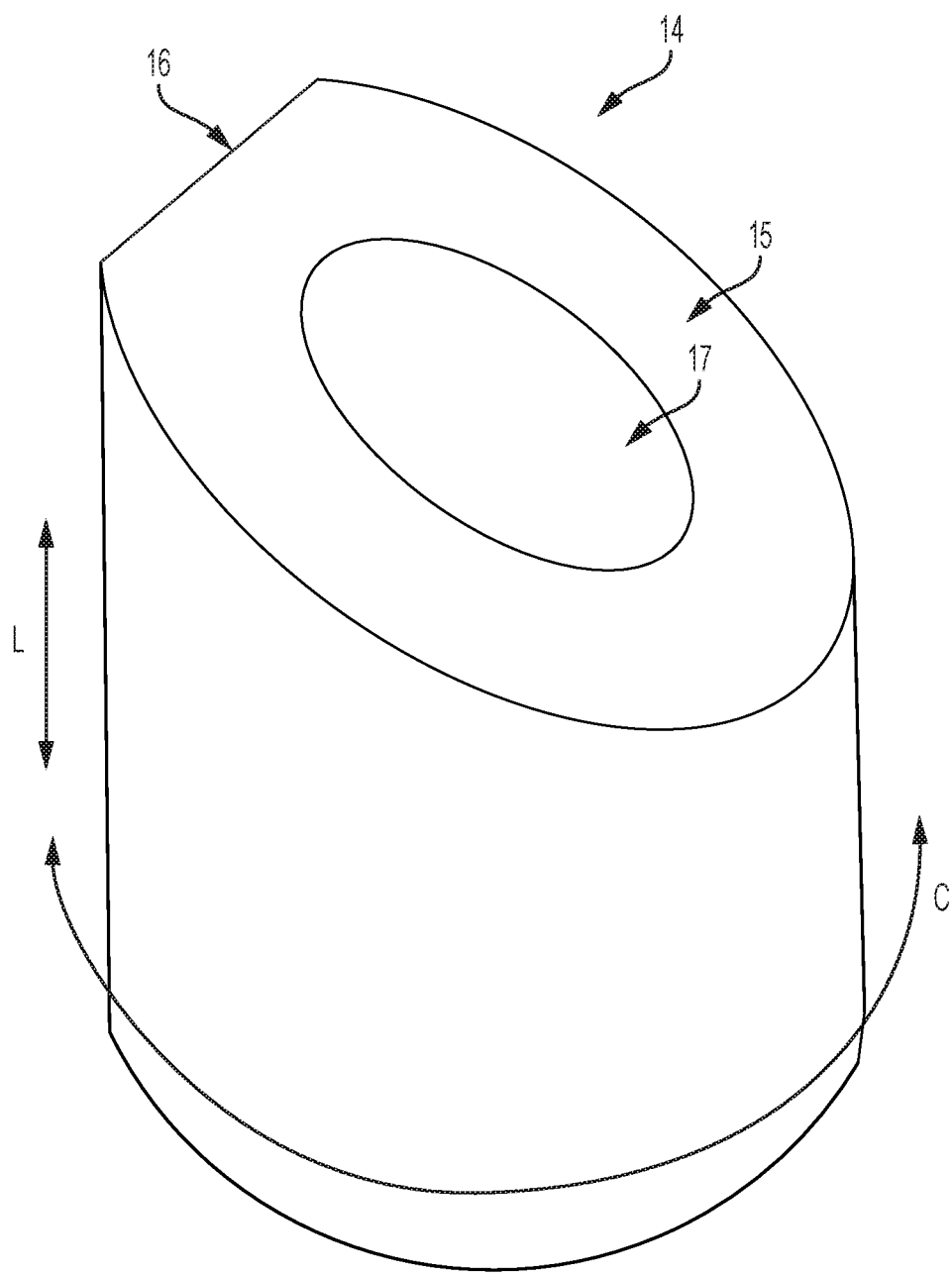
FIG. 4A is a perspective view of the cam of FIG. 4 with a dwell in the cam contact surface.

FIGS. 4 and 4A show embodiments of cam 14 with cam follower contact surface 15. Dual headed arrow C describes the circumferential direction with respect to the longitudinal axis L of a control handle in which the cam 14 is housed. The cam 14 is oriented such that contact surface 15 can engage followers, and when the cam 14 is adjusted axially or rotationally (circumferentially about the longitudinal axis L), the tension in pull wires coupled to the followers is adjusted. Thus, the cam contact surface 15 can be oriented longitudinally L in proximal or distal directions with respect to the housing.

FIG. 4 includes a follower contact surface 15 with a constant axial slope as a function of circumferential angle. The contact surface 15 can comprise any planar or non-planar profile, such as a planar surface that defines an oblique plane that is not parallel or perpendicular to the longitudinal axis of the handle. A cam follower contact surface of the present invention can further have shapes and/or slopes including flats, rounds, dwells, divots, valleys, detents, or other shapes. The shape of the cam follower contact surface 15 ultimately determines interactions with the followers when a user provides a flex magnitude or flex direction input, i.e. the cam 15 is adjusted axially or rotationally. FIG. 4A shows an embodiment of a cam 14 wherein cam follower contact surface 15 includes a dwell 16. The contact surface 15 can comprise an annular surface that extends circumferentially around a central shaft and/or central lumen of the handle in which the cam 14 is housed. A lumen 17 is shown in FIGS. 4 and 4A that will accommodate such a central shaft and/or central lumen of the handle through cam 14.

Further discussion of embodiments with alternatively shaped cams is provided below with reference to FIGS. 12-16D, 20A, and 20B. The follower contact surface 15 of the cam 14 can be configured to provide a desired balance between fine control of the flex angles and a minimal amount of control adjustment that is necessary to adjust the flex angles and magnitude. For example, a steeper slope on the cam results in more change in radial flex per adjustment of the flex magnitude control, while a less sloped cam surface provides more fine control of the exact magnitude of flex. Modifications to cam 14 shape allow for further variations and adjustments in control and address problems of "drift" that can be present in cam-follower systems as discussed further below.

The use of a cam member in the disclosed control handles can provide an infinite degree of choice in selecting a desired flex position of the distal tip of an attached catheter, as the cam member can provide an analog adjustment mechanism. Furthermore, with regard to the control handle 5, an increased number of sliders and/or an increased number of pull wires that are included and coupled to the followers 22 can improve the smoothness of the analog control systems described herein.

FIGS. 5-20B graphically illustrate catheter flex as a function of cam and follower 22 movement, the interface between cam follower contact surface 15, the shape of cam contact surface 15, and the number and spacing of followers 22. All cam follower contact surfaces illustrated in the figures are shown extending from point A (displayed on the left for illustrative purposes) around to the same point A (displayed on the right for illustrative purposes). This illustration indicates a continuous cam follower contact surface extending around the circumference of the longitudinal axis defined by a control handle housing. FIGS. 5-15, 18A-18B, and 20A-20B are graphical depictions of embodiments including four followers F1, F2, F3, and F4. Several of these figures also depict a continuous arrangement mapped to a line that extends from left to right, wherein the repetition of one follower (here F3 indicates the same follower and thus continuity of the follower arrangement).

Figure 6:
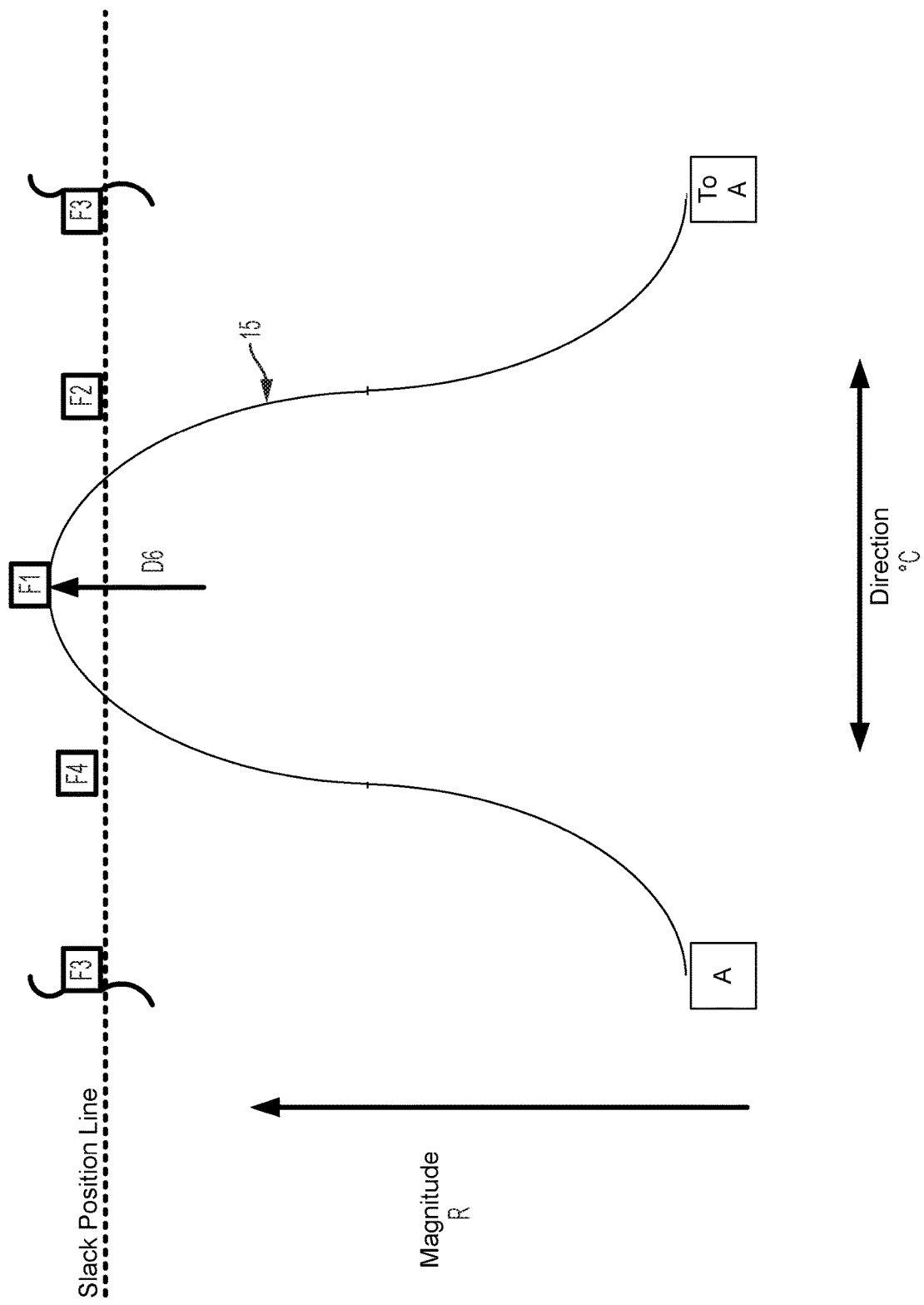
Figure 7:
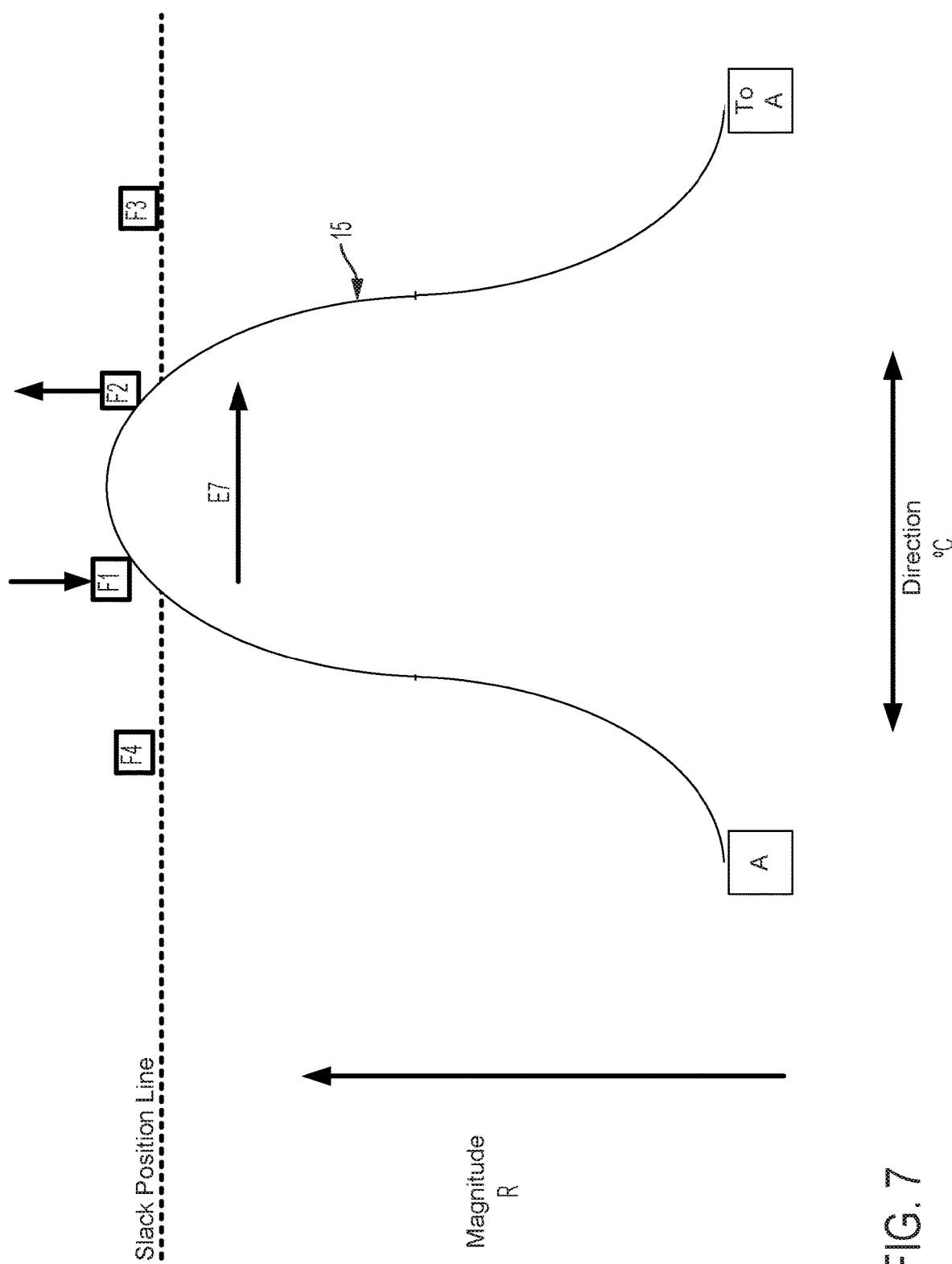
Figure 8:
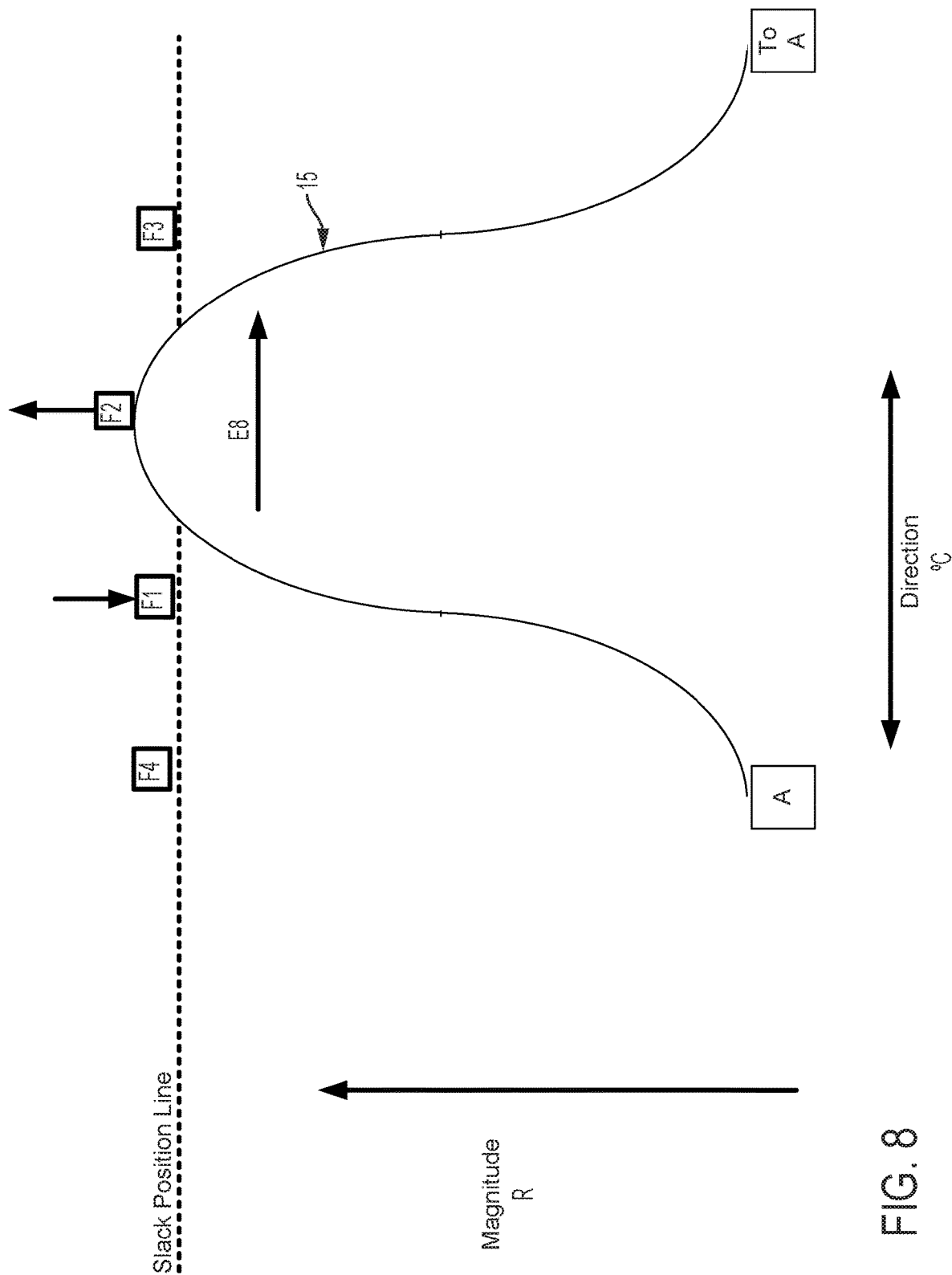

FIG. 5 graphically depicts an embodiment of a smooth cam follower contact surface 15, like that illustrated in FIG. 4, with four followers, F1, F2, F3, and F4. In FIG. 5, cam follower contact surface 15 is axially positioned such that it is not engaged with any of the followers. In this position, pull wires coupled to each follower are at minimum tension, thus providing a zero magnitude of flex. FIG. 6 shows the cam follower contact surface 15 of FIG. 5 after the surface 15 has been axially translated as indicated by arrow D6 causing a corresponding increase in magnitude of flex R. In the embodiment displayed in FIG. 6, contact surface 15 engages with follower F1 only, thereby increasing tension in the pull wire coupled to follower F1 and pulling the attached catheter in the radial direction of F1. Thus, in embodiments disclosed herein, axially adjusting contact surface 15 causes a corresponding adjustment of flex magnitude in the direction of the followers engaged by contact surface 15. FIG. 7 shows the cam follower contact surface 15 of FIG. 6 after the cam has been rotated as indicated by arrow E7 causing a corresponding change in direction of flex ° C. Rotation of the cam as indicated by arrow E7 causes contact surface 15 to engage follower F2 while continuing to engage follower F1, but at a different axial position. Thus, flex magnitude in the direction of a pull wire attached to F1 is reduced and flex magnitude in the direction of a pull wire attached to F2 is increased, resulting in a directional shift of the attached catheter toward F2 in FIG. 7 relative to the catheter's position as indicated in FIG. 6. As shown in FIG. 8, further rotation of the cam as indicated by arrow E8, causes contact surface 15 to completely disengage with follower F1 and engage with follower F2 at a new axial position. Accordingly, flex magnitude in the direction of a pull wire attached to F1 is further reduced and flex magnitude in the direction of a pull wire attached to F2 is further increased, resulting in an additional directional shift of the attached catheter toward F2 in FIG. 8 relative to the catheter's position as indicated in FIG. 7.

Figure 9:
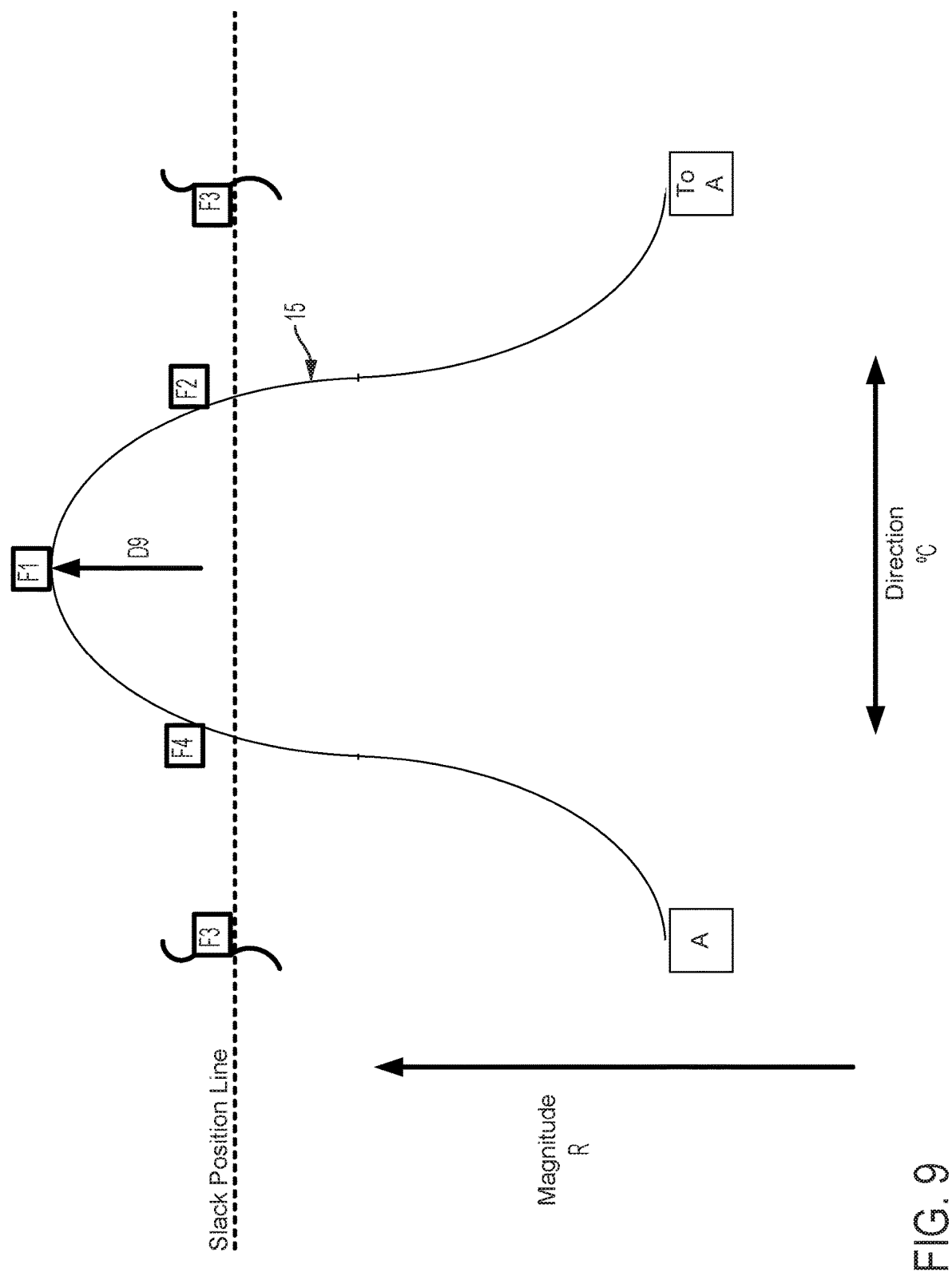
Figure 10:
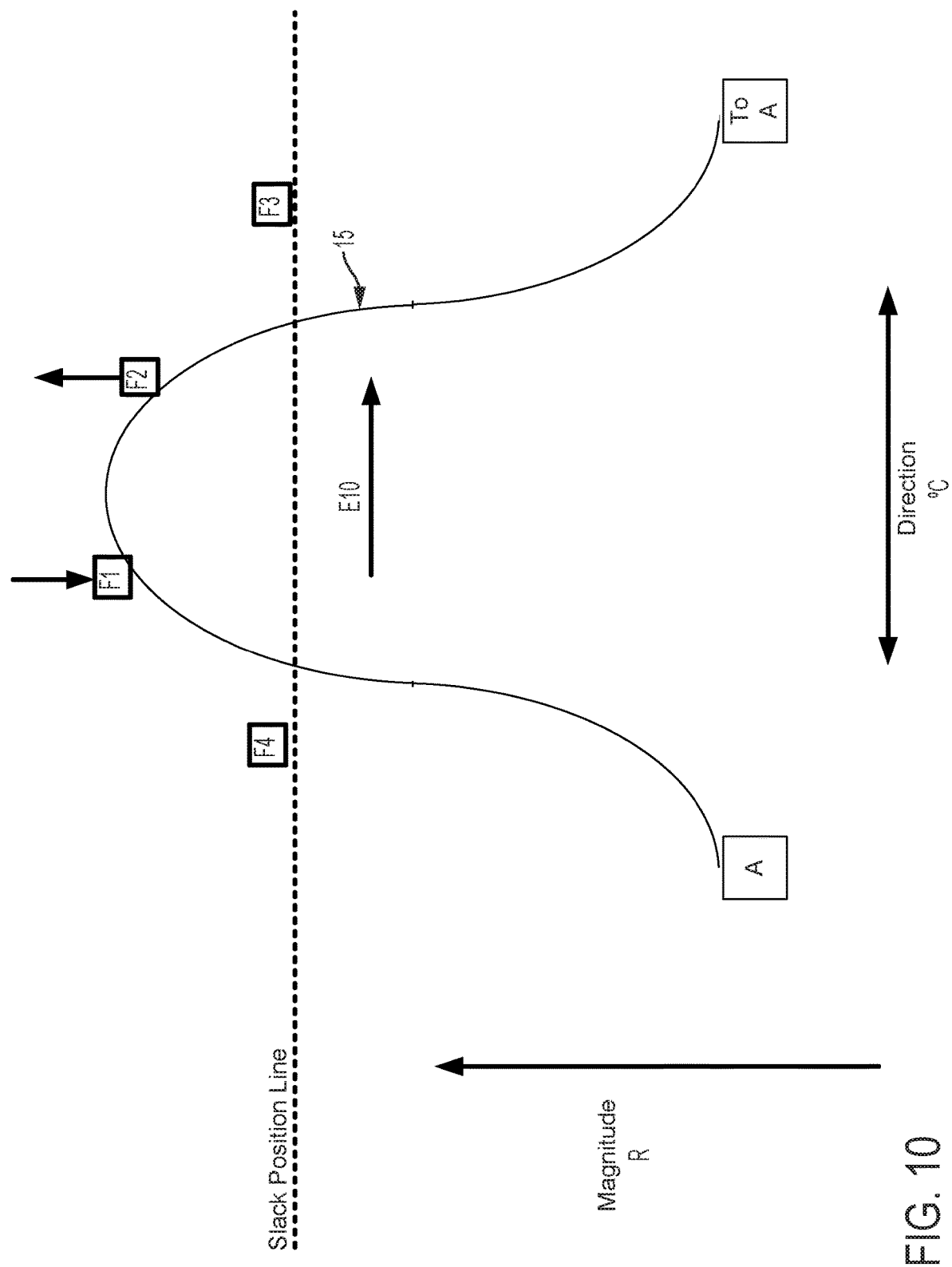
Figure 11:
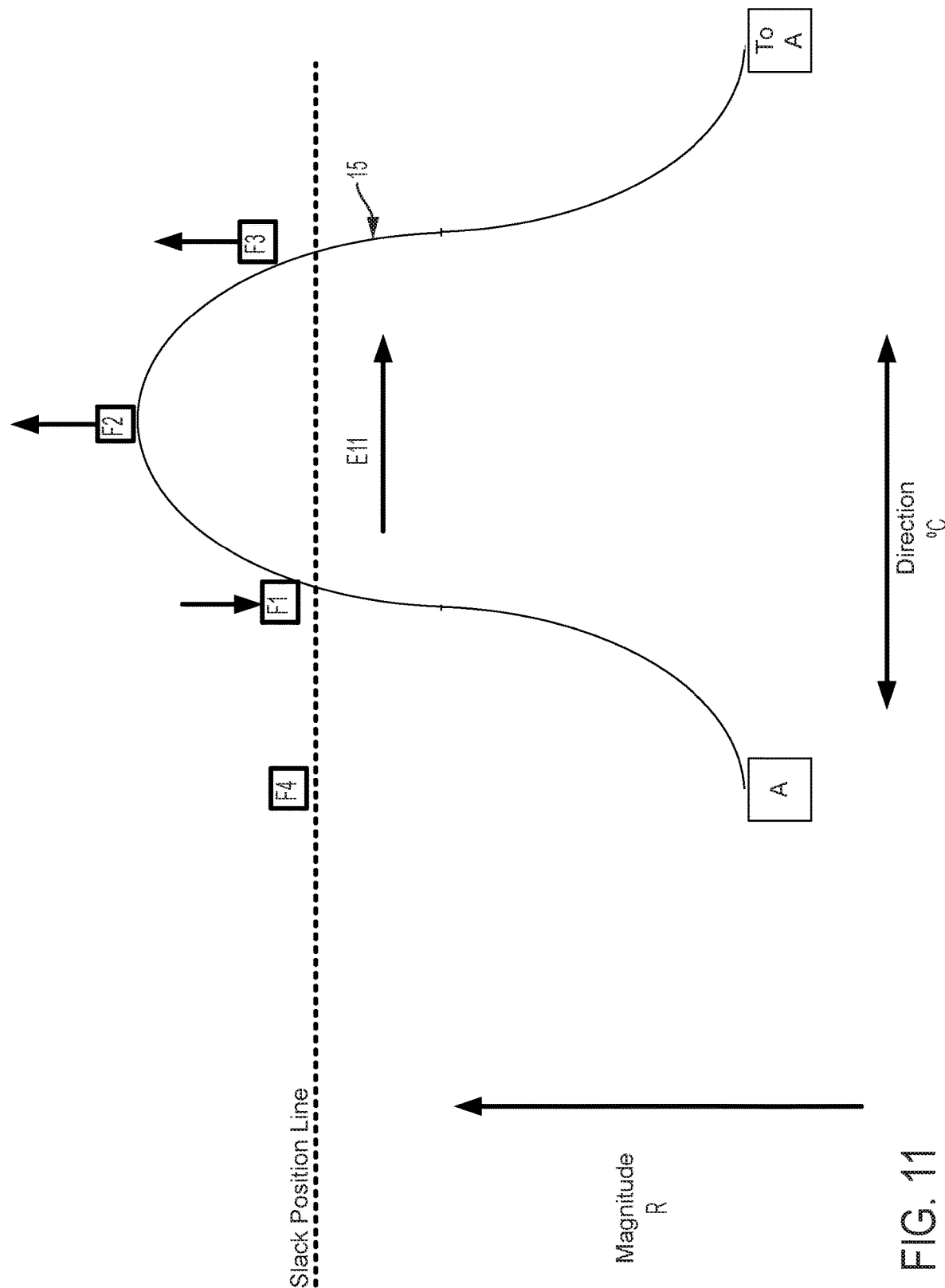

FIGS. 9-11 show the positions of the cam surface 15 and followers F1, F2, F3, and F4 after the cam surface has been axially advanced. In FIG. 9, the cam surface advances the follower F1 (as compared to FIG. 6) and also engages and advances followers F2 and F4 to a lesser extent. As a result, the magnitude of flex in the direction of follower F1 is increased as compared to FIG. 6. In FIG. 10, the followers F1, F2 are advanced (as compared to FIG. 7). As a result, the magnitude of flex in the direction of followers F1, F2 is increased as compared to FIG. 7. In FIG. 11, the follower F2 is advanced (as compared to FIG. 8) and the cam also engages followers F1, F3 to a lesser extent. As a result, the magnitude of flex in the direction of follower F2 is increased as compared to FIG. 8.

Figure 12:
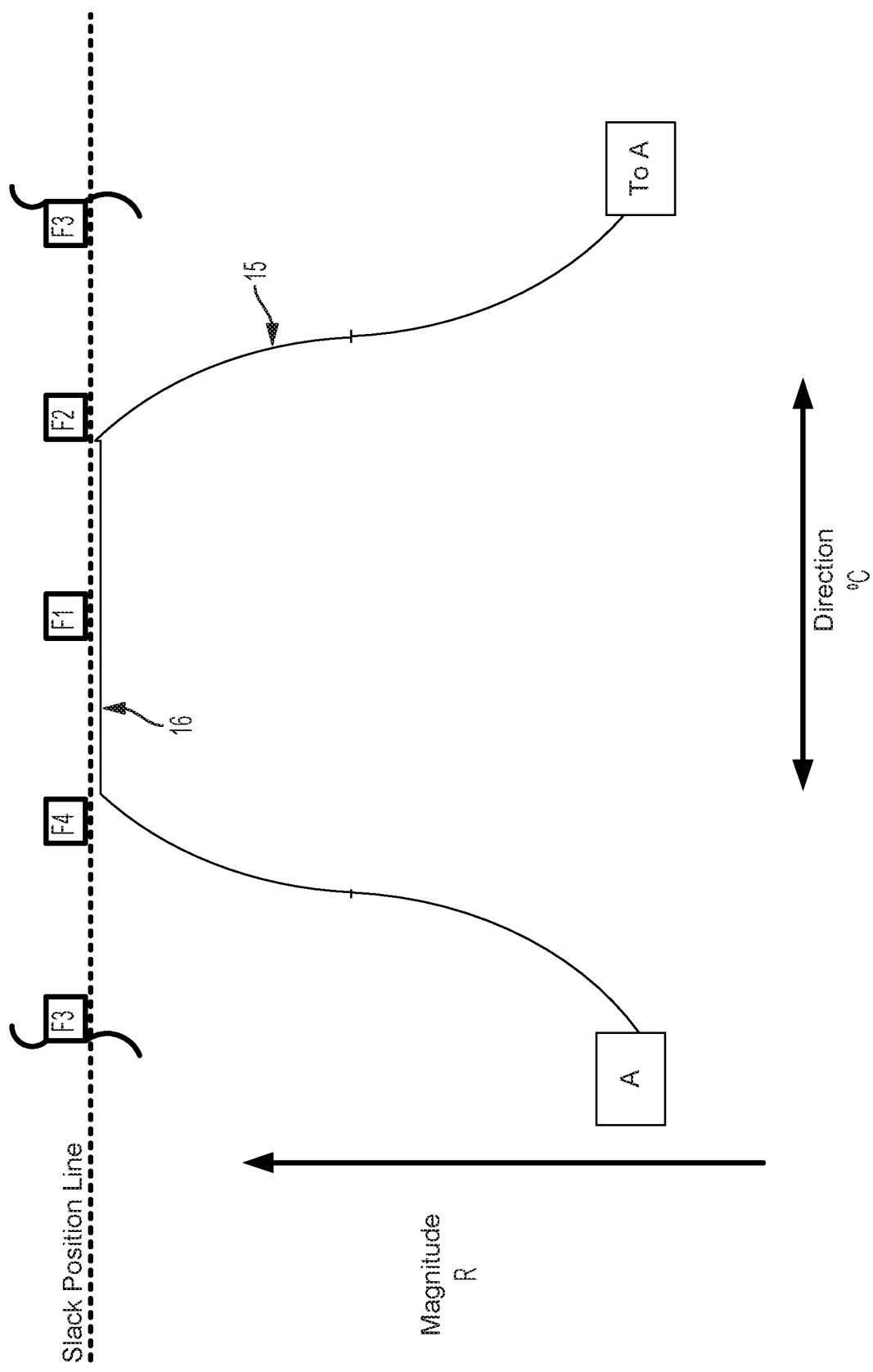
Figure 13:
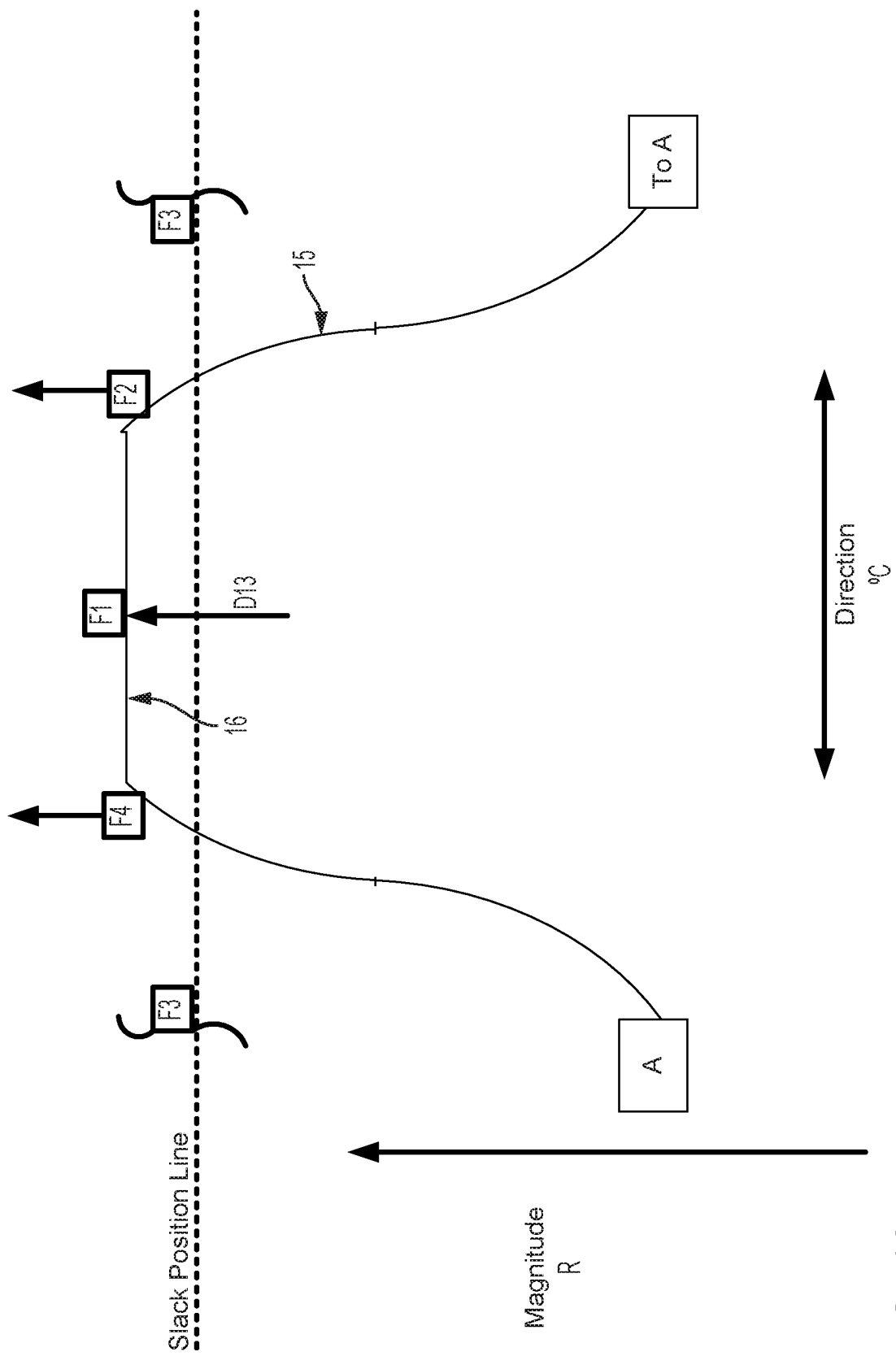
Figure 14:
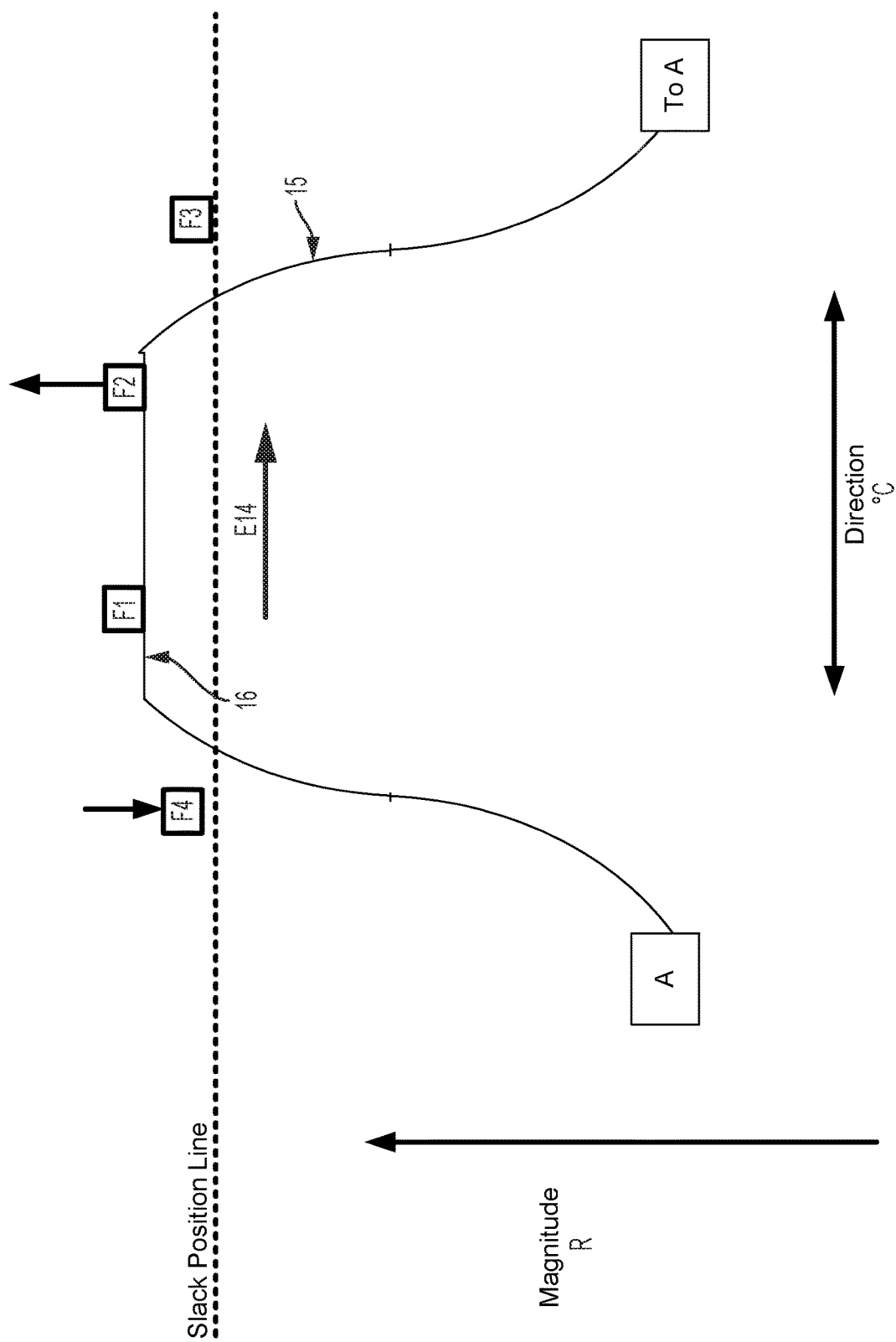
Figure 15:
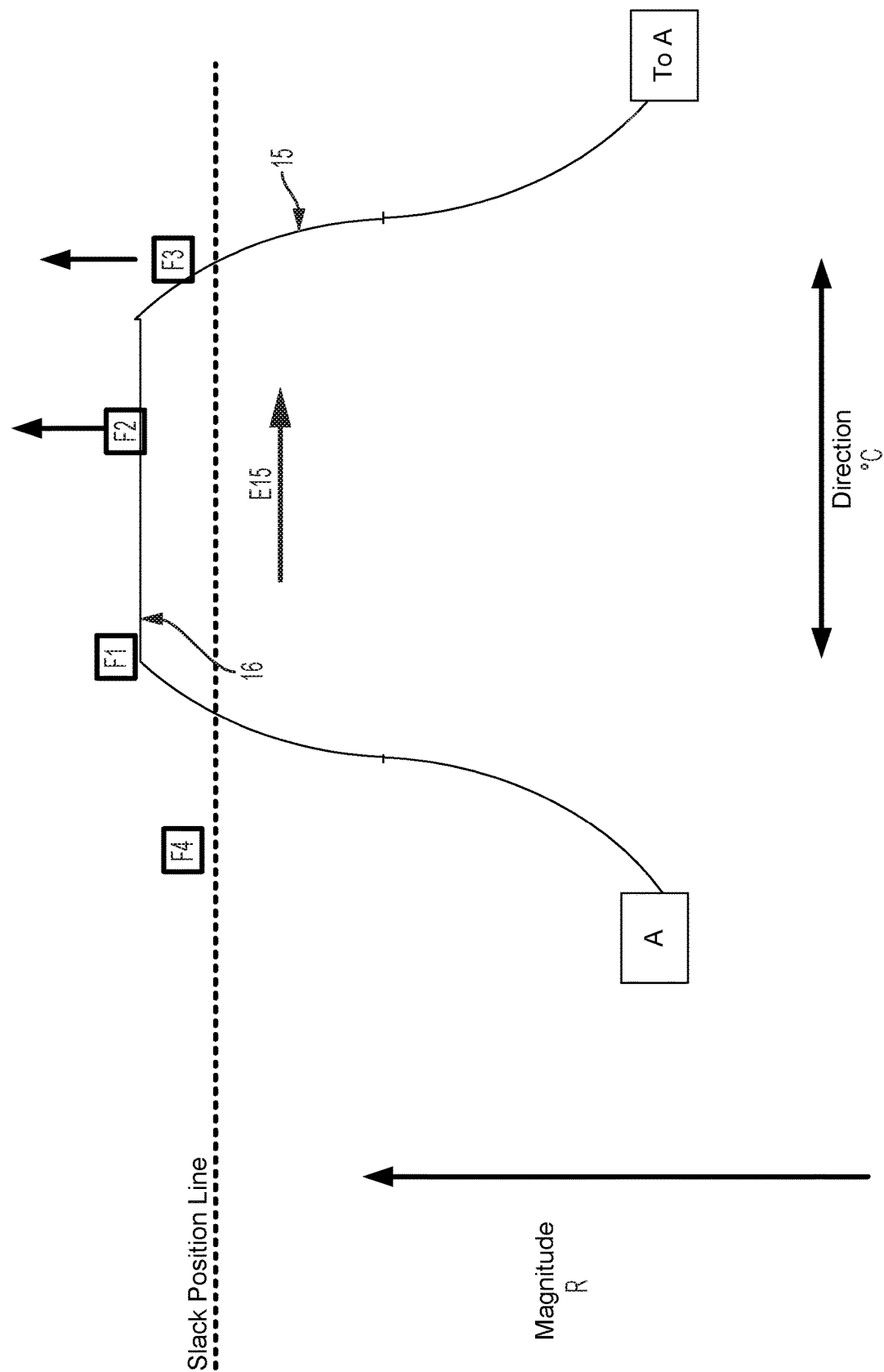

FIGS. 12-15 graphically depict an embodiment of a smooth cam follower contact surface 15 with a dwell 16. In this example, the dwell 16 is sized so that the cam surface always engages at least two followers. Four followers, F1, F2, F3, and F4 are illustrated in FIGS. 12-15. FIG. 12 shows contact surface 15 axially positioned so that dwell 16 is level with the Slack Position Line. The cam embodiment described in FIG. 12 does not affect magnitude of catheter flex in this position, where the cam embodiment described in FIGS. 5-11 would in the same axial position. FIG. 13 shows contact surface 15 of the cam and follower system embodiment described in FIG. 12 translated axially as indicated by arrow D13. In this position, contact surface 15 engages followers F1, F2, and F4. As compared to a follower engaged with a cam without a dwell in the same axial position, follower F1 does not create as much tension in an attached pull wire and thus does not result in as much flex magnitude in the direction of the F1 follower. FIG. 14 shows contact surface 15 of the cam and follower system embodiment described in FIG. 13 rotated as indicated by arrow E14.

In this position, contact surface 15 engages followers F1, and F2, but not F4, to rotate the catheter to the combined direction between followers F1 and F2. Because followers F1 and F2 engage contact surface 15 at dwell 16, followers F1 and F2 are equally axially translated, thus exerting equal tension on attached pull wires and causing equal flex magnitude in the directions of followers F1 and F2. Some further rotation of contact surface 15 as indicated by arrow E14 in FIG. 14 may be made such that the dwell 16 of contact surface 15 remains in contact with followers F1 and F2 before follower F3 is engaged. Despite some directional adjustment indicated by arrow E14, no change occurs in catheter direction. The dwell 16 thus provides tolerance for imprecision of adjustments made by a user of embodiments of steerable catheter assemblies described herein. Insignificant or unintentional adjustments to the directional control by the user can effectively be "ignored" by the disclosed device when the dwell 16 is used. The size of the dwell can be increased to "ignore" larger adjustments or reduced to have the opposite effect. Further, as discussed below, where the length of the dwell at least matches the minimum distance between followers, a dwell solves the problem of "drift." In FIG. 15, the cam engages the followers F1, F2, F3, and the direction of catheter flex changes. The dwell also keeps the cam surface in contact with at least two followers at all times, which prevents the catheter from jumping from one rotational position to another as the cam is rotated.

FIGS. 16A-16D show graphical depictions of alternate embodiments of contact surface 15. As discussed above, the cam and follower contact surface of embodiments of the present invention can comprise any planar or non-planar profile, such as a planar surface that defines an oblique plane that is not parallel or perpendicular to the longitudinal axis of the control handle that houses the cam. A cam follower contact surface 15 can comprise shapes and/or slopes including flats, rounds, dwells, divots, valleys, detents, or other shapes. The shape of the cam follower contact surface 15 ultimately determines interactions with the followers when a user provides a flex magnitude or flex direction input, i.e. the cam 15 is adjusted axially or rotationally. The follower contact surface 15 of the cam 14 can be configured to provide a desired balance between fine control of the flex angles and a minimal amount of control adjustment that is necessary to adjust the flex angles and magnitude. For example, a steeper slope on the cam results in more change in radial flex per adjustment of the flex magnitude control, while a less sloped cam surface provides more fine control of the exact magnitude of flex.

Figure 16A:
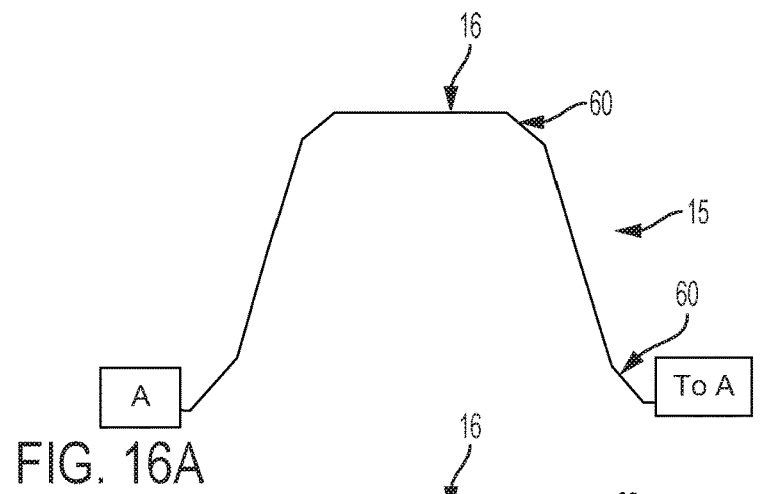
FIGS. 16A-16D illustrate exemplary embodiments of different cam shapes.
Figure 16B:
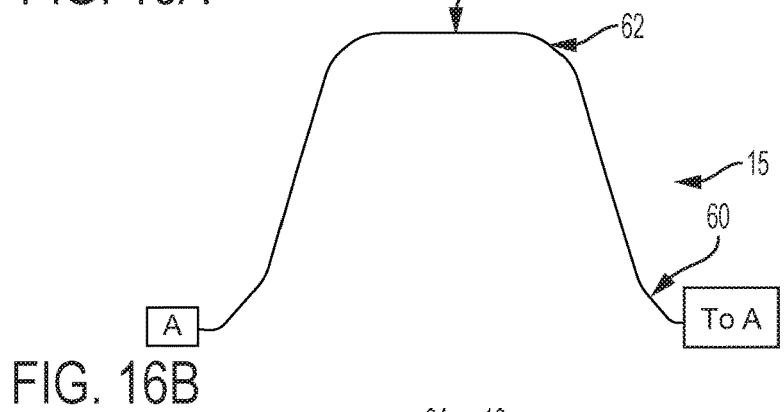
Figure 16C:
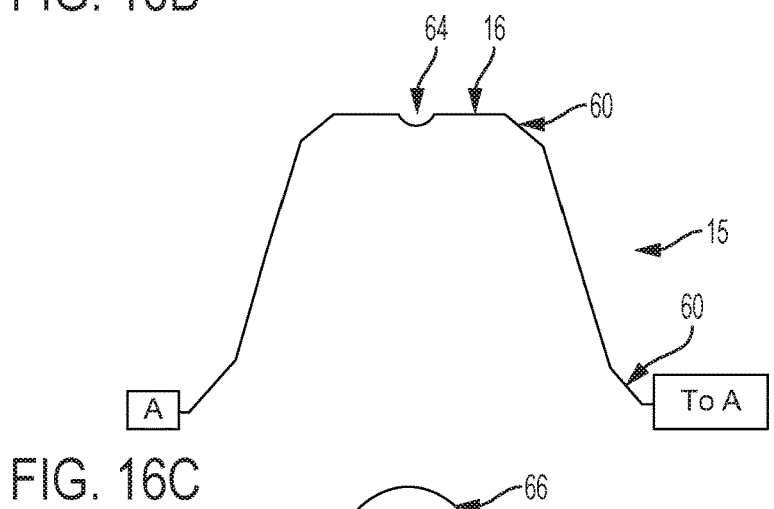
Figure 16D:
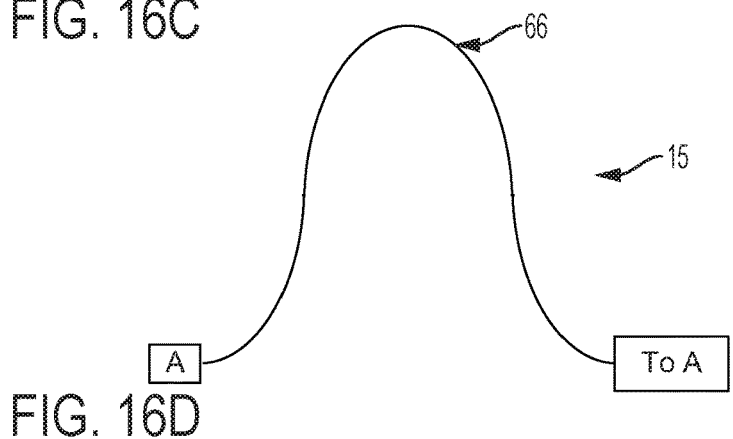

FIG. 16A is a graphical depiction of a cam follower contact surface 15, having a dwell 16, and flats 60. FIG. 16B is a graphical depiction of a cam follower contact surface 15, having a dwell 16, rounds 62, and flats 60. FIG. 16C is a graphical depiction of a cam follower contact surface 15, having a dwell 16, flats 60, and a valley or detent 64. Detent 64 provides the user with tactile feedback as the detent 64 will provide resistance to rotation of the cam when engaged with a follower, and also provides a directional locking function for finer control. FIG. 16D is a graphical depiction of a cam follower contact surface 15 having a smooth surface with increasingly steep sides such that for a given rotation of the cam, the contact surface quickly engages and then quickly disengages followers. Such a contact surface 15 could provide finer control for an embodiment that includes many followers.

Figure 17A:
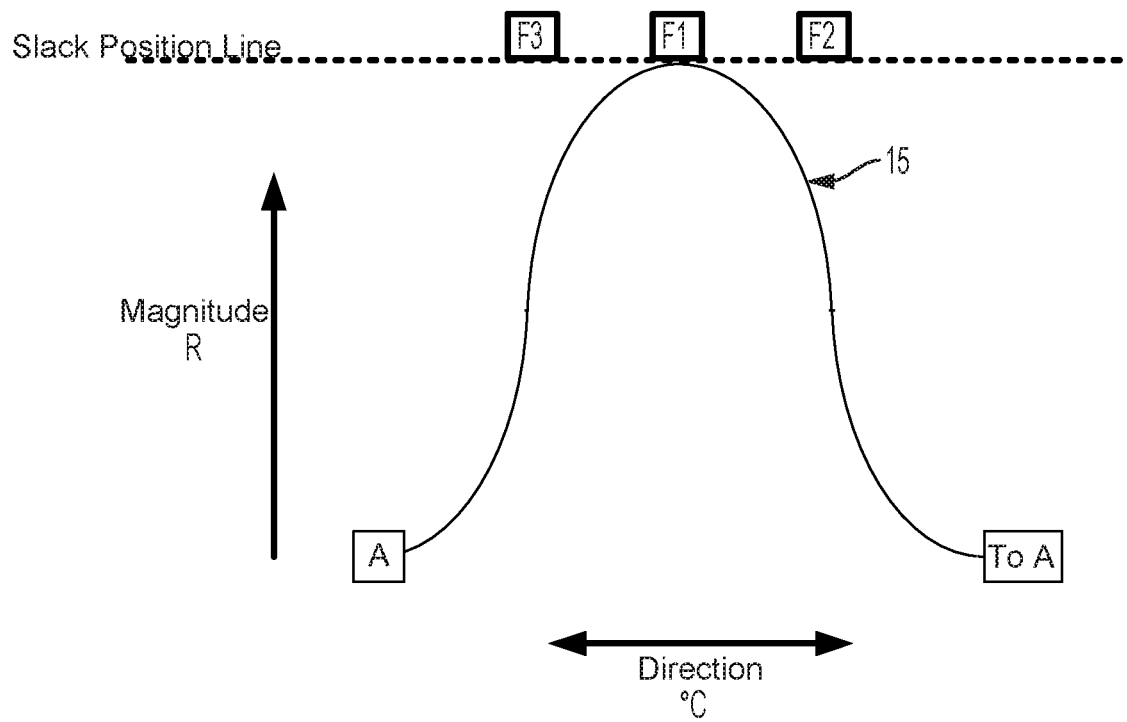
FIG. 17A illustrates a cam and follower arrangement with three followers.
Figure 17B:
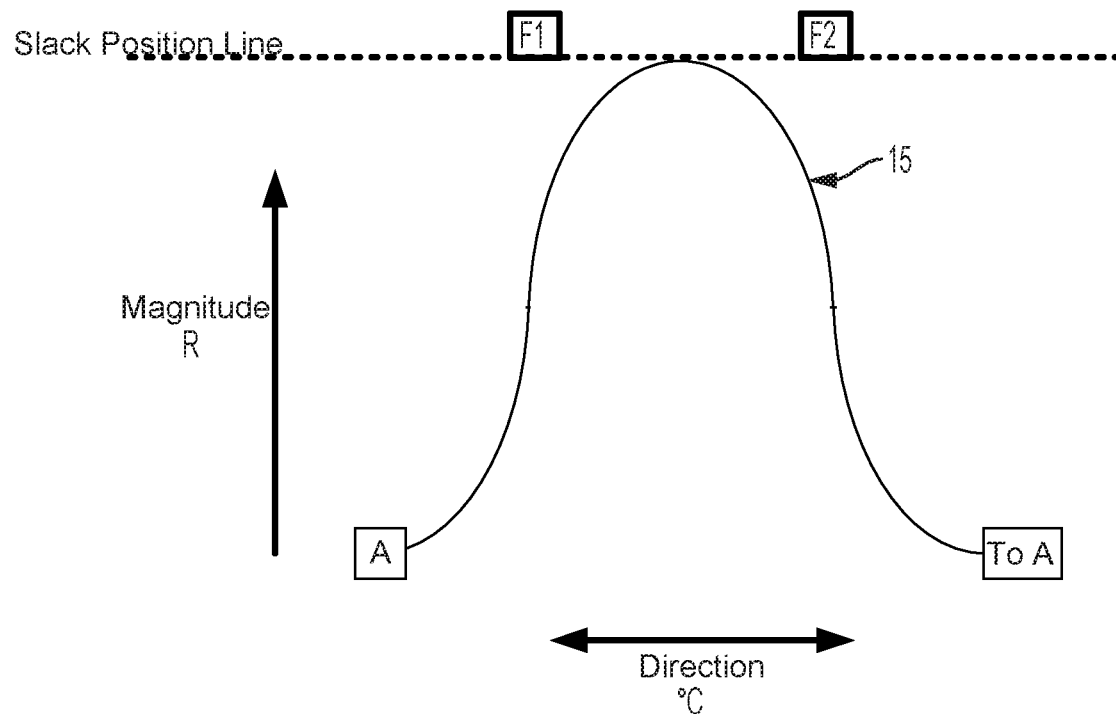
FIG. 17B illustrates a cam and follower arrangement with two followers.

FIGS. 17A and 17B are graphical depictions of cam and follower systems including contact surface 15 and three and two followers, respectively. Lesser numbers of followers decrease fineness of control. Contact surface 15 as shown in the cam follower system embodiment depicted in FIG. 17B shows contact surface 15 between followers F1 and F2. Contact surface 15 of FIG. 17B is capable of engaging no followers even for some positions in which contact surface 15 is axially translated past the Slack Line Position. In such a system, the problem of "drift" is possible. "Drift" is the process whereby, for a constant axial position of the cam, a rotation of the cam causes the cam to totally disengage with all cam followers, thus eliminating tension in attached pull wires. In embodiments described herein, this can correspond with an unexpected (to the user) shift of catheter flex magnitude to zero. As mentioned above, addition of a dwell can eliminate this problem where the dwell is wide enough to span the maximum gap between followers.

Figure 18A:
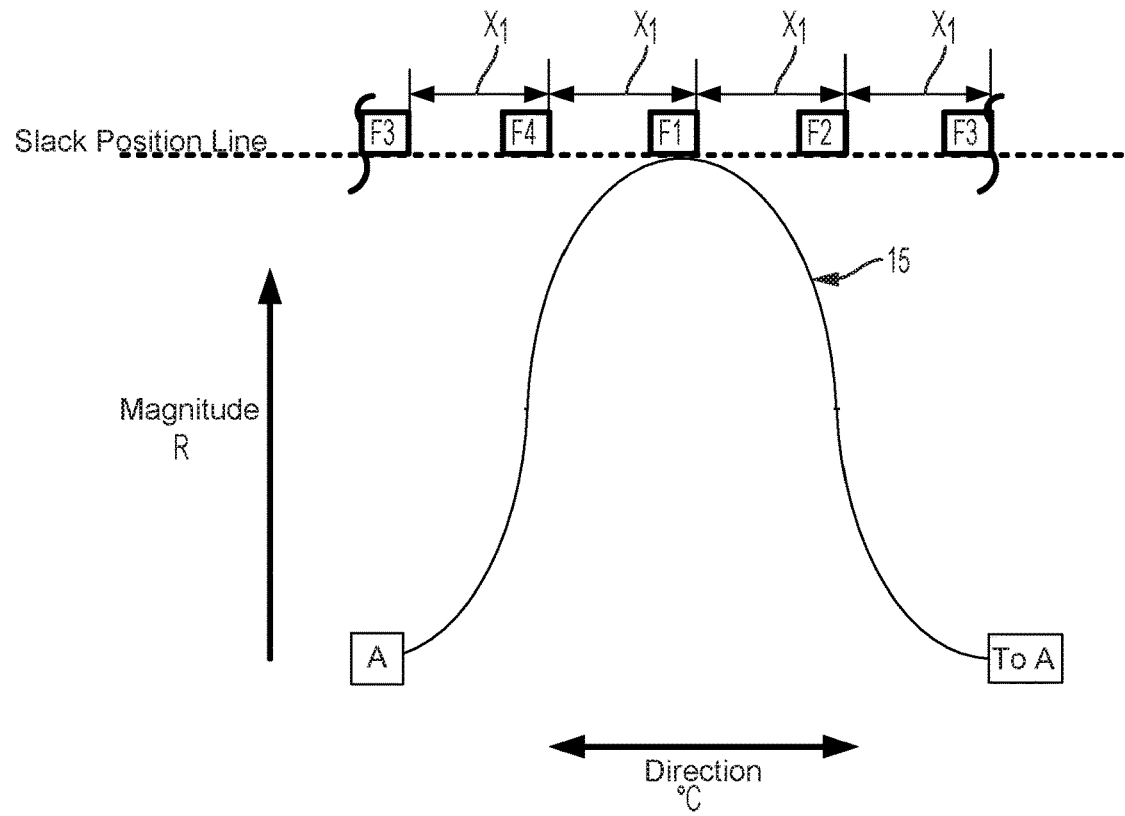
FIGS. 18A and 18B illustrate that the spacing between cam followers can be non-uniform.
Figure 18B:
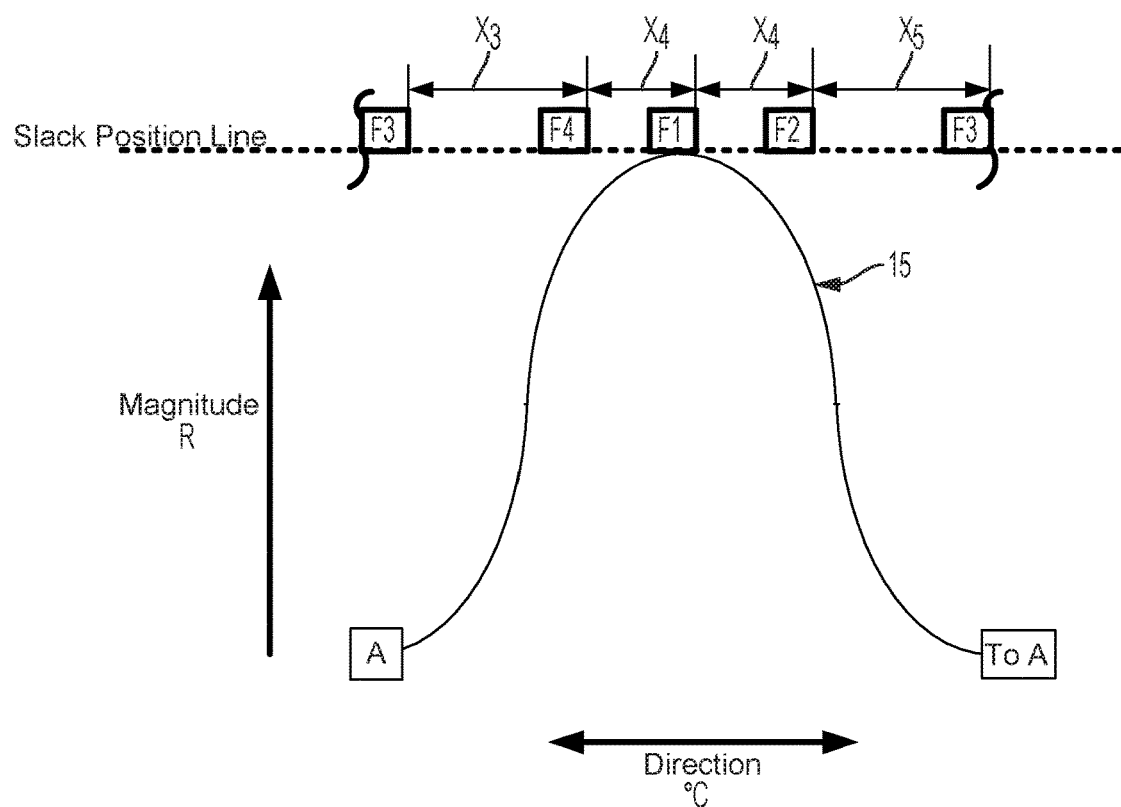

FIGS. 18A and 18B graphically depict cam-follower system embodiments with variable spacing between followers. FIG. 18A depicts an embodiment with four followers, F1, F2, F3, and F4, spaced evenly (by distance $X_1$) around a circumference that is centered on a longitudinal axis of a control handle in which the cam-follower system is housed. FIG. 18B depicts an embodiment with four followers, F1, F2, F3, and F4, that are not evenly spaced (by distances $X_3$, $X_4$, and $X_5$) around a circumference that is centered on a longitudinal axis of a control handle in which the cam-follower system is housed. As noted above, alternate spacing of followers can be used to mitigate problems of "drift" or can be configured to provide a desired balance between fine control of the flex angles and a minimal amount of control adjustment that is necessary to adjust the flex angles and magnitude in different directions. For example, narrower spacing of the followers results in less change in radial flex per adjustment of the flex magnitude control, while larger spacing between followers provides less fine control of the exact magnitude of flex.

Figure 19:
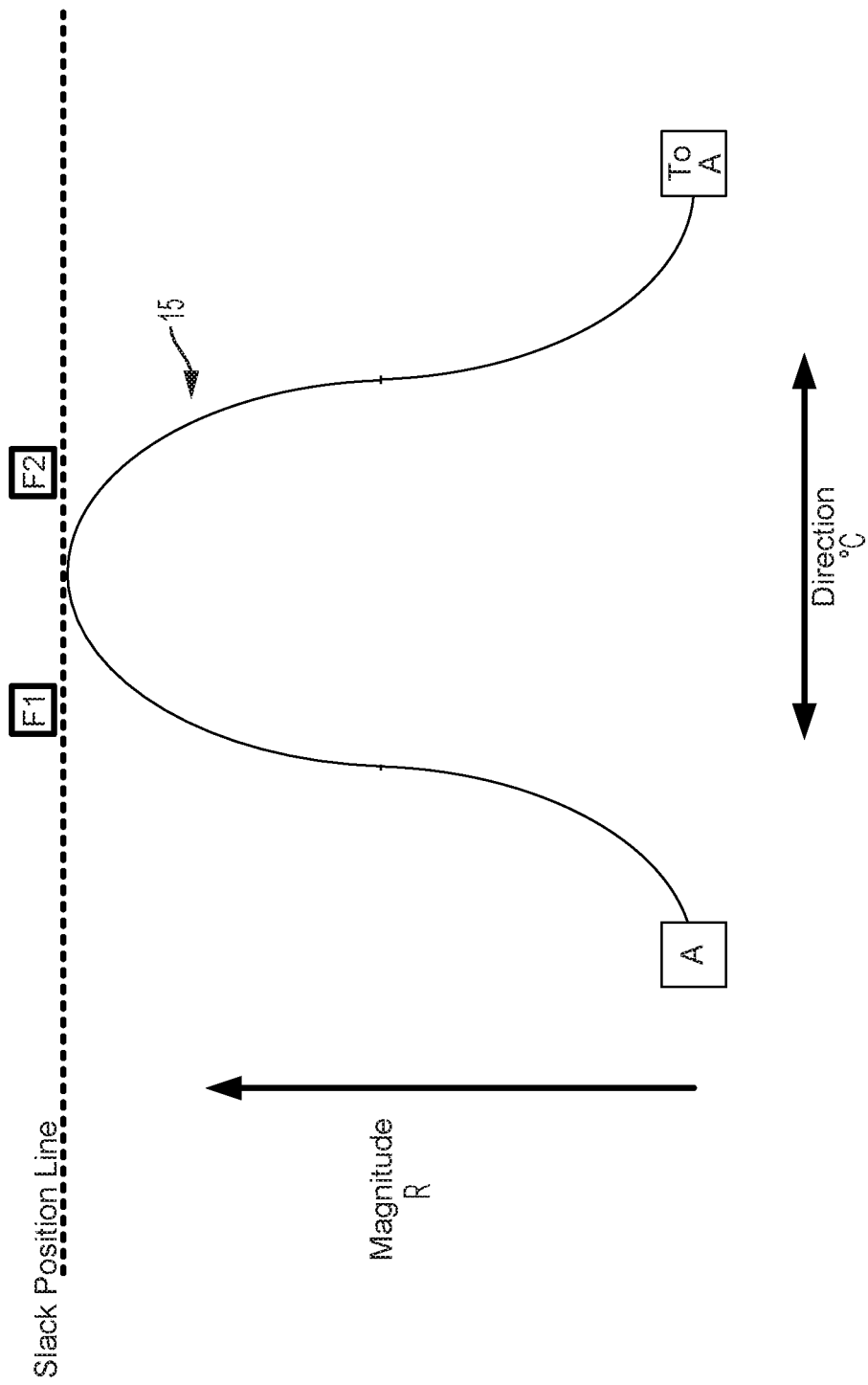
FIG. 19 illustrates an exemplary embodiment of a cam and follower arrangement with two cams.

Cam rotation can also be limited to help mitigate drift. FIG. 19 graphically depicts a cam that can only be rotated through 90° with respect to a longitudinal axis of a housing of a control handle in which the cam resides. Followers F1 and F2 are spaced 45° apart or less circumferentially with respect to the longitudinal axis within the cam's range of rotation. Accordingly, the cam follower contact surface will always be in contact with at least one follower F1 or F2 when the cam is axially advanced beyond the Slack Line Position.

Figure 20A:
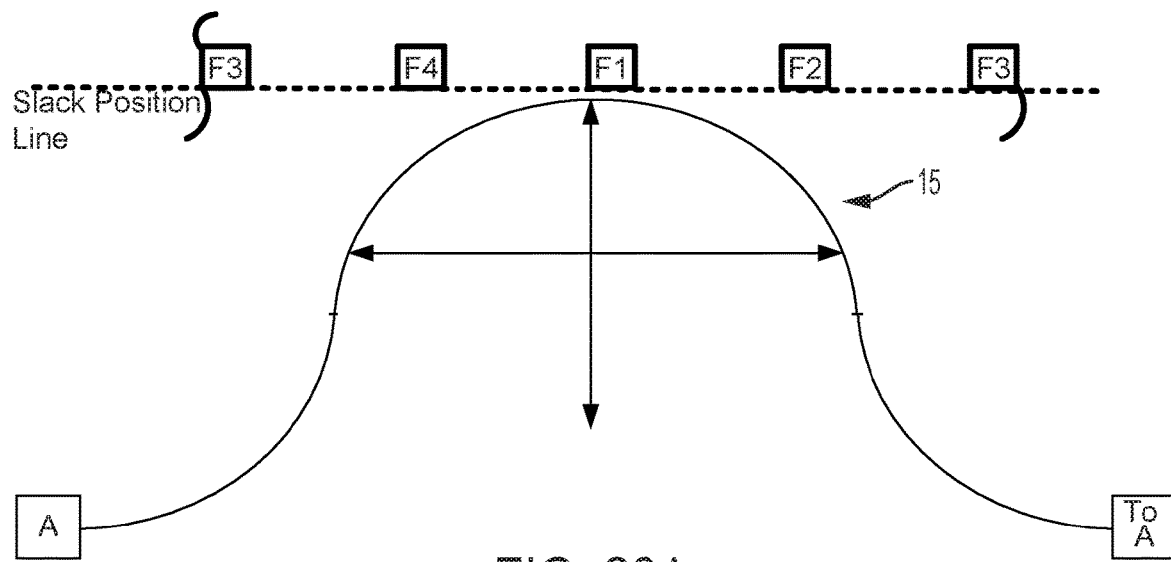
FIGS. 20A and 20B illustrate an exemplary embodiment of a cam and follower arrangement where the cam is adjustable in size.
Figure 20B:
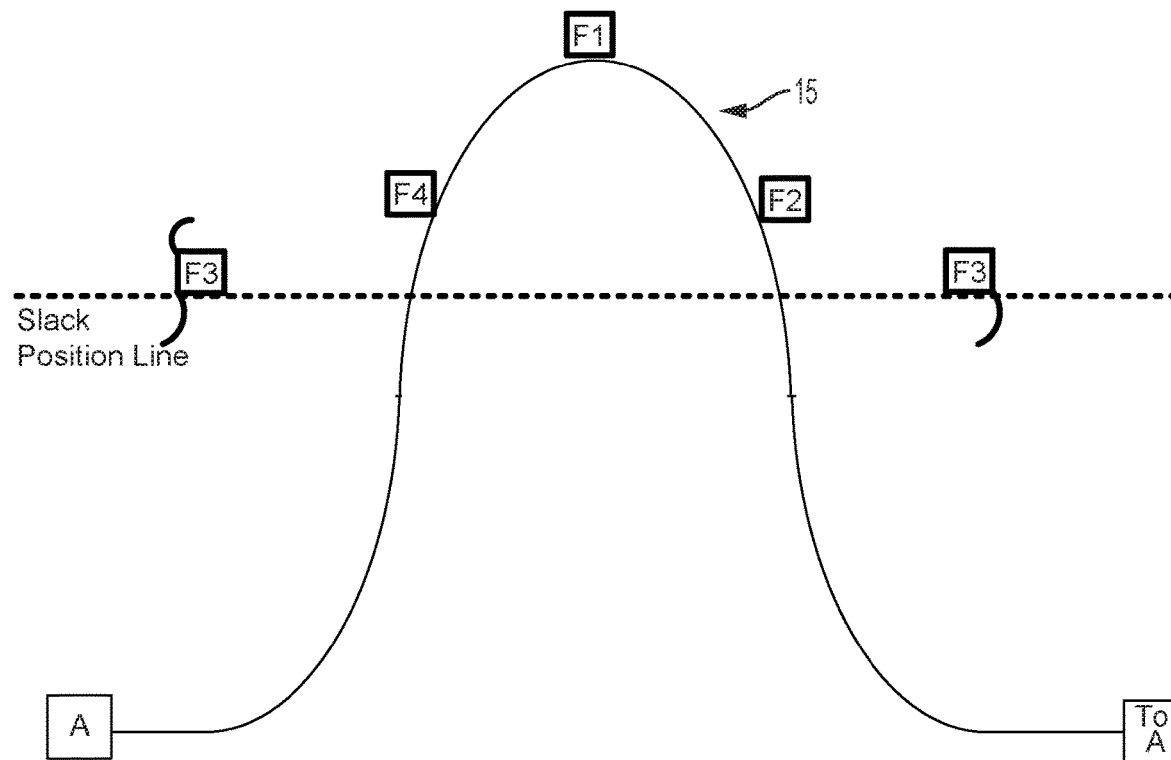

As shown in FIGS. 20A and 20B, in disclosed embodiments, the cam contact surface 15 can change size and shape as a function of axial displacement. In certain disclosed embodiments, the cam is a ribbon cam, made of metal, polymer, or other suitable material that is globally flexible, but maintains local rigidity for interaction with the cam followers. FIG. 20B shows a graphical depiction of a cam that becomes increasingly narrow and increasingly steep as it advances axially from its position in FIG. 20A to its position in 20B. Such a cam follower contact surface 15 has the advantage that it can provide finer control than a uniformly wider cam contact surface by engaging less followers when at a greater magnitude while maintaining the benefit of mitigated drift that comes with a cam with a shallower slope at lower magnitudes.

Figure 21:
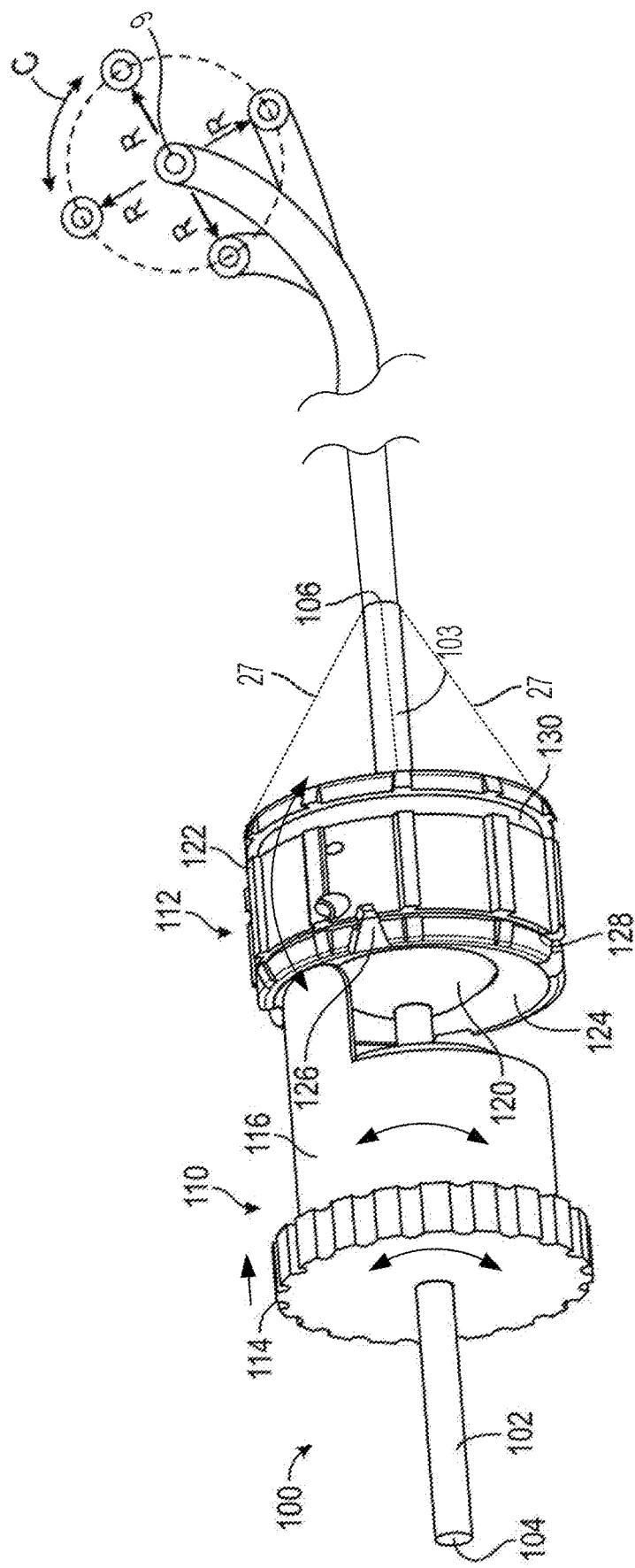
FIG. 21 is a perspective view of a ball-and-socket mechanism and projection operationally attached to a steerable catheter.
Figure 22:
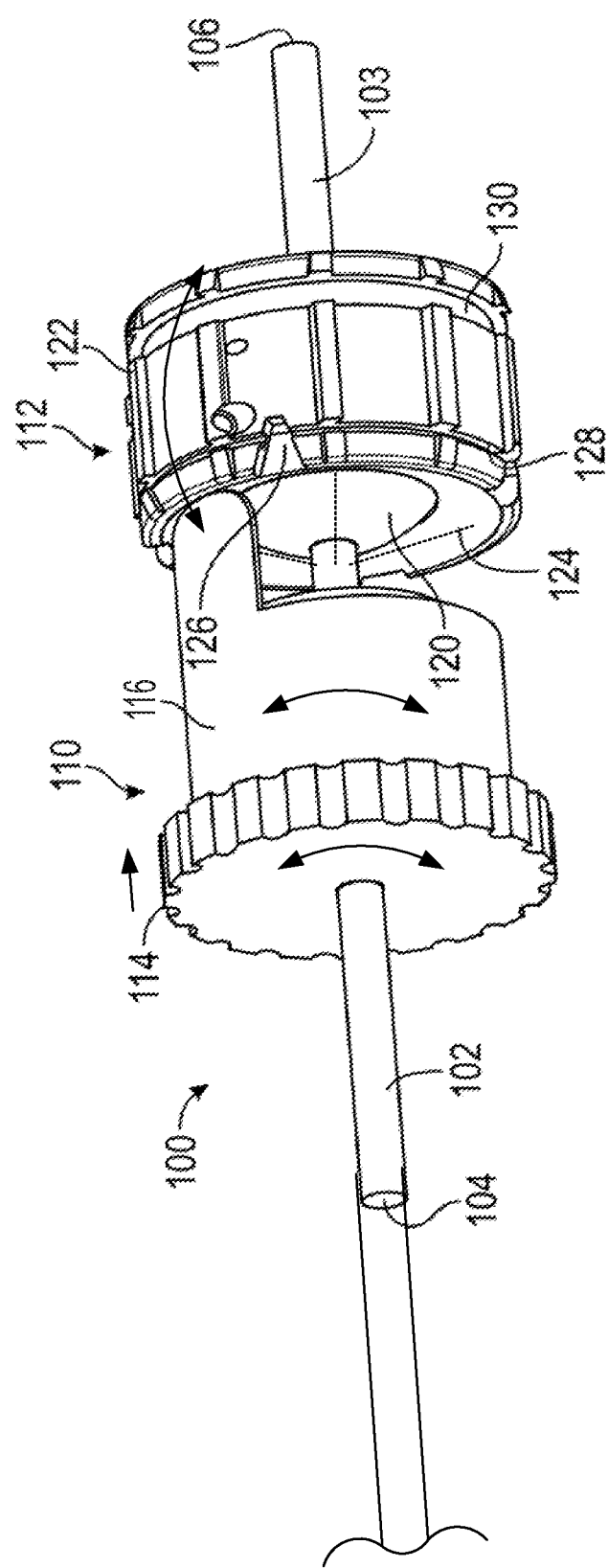
FIG. 22 is a perspective view of the ball-and-socket mechanism and projection of FIG. 21.

FIGS. 21-22 illustrate another exemplary control handle 5 comprising a projection 116 and a ball-and-socket mechanism wherein the socket is coupled to pull wires such that the orientation of the socket relative to the ball determines the tension in the pull wires and thus the position of an attached catheter. Embodiments disclosed herein can further comprise a central tubular shaft 102, 103 having a proximal end 104 and a distal end 106, a proximal component 110 fixed to the shaft, a socket 112, and a ball 120 mounted on the shaft inside the socket. The proximal component 110 includes a flex knob 114 and a projection 116 that contacts an engagement surface 124 of the socket 112. The rotational orientation of the socket 112 relative to the projection 116 (e.g., selected by rotating the socket) determines how the socket 112 tilts relative to the ball 120, which determines the circumferential angle toward which the distal tip of the catheter is directed. The axial position of the projection 116 relative to the socket 112 (e.g., selected by rotation of the flex knob 114) determines the magnitude of axial flex of the distal tip of the catheter. The socket 112 can have notches 126 and grooves 128, 130 around its outer perimeter. A plurality of guidewires can be coupled to the socket around its perimeter by the notches 126 and grooves 128, 130 and run distally into the catheter. However, the guidewires can be coupled to the socket in any manner.

The radius of the socket 112 can be increased to increase the maximum tension that can be applied to the pull wires (and thus the maximum flex magnitude of an attached catheter). Pull wires can further be coupled to socket 112 via rack and pinion or pulley assemblies. As discussed further below, such mechanisms provide mechanical advantage that magnifies the relative small motions of the projection 116 and socket 112 to provide the desired flex in the catheter. The mechanism system that couples the steering and flex knobs to the pull wires can be configured and/or calibrated to provide the desired balance of fine control and range of motion of catheter flex. The ball-and-socket mechanism provides an analog, full 360 degree range of adjustability for catheter flex, without needing to rotate the catheter inside the patient.

FIGS. 23-39 illustrate further embodiments of control handles 200 and 300 that include a projection that interfaces with a gimbal mechanism to control tension on pull wires that are coupled to an attached catheter. FIGS. 23-32 show handle 200, which comprises a housing 210 having a distal end 212 and a proximal inner cavity 214 that contains a gimbal mechanism comprising an outer gimbal ring 216 and an inner gimbal plate 218. The ring 216 is pivotably mounted relative to the housing 210 at pivot joints 250 so that the ring can rotate relative to the housing about a ring axis passing through joints 250 perpendicular to the longitudinal axis of the handle. The plate 218 is pivotably mounted relative to the ring 216 at pivot points 252 such that the plate can rotate relative to the ring about a plate axis passing through joints 252 perpendicular to the ring axis. The plate axis and ring axis are rotationally fixed about the housing axis, but the plate can pivot multidirectionally relative to the housing as the ring pivots relative to the housing through joints 250 and as the plate pivots relative to the ring through joints 252.

Figure 23:
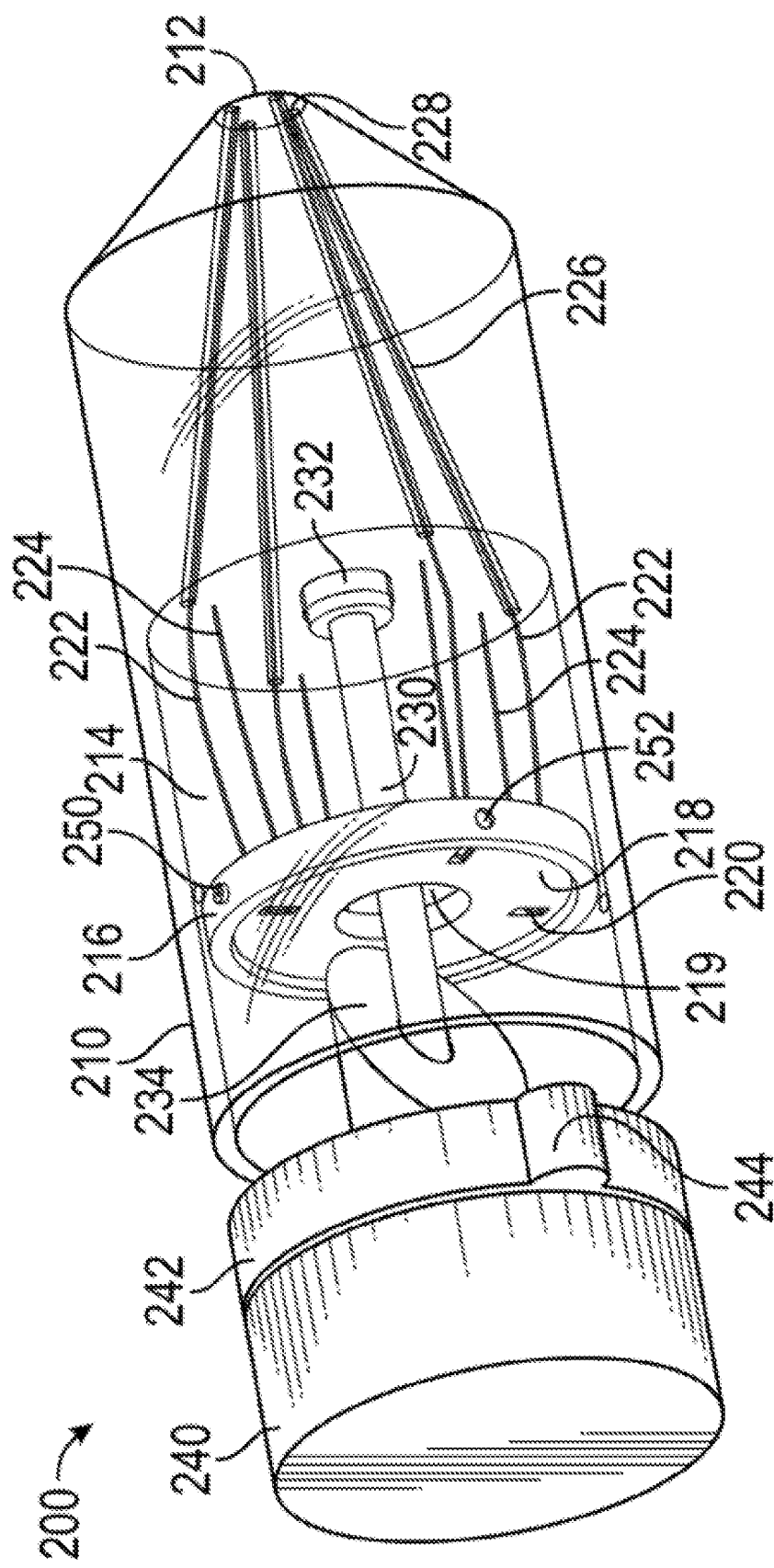
FIG. 23 shows a perspective view of an exemplary multi-direction control handle with a cam-and-gimbal mechanism for controlling pull wires for a steerable catheter assembly.
Figure 24:
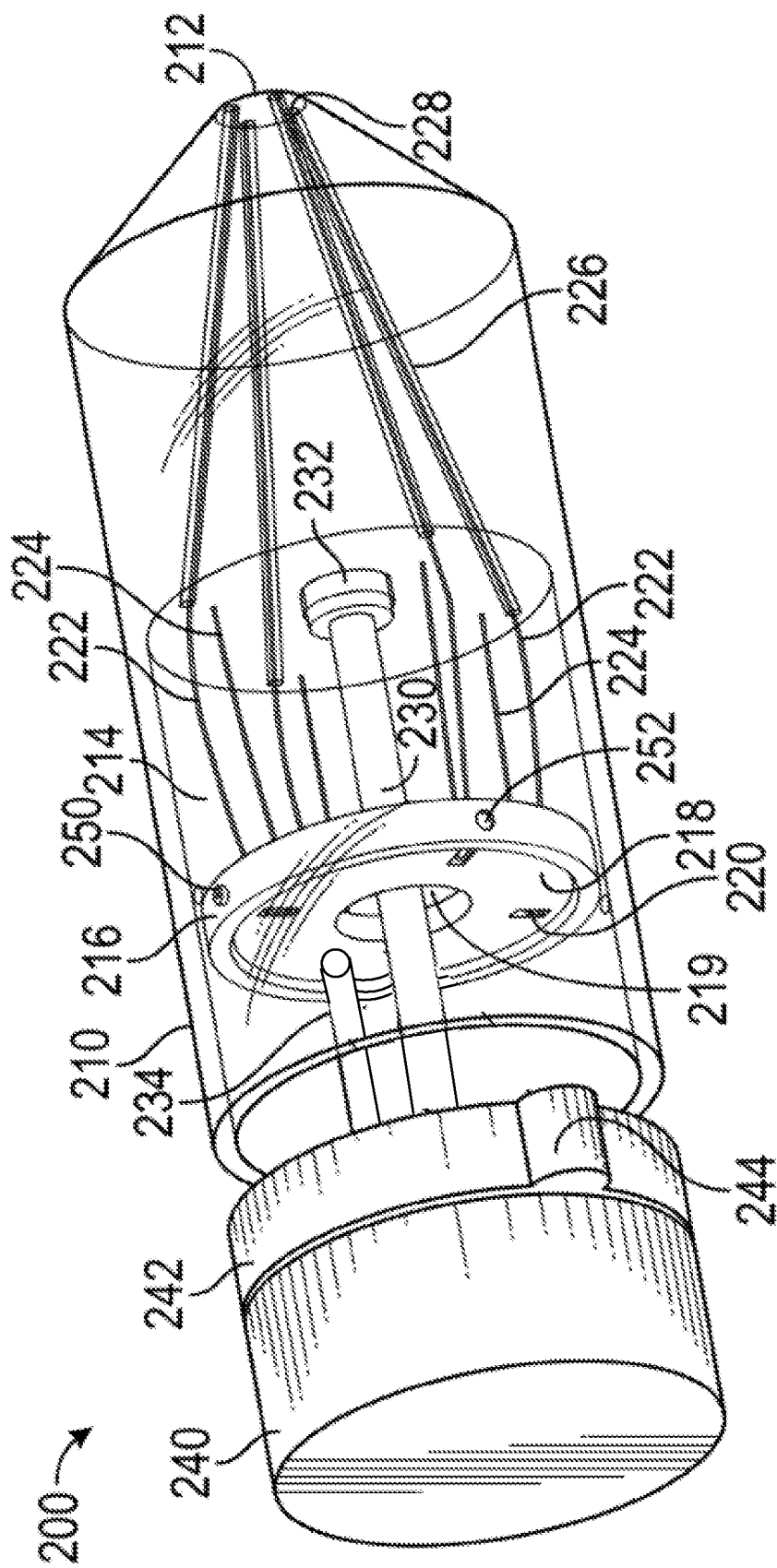
FIG. 24 shows a perspective view of an exemplary multi-direction control handle with a projection-and-gimbal mechanism for controlling pull wires for a steerable catheter assembly.
Figure 25:
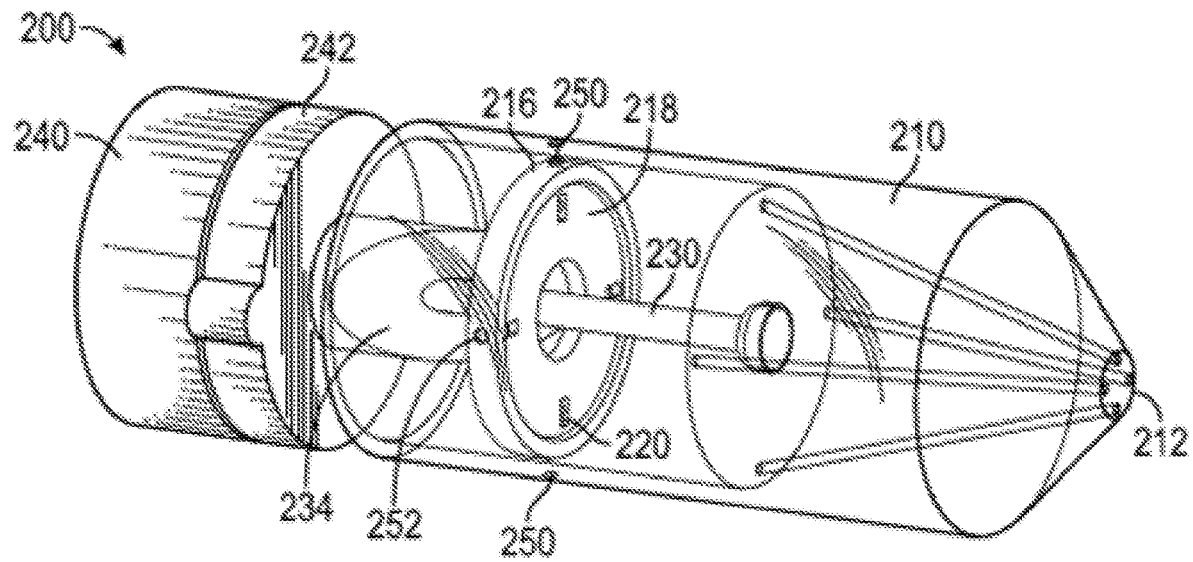
FIGS. 25-27 show perspective views of the exemplary multi-direction control handle with a cam-and-gimbal mechanism of FIG. 23 in various positions and without pull wires, for illustrative purposes.
Figure 26:
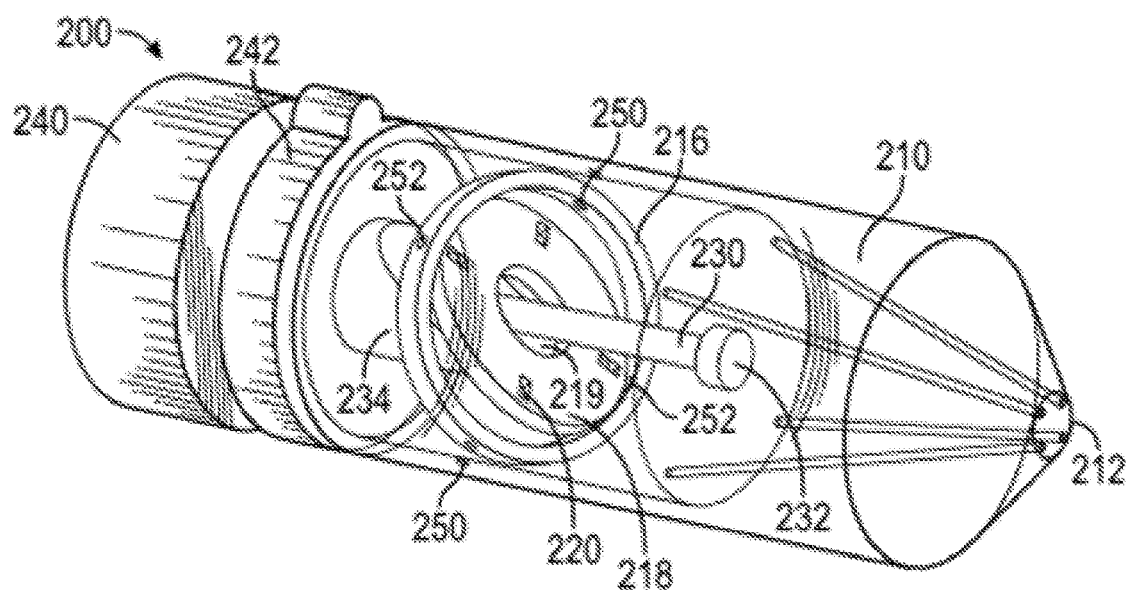

Control handle 200 further comprises two or more pull wires 222. The gimbal plate 218 can include wire engagements 220 for each pull wire 222 of the handle. Four pull wires 222 are illustrated as an example in FIGS. 23-32. Each wire 222 passes through passageways 226 in the handle and extends out from distal openings 228 into an attached catheter or other similar steerable device. The wires 222 can optionally loop around respective wire engagements 220 in the gimbal plate 218, as illustrated in FIGS. 23 and 24, such that end portions 224 of the wires extend back to fixed attachment points on the housing. In such embodiments, the wire engagements 220 can comprise a rounded peg, pulley, or other feature to facilitate the wires sliding around the wire engagement with minimal friction and kinking as the plate articulates. This arrangement can provide mechanical advantage, effectively halving the pulling force applied to the wires while causing the distal ends of the wires in the catheter to move at twice the rate that the wire engagements in the plate move. In alternative embodiments, the wires can terminate at the wire engagements 220 in the gimbal plate without any mechanical advantage, which can avoid bending the wires.

In embodiments disclosed herein, the handle 200 includes a central shaft 230 that has a distal end 232 coupled to the housing 210, an intermediate portion that passes through an opening 219 in the gimbal plate 218 and through projection 234, and a proximal portion that is fixedly coupled to a flex knob 240. The distal end 232 is coupled to the housing via a rotational bearing that allows rotation of the shaft 230 and flex knob 240 relative to the housing and gimbal mechanism, but prevents longitudinal motion of the shaft 230 and flex knob 240 relative to the housing and gimbal mechanism. Although not shown, the central shaft 230 and flex knob 240 can include a central lumen extending through their entire length. The housing 210 can also include a central lumen that extends from the distal end of the shaft 230 to the distal end 212 of the handle. Combined, the central lumens of the handle 200 can provide access for other devices and/or fluids to be passed into and out of a patient through the handle and through a connecting lumen in an attached catheter. Projection 234 can be a cam as pictured in FIG. 23 or other projection such as a projection comprising a pin or a pin with a ball rollably attached at a distal end of the pin such that the ball rolls on gimbal plate 218 as depicted in FIG. 24.

Figure 27:
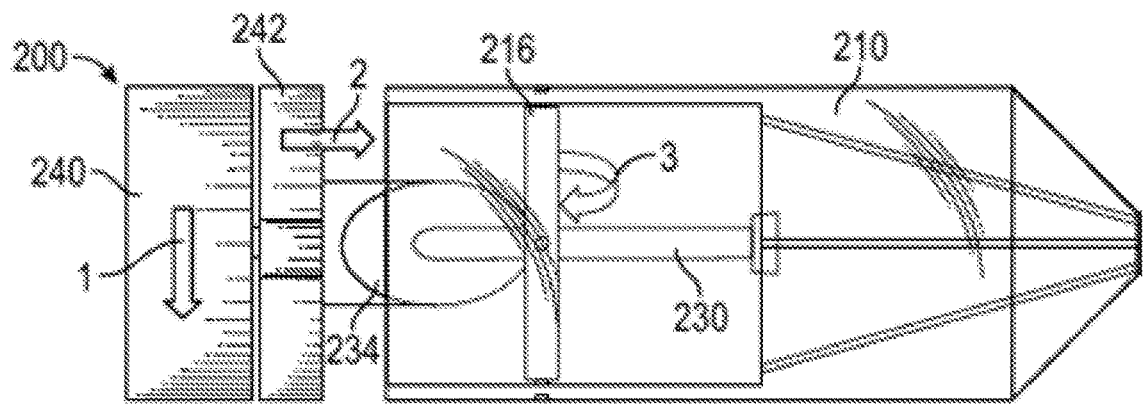
Figure 28:
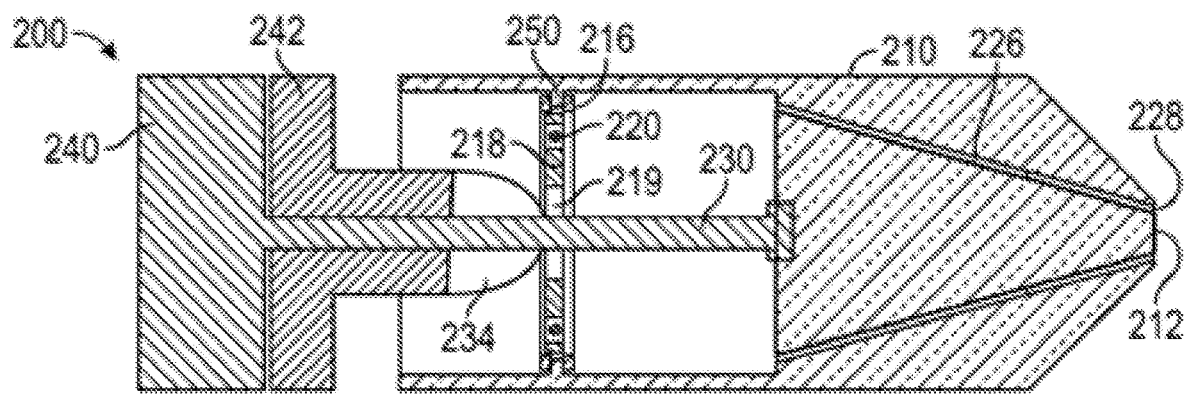
FIGS. 28-29 show cross-sectional views of the exemplary multi-direction control handle with a cam-and-gimbal mechanism of FIG. 23 without pull wires for illustrative purposes.
Figure 29:
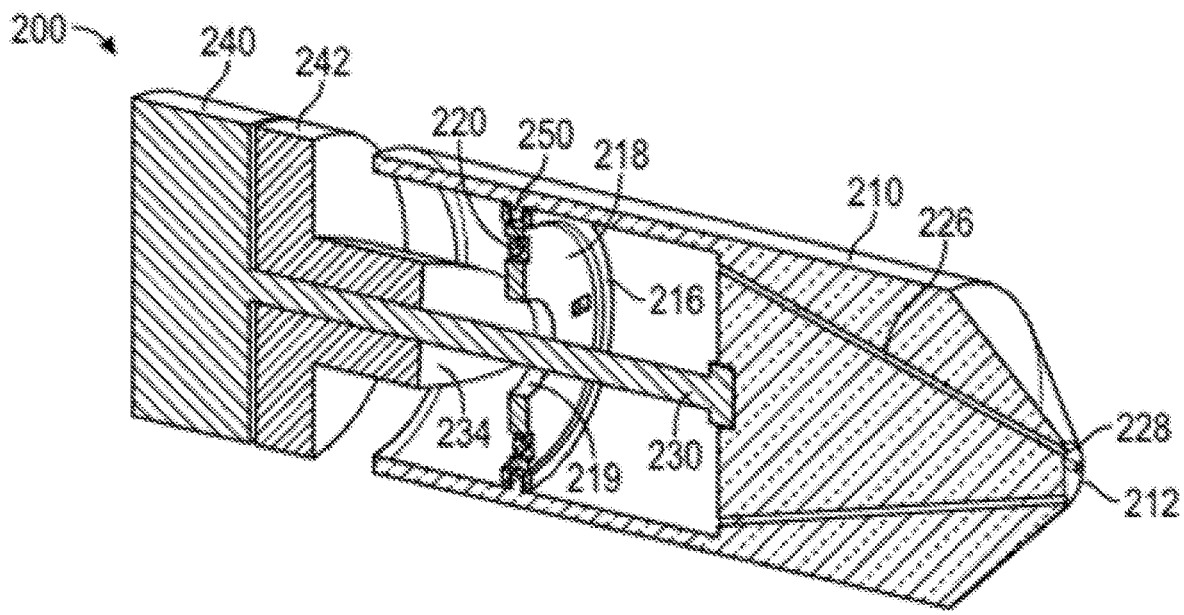

The handle 200 also includes a steering knob 242 that can include an indicator nub 244 that is fixedly coupled to the projection 234 and positioned around the central shaft 230 distal to the flex knob 240 in FIGS. 23-32. The projection 234 and/or steering knob 242 can be threadedly or helically engaged to the outer surface of the central shaft 230. As illustrated in FIG. 27, when the flex knob 240 and central shaft 230 are rotated (arrow 1) relative to the steering knob 242 and cam member 234 (e.g., by holding the steering knob stationary relative to the housing 210 and turning the flex knob relative to the housing 210), the steering knob and cam member are driven distally (arrow 2) or proximally relative to the housing and gimbal mechanism, causing the gimbal plate to pivot (arrow 3) and change tension on all the pull wires.

By using the flex knob 240 to drive the cam member distally or proximally, the magnitude of the flex of the catheter is adjusted. Distal motion of the cam causes the gimbal plate to tilt more, causing increased magnitude of flex, and proximal motion of the cam member allows the gimbal plate to return closer to its natural position perpendicular to the longitudinal axis of the handle, reducing the flex of the catheter. Rotating the flex knob 240 causes the catheter to flex in the circumferential direction (with respect to the longitudinal axis defined by the handle 200) determined by the position of the gimbal as a result of the rotation of the projection 234 about the longitudinal axis defined by the handle 200. The circumferential angle in which the catheter flexes is determined by the position of the steering knob 244, which rotates the projection with respect to the gimbal plate 218.

Figure 30:
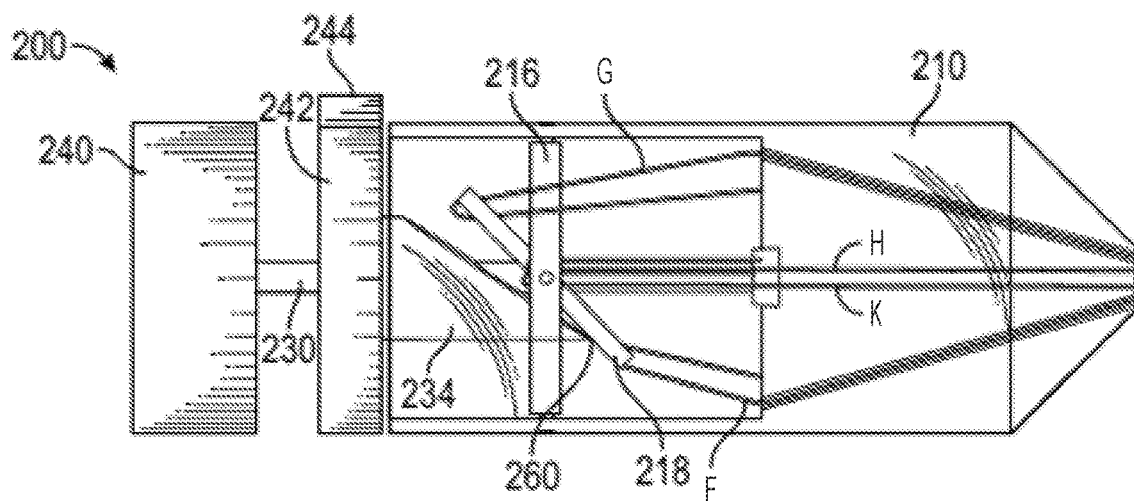
FIGS. 30-32 show perspective views of an exemplary multi-direction control handle with a cam-and-gimbal mechanism for controlling pull wires, wherein the pull wires are doubled back to provide a mechanical advantage in the pull wires.
Figure 31:
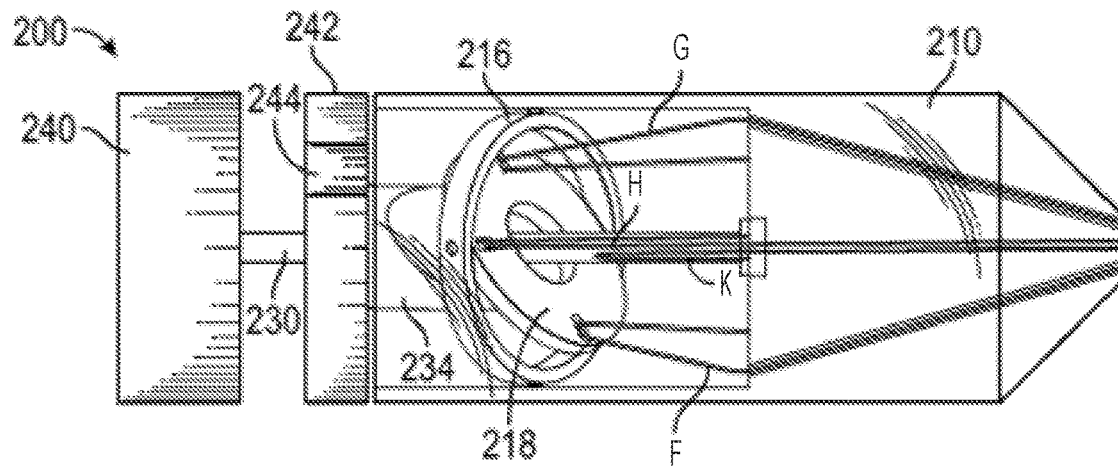
Figure 32:
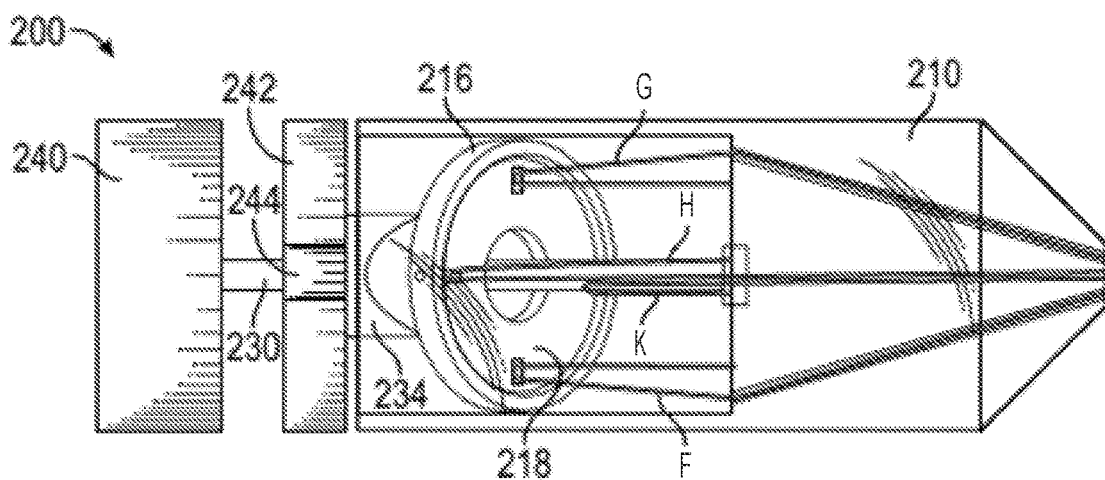
Figure 33:
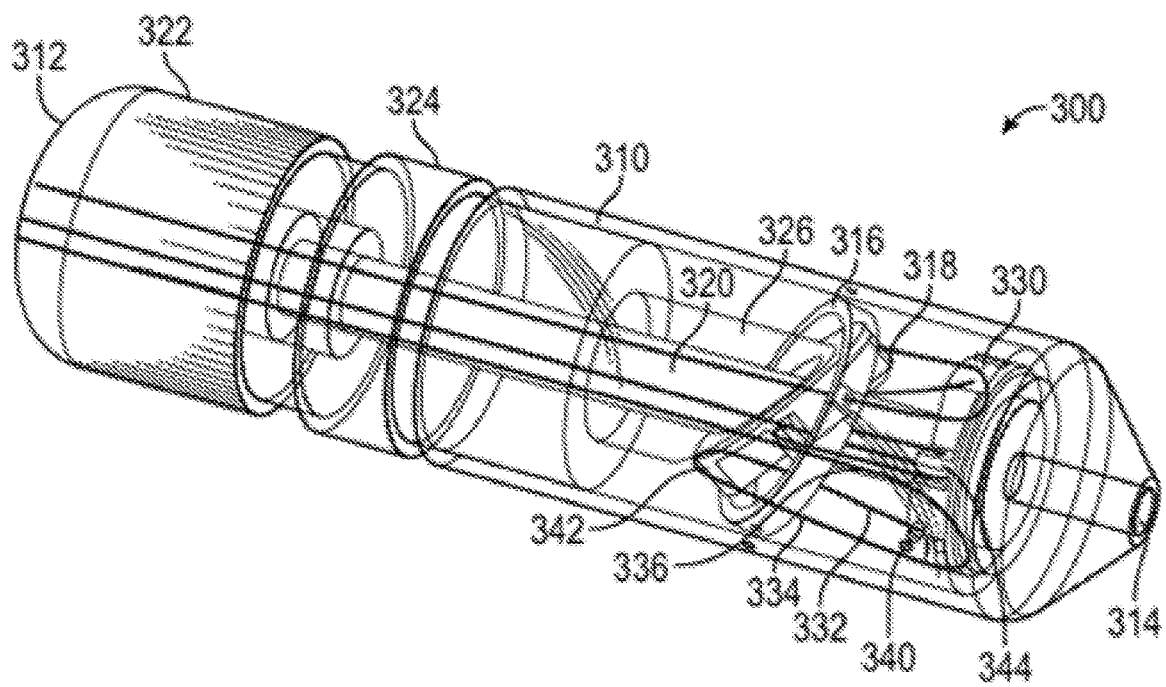
FIG. 33 shows a perspective view of an additional exemplary multi-direction control handle with a cam-and-gimbal mechanism for controlling pull wires, wherein the pull wires are doubled back to provide a mechanical advantage and a change of direction of the pull wires.
Figure 34:
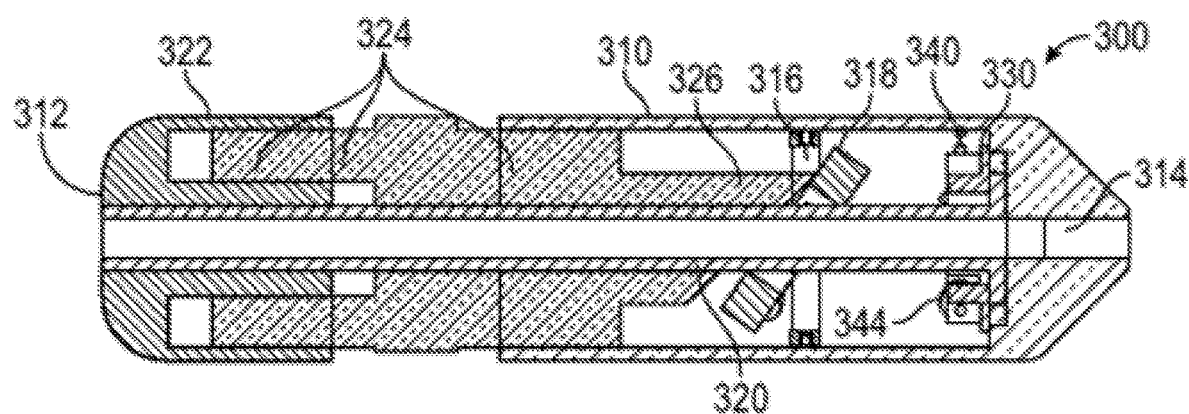
FIG. 34 shows a cross-sectional view of the multi-direction control handle of FIG. 33.

FIGS. 30-32 illustrate rotation of the steering knob 242 to change the circumferential angle at which the catheter radially flexes. The rotational position of the steering knob 242 can be visually and/or tactilely indicated by the nub 244 or other indicator. The steering knob 242 and the attached projection 234 can be rotated 360 degrees relative to the gimbal mechanism about the central shaft. The rotational position of the steering knob determines where a distal end of the projection 234 contacts the gimbal plate 218, and thus the direction in which the gimbal plate tilts when the flex knob 240 is used to drive the projection 234 into the gimbal plate 218.

The gimbal ring 216 and gimbal plate 218 work together to allow the plate to tilt in any direction, and thus flex the attached catheter in any radial direction. In FIG. 30, the ring 216 is stationary and the plate 218 tilts about the plate axis, pulling on wire G and relaxing wire F. This causes the catheter to flex in the direction of the wire G. In FIG. 31, the ring 218 rotates about the ring axis and the plate 216 rotates about the plate axis, pulling both wires G and H, and relaxing wires F and K. This causes the catheter to flex in a direction between wires G and H. In FIG. 12, the plate 218 is stationary relative to the ring 216, and the ring and plate rotate in unison about the ring axis, pulling on wire H and relaxing wire K. This causes the catheter to flex in the direction of the wire H.

In some embodiments, the gimbal plate can have a non-planar contact surface, with bump(s) and/or valley(s) which vary in height circumferentially and/or radially on the gimbal plate. These can compensate for any discretization effect of not using an infinite number of pull wires around the perimeter of the plate. For example, when the cam member pushes on the gimbal plate between two wires, it may need a little extra pull on the pull wires in order to get the same amount of flex at the distal end of the catheter. These bumps or valleys can achieve that extra pull by tilting the plate a little more or less at certain circumferential and radial cam contact locations. For example, if a completely planar gimbal plate is used, a slight unflexing may occur when the steering knob is adjusted such that the flex direction is between two of the pull wires. Including a gradual bump on the gimbal plate in the location between the pull wire engagements (as just one example) can compensate for that expected unflexing by tilting the gimbal plate a little more when the cam contacts that bump, thereby providing the additional pull wire motion needed to maintain a constant flex magnitude in a direction between two pull wires.

FIGS. 33-39 illustrate embodiments of control handle 300, which includes a projection that interfaces with a gimbal mechanism to control tension on at least two pull wires. The control handle 300 functions in a similar manner to the control handle 200, with the major difference being the catheter is connected to the opposite longitudinal end of the handle and the pull wires double back and extend out from the opposite longitudinal end of the handle, flipping the distal and proximal directions compared to the handle 200.

The handle 300 comprises a housing 310, a proximal end 314, and a distal end 312 at or near flex knob 322. The flex knob 322 is axially fixed relative to a central shaft 320, and a steering knob 324 is positioned around and/or within the flex knob in a threaded engagement or helical interface such that rotation of the flex knob drives the steering knob and projection 326 axially relative to the gimbal mechanism inside the housing. The gimbal mechanism includes a gimbal ring 316 pivotably mounted inside the housing about a ring axis and a gimbal plate 318 pivotably mounted inside the ring via pivots along a plate axis perpendicular to the ring axis, like with the handle 200. The handle 300 can also include a wire guide plate 330 mounted inside the housing 310 proximal to the gimbal mechanism.

Each pull wire in the handle 300 can have an end 340 fixed to wire guide plate 330, a first portion extending from the wire end 340 distally to the gimbal plate 318 and around pulleys or other guides 342 in the gimbal plate, a second portion that extends back proximally from the gimbal plate to secondary pulleys or guides 344 in the wire guide plate 330, then around the pulleys or guides 344, and a third portion that extends distally through the central shaft 320 along the length of the handle and out through the distal end 312 of the handle into a catheter coupled to the handle.

Figure 35:
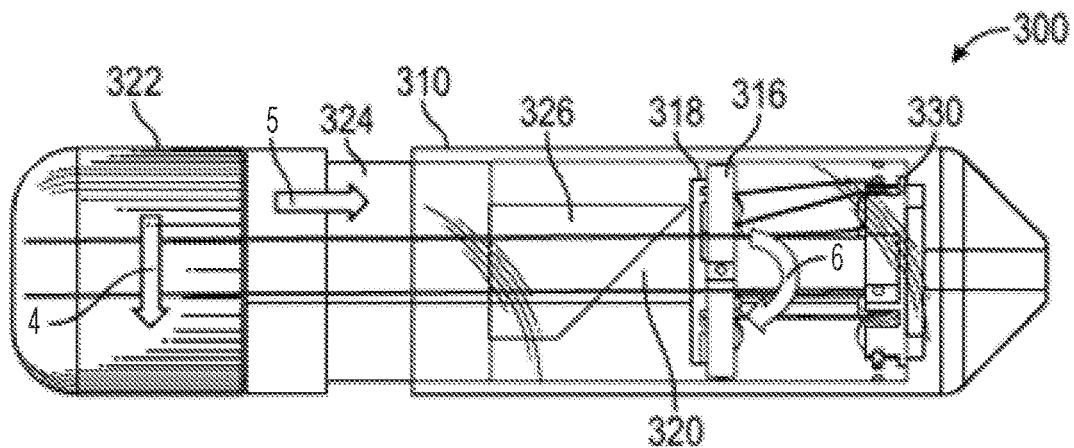
FIGS. 35-39 illustrate operation of a multi-direction control handle.

FIG. 35 illustrates how rotating the flex knob 322 (arrow 4) causes the projection 326 to move axially (arrow 5), and causes the distal edge of the projection 326 to tilt the gimbal plate 318 and/or ring 316 (arrow 6), which adjusts the magnitude of flex in the attached catheter.

Figure 36:
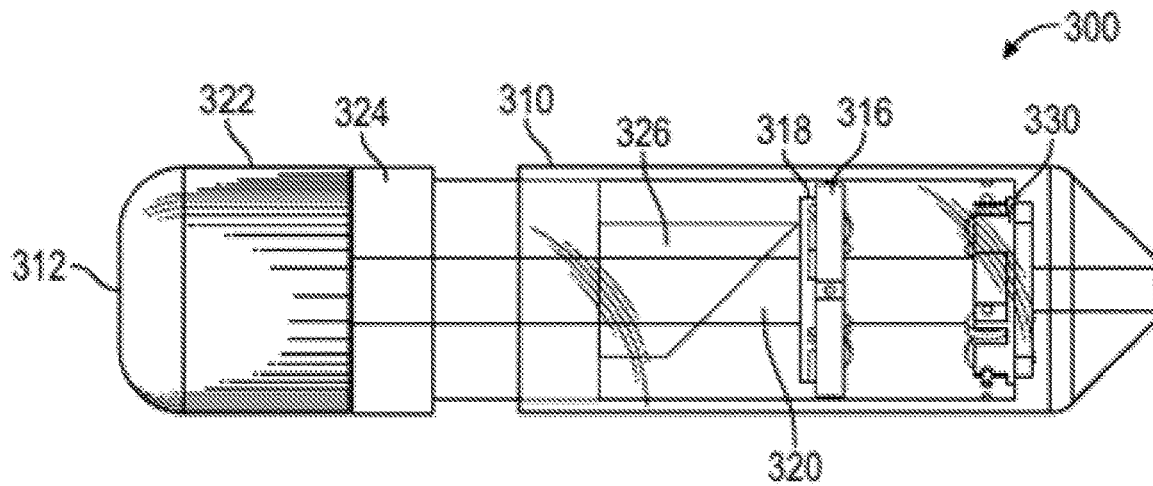
Figure 37:
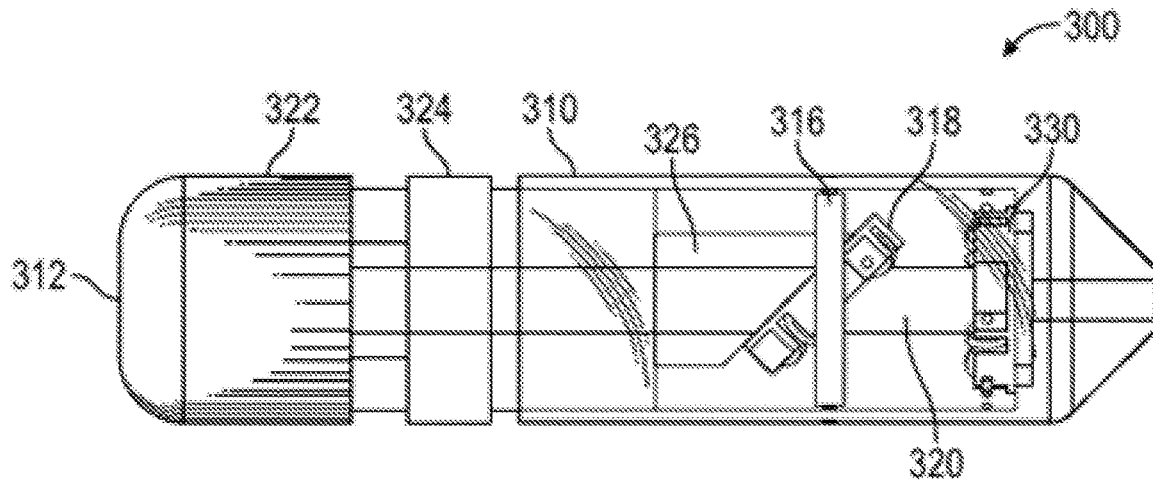
Figure 38:
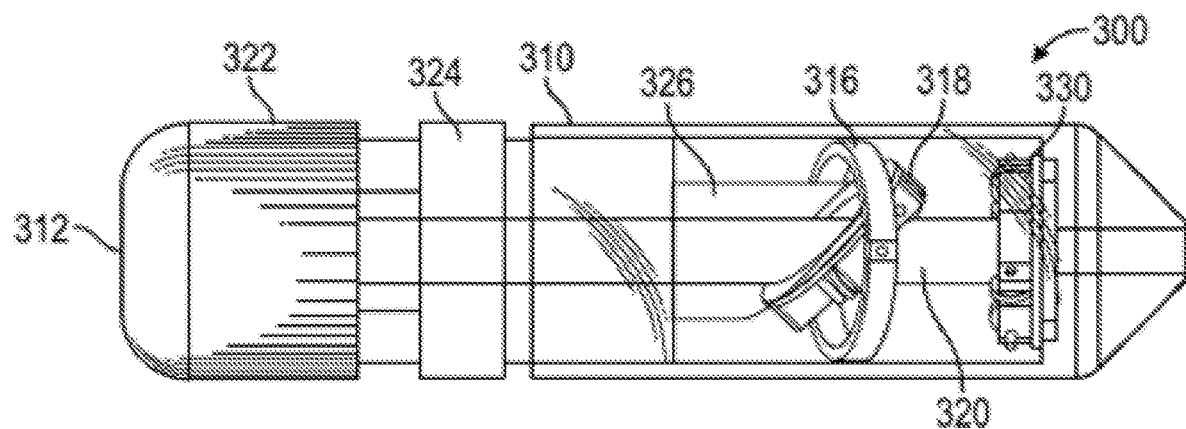
Figure 39:
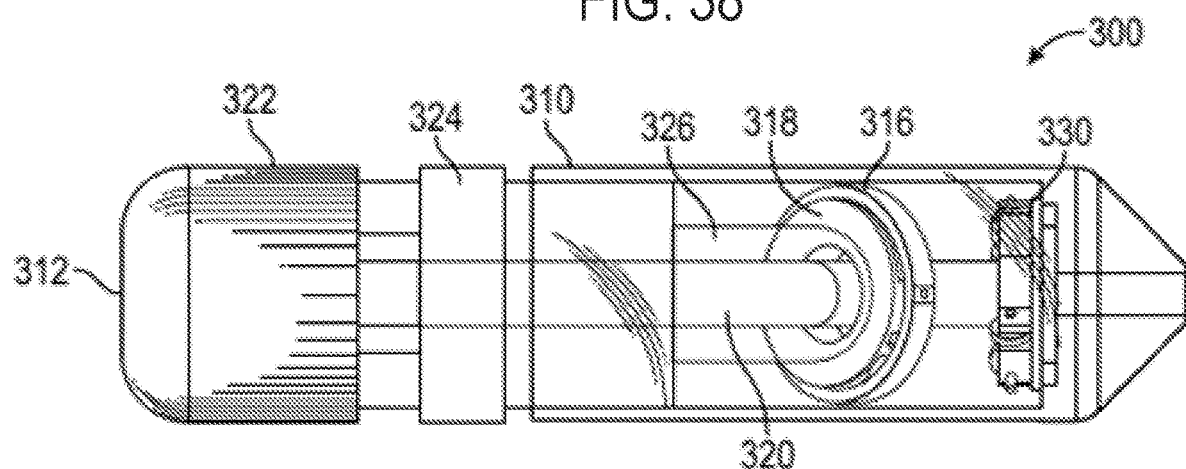

FIG. 36 shows the handle 300 with the gimbal ring 316 and plate 318 in a relaxed position when the projection is not tilting ring 316 or plate 318. In this state, the attached catheter can be in a relaxed, non-flexed neutral position. FIG. 37 shows the projection 326 advanced proximally, tilting the gimbal plate 318 while the gimbal ring 316 remains stationary. This causes flex of the attached catheter in a selected radial direction. FIG. 38 shows the projection 326 rotated a few degrees from its position in FIG. 37, such that both the gimbal plate and ring are pivoted. This causes the attached catheter to be flexed about the same magnitude but in a correspondingly different radial direction compared to the flex magnitude in FIG. 37. In FIG. 39, the projection 326 is rotated about 90 degrees from its position in FIG. 37, such that the gimbal ring is pivoted relative to the housing 310, but the gimbal plate is not pivoted relative to the gimbal ring. In this position, the attached catheter is flexed about the same radial amount as in FIGS. 37 and 38, but it is flexed in a direction that is about 90 degrees from the direction corresponding with the catheter position in FIG. 37.

As the gimbal plate 318 moves relative to the wire guide plate 330, the pull wires articulate around the wire guides 342 and 344 in the two plates, providing a mechanical advantage that magnifies the relative small motions of the cam member and gimbal plate to provide the desired flex in the catheter. Like with the handle 200, the mechanism that couples the knobs 322 and 324 to the pull wires can be configured and/or calibrated to provide the desired balance of fine control and range of motion of catheter flex. The gimbal mechanism of control handle 300 also provides an analog, full 360 degree range of adjustability for the catheter flex, without needing to rotate the catheter inside the patient. Further, as with the gimbal plate 218 of control handle 200, the radius of gimbal plate 318 can be increased to increase the maximum tension that can be applied to the pull wires (and thus the maximum flex magnitude of an attached catheter).

Figure 40:
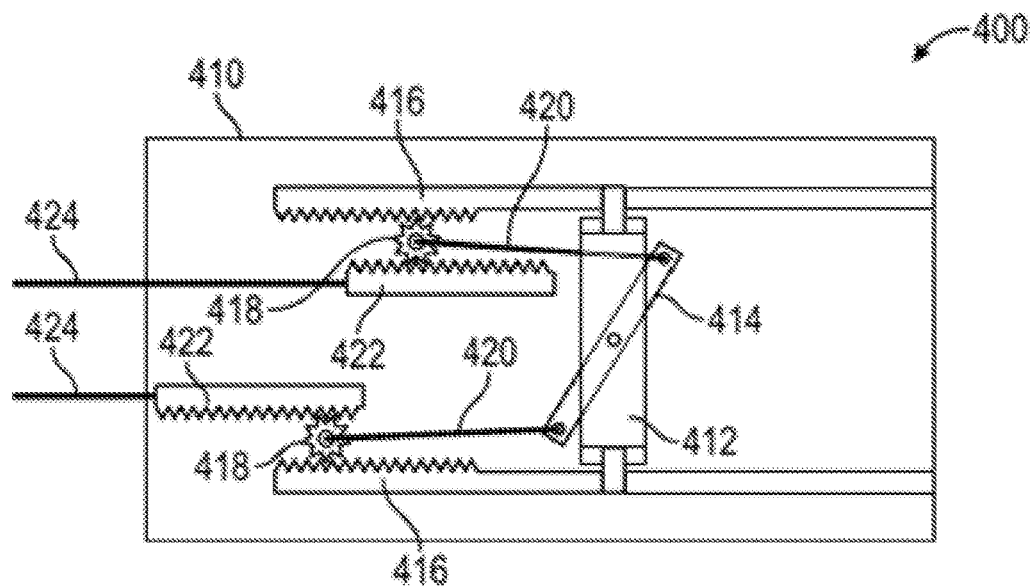
FIG. 40 shows a side view of an exemplary embodiment of a gear rack and pinion assembly that couples pull wires and a gimbal assembly.

FIG. 40 is a schematic diagram that illustrates an alternative handle system 400 for coupling a gimbal mechanism to pull wires without looping or curling the pull wires. The system 400 includes a housing 410 with a gimbal ring 412 and gimbal plate 414 mounted inside the housing, fixed rack gears 416 mounted in fixed relationship to the housing, moving rack gears 422 opposing each fixed rack gear 416 and coupled to the pull wires 424, rolling pinion gears 418 engaged between the fixed and moving rack gears, and rigid connector members 420 coupled from the gimbal plate 414 to the center of each pinon gear 418. A projection (not shown) causes motion of the gimbal mechanism, which pulls and pushes on the rigid connector members 420, causing the pinion gears 418 to roll correspondingly along the fixed rack gears 416. For each unit of distance the pinion gears 418 roll, the moving rack gears 422 move in the same direction but twice as far, creating mechanical advantage that magnifies the motion of the projection into greater motion of the pull wires, but without pulleys or other devices that require the pull wires to be curled or bent around sharp angles, which can damage the wires over time. While this embodiment describes a rack and pinion assembly that is particular to a gimbal mechanism-based control handle, the rack and pinion assembly can similarly be implemented in any of the other embodiments described herein by coupling followers to pull wires using a rack and pinion assembly.

Figure 41:
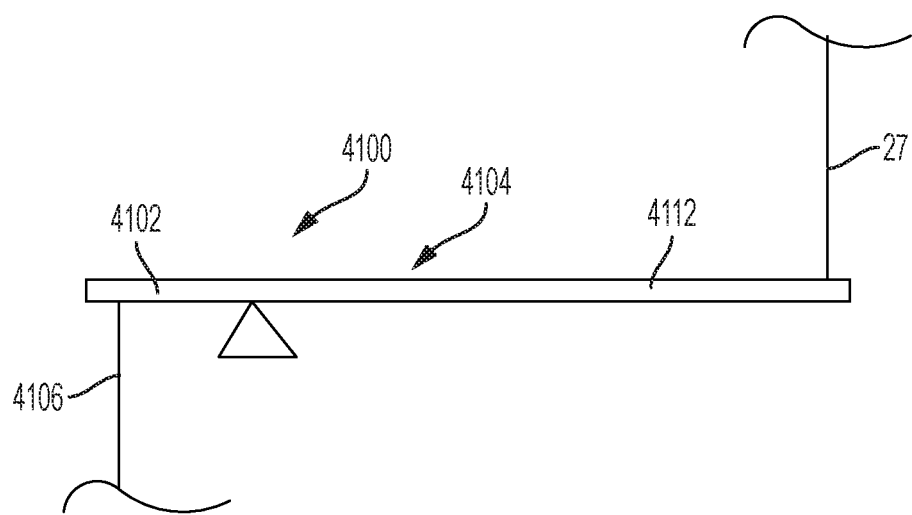
FIG. 41 shows a side view of a lever device that can provide mechanical advantage in increasing tension in catheter pull wires.
Figure 42:
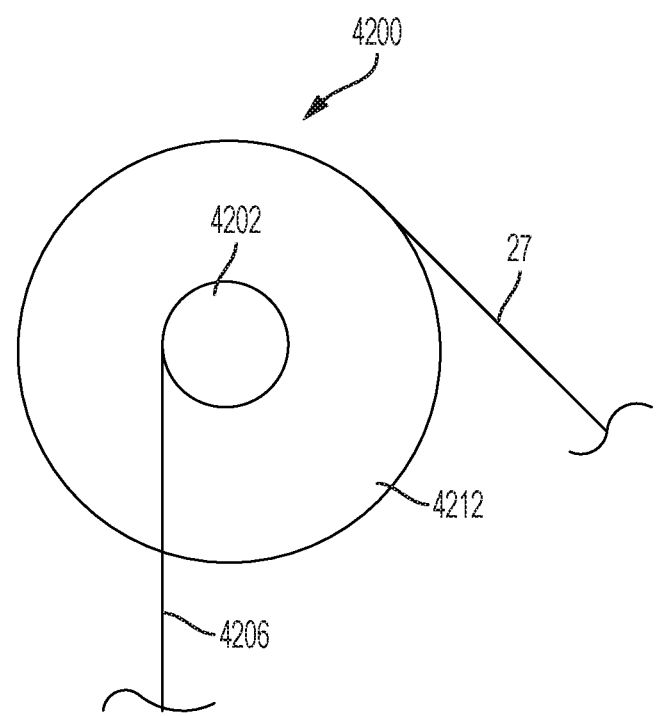
FIG. 42 shows a side view of a pulley device that can provide mechanical advantage in increasing tension in catheter pull wires.

FIGS. 41 and 42 show side views of a lever assembly 4100 and a pulley assembly 4200, respectively. In FIG. 41, a short end 4102 of the lever arm 4104 is connected to a wire 4106 that is coupled to the handle mechanism. A long end 4112 of the lever arm is connected to a catheter pull wire 27. As such, the motion of the wire 4106 is multiplied in the pull wire 27 by the lever assembly. In FIG. 42, a small hub 4202 of the pulley assembly 4200 is connected to a wire 4206 that is coupled to the handle mechanism. A larger hub 4212 of the pulley assembly is connected to a catheter pull wire 27. As such, the motion of the wire 4206 by the handle mechanism is multiplied in the pull wire 27 by the pulley assembly 4200. These assemblies can similarly be implemented in any of the other embodiments described herein by coupling followers to pull wires using the assemblies to gain mechanical advantage to magnify relative small motions to provide the desired flex in the distal end of an attached catheter.

Figure 44A:
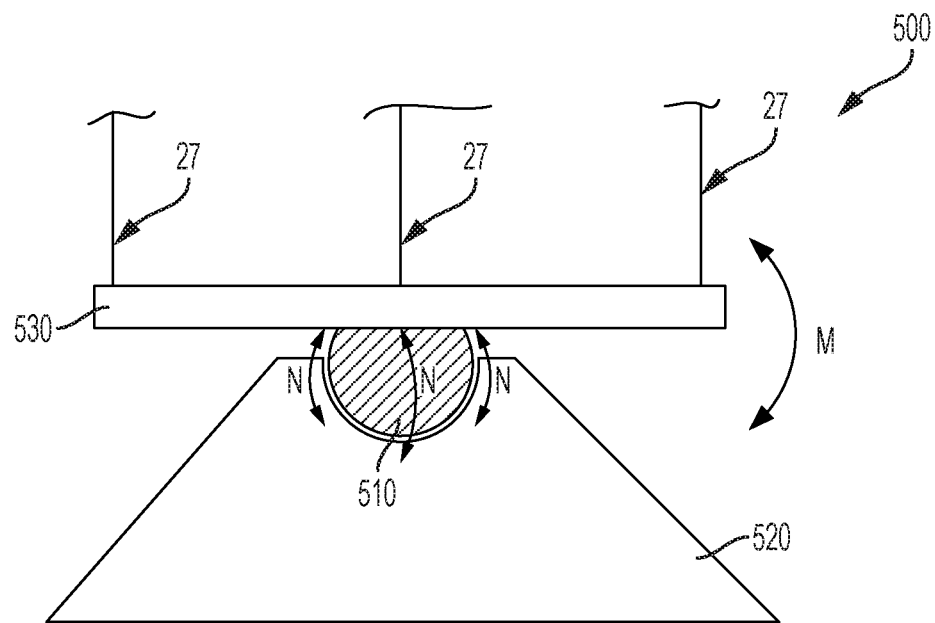
FIG. 44A is a side view of a plate with an attached ball in a fixed socket mechanism and pull wires for use in a steerable catheter assembly.
Figure 44B:
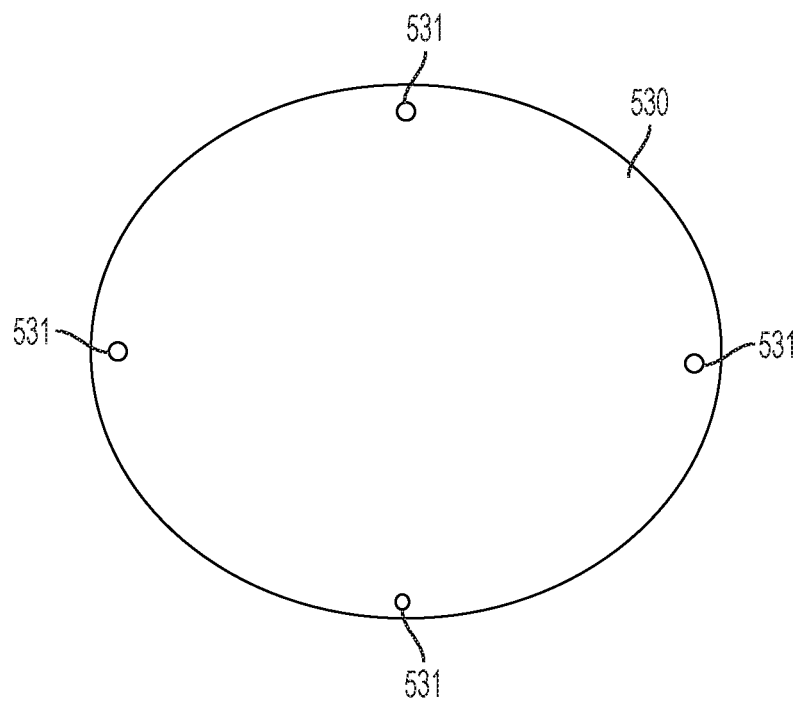
FIG. 44B is a top-down view of the plate shown in FIG. 44A.

FIG. 44A illustrates an embodiment of an assembly 500 that interfaces with a projection (not shown) to control tension on at least two pull wires 27. Assembly 500 is a plate 530 attached to a ball 510 that is rotatably mounted in a socket base 520. The socket base 520 is fixed to a housing of a control handle (not shown). The ball 510 rotates in the directions indicated by the arrows N, thus allowing the plate 530 to rotate and tilt in the directions indicated by arrows M and N. At least two pull wires 27 are attached to the plate 530 on one axial side of the plate 530. Though pull wires 27 are shown attached on the opposite axial side of the plate 530 as the side to which the ball 510 is attached, the pull wires 27 may be attached to the plate 530 on the same axial side as the ball 510, depending on the orientation of the socket base 520 and the pull wires 27 within the control handle housing. FIG. 44B illustrates the plate 530 from an axial side view. In the embodiment shown, holes 531 provide attachment points for the pull wires 27 in the plate 530. Further, as with the gimbal plate and ball-and-socket embodiments, the radius of the plate 530 can be increased to increase the maximum tension that can be applied to the pull wires 27 (and thus the maximum flex magnitude of an attached catheter).

Figure 45A:
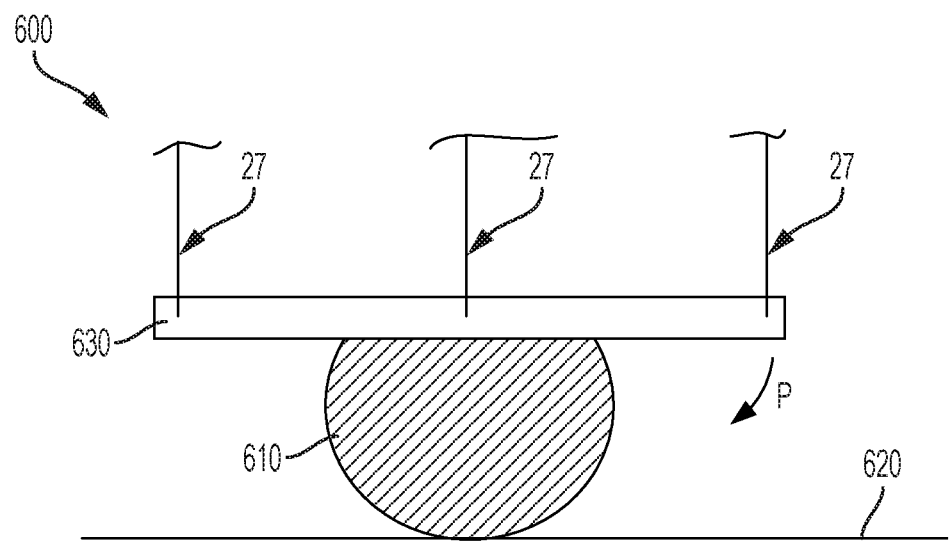
FIGS. 45A and 45B show a side view of a plate and attached deformable ball with attached pull wires for use in a steerable catheter assembly.
Figure 45B:
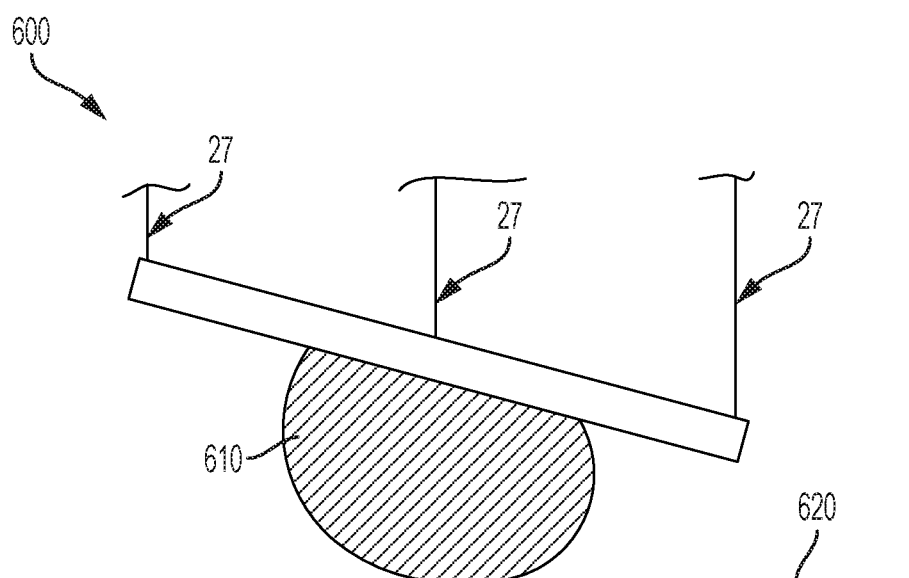

FIGS. 45A and 45B illustrate an embodiment of an assembly 600 that interfaces with a projection (not shown) to control tension on at least two pull wires 27. Assembly 600 is a plate 630 attached to a deformable ball 610 that is in contact with a surface 620. The surface 620 is part of or fixed to a housing of a control handle (not shown). The deformable ball 610 deforms in response to tilt of the plate 630, which in embodiments disclosed herein is accomplished by the axial or rotational movement of a projection (not shown), thus allowing the plate 630 to rotate and tilt multidirectionally. FIG. 45B shows the deformable ball 610 in a deformed configuration after the tilt of the plate 630 indicated by arrow P in FIG. 45A. At least two pull wires 27 are attached to the plate 630 on one axial side of the plate 630. Though pull wires 27 are shown attached on the opposite axial side of plate 630 as the side to which the deformable ball 610 is attached, the pull wires 27 may be attached to the plate 630 on the same axial side as deformable ball 610, depending on the orientation of surface 620 and the pull wires 27 within the control handle housing.

Further, as with the gimbal plate, ball-and-socket, and assembly 500 embodiments, the radius of the plate 630 can be increased to increase the maximum tension that can be applied to the pull wires 27 (and thus the maximum flex magnitude of an attached catheter).

Figure 46B:
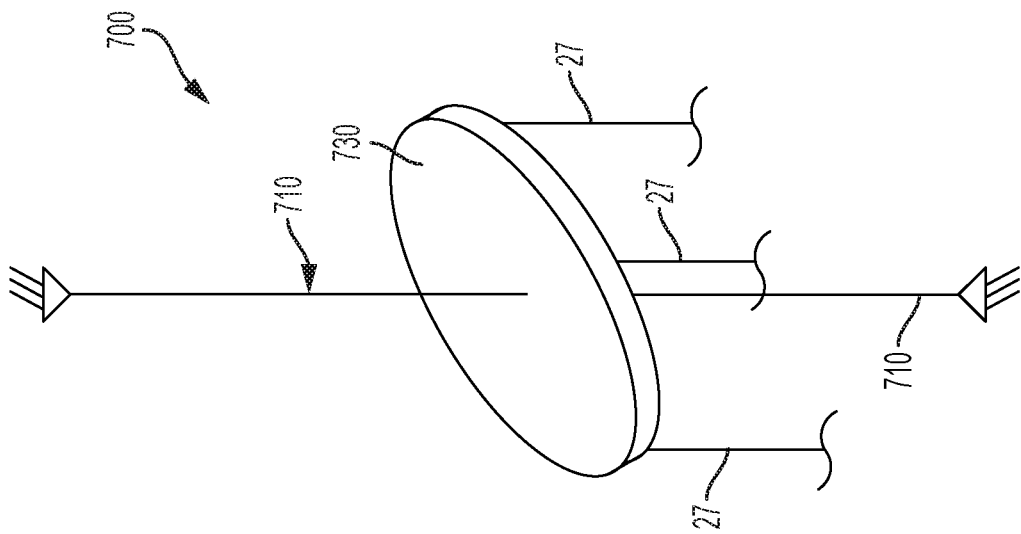
FIGS. 46A and 46B show a perspective view of a plate suspended from a control handle housing with attached pull wires for use in a steerable catheter assembly.
Figure 46A:
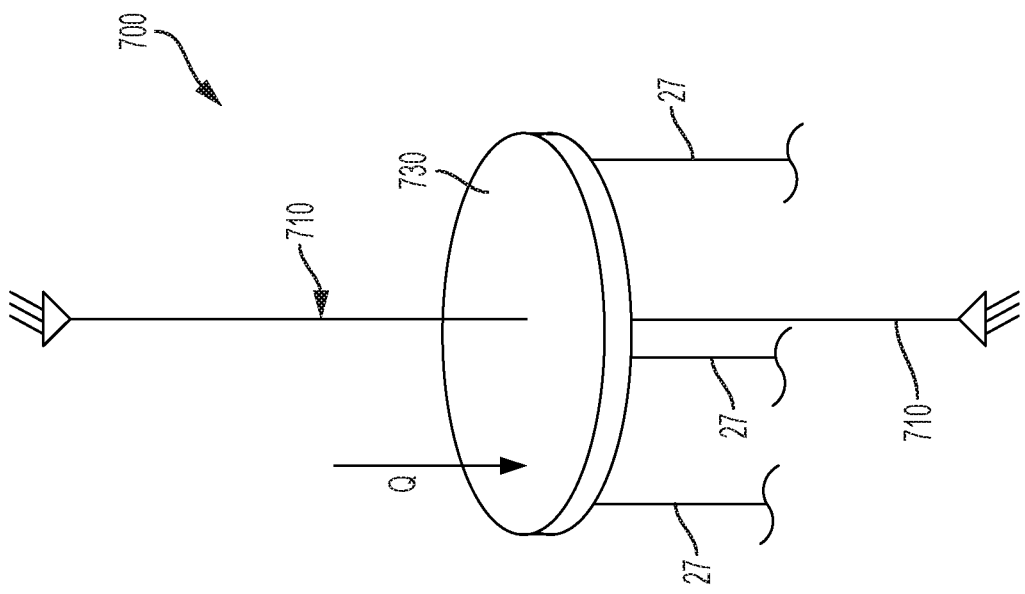
Figure 47:
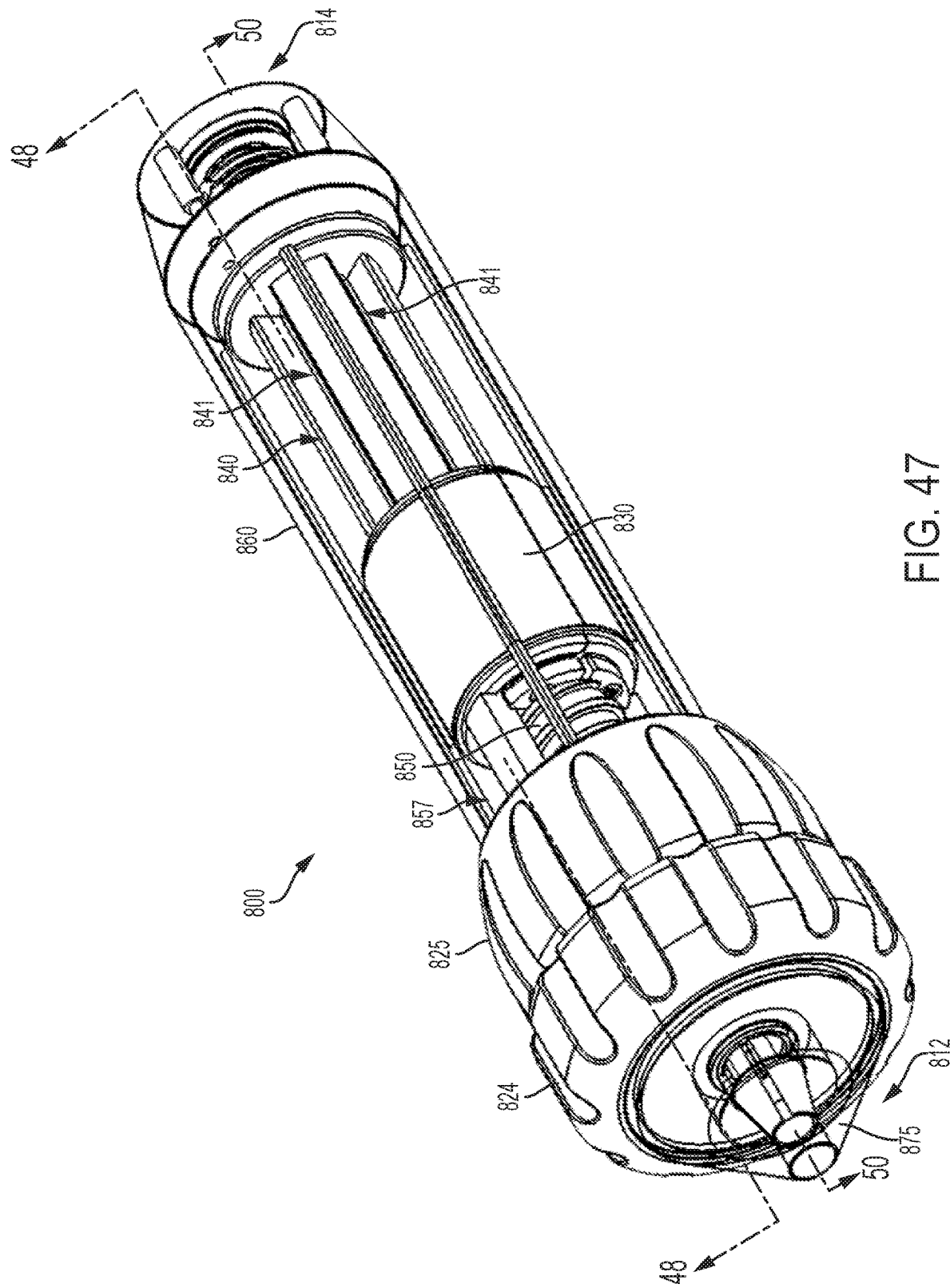
FIG. 47 shows a perspective view of an embodiment of a multi-direction control handle having a dual threaded nut, follower, and driver.

FIGS. 46A and 46B illustrate an embodiment of an assembly 700 that interfaces with a projection (not shown) to control tension on at least two pull wires 27. Assembly 700 is a plate 730 suspended from a housing of a control handle (not shown) by at least one suspension wire 710. At least one suspension wire 710 allows the plate 730 to tilt multidirectionally, which in embodiments disclosed herein is accomplished in response to the axial or rotational movement of a projection (not shown), thus applying a force to one axial side of the plate 730. FIG. 46B shows suspended plate 730 in a tilted position after the projection applies a force to plate 730 as indicated by arrow Q in FIG. 46A. At least two pull wires 27 are attached to plate 730 on one axial side of the plate 730. The pull wires 27 are attached on the axial side of plate 730 that is opposite the suspending wire 710. The projection, however, can apply a force on either axial side of plate 730 to control tension on the at least two pull wires 27. Further, as with the gimbal plate, ball-and-socket, assembly 500, and assembly 600 embodiments, the radius of the plate 730 can be increased to increase the maximum tension that can be applied to the pull wires 27 (and thus the maximum flex magnitude of an attached catheter).

FIGS. 47-53 show views of embodiments and components of a catheter control handle 800 that provides steerability for an attached catheter (not pictured in FIGS. 47-53). A distal end 812 of the handle 800 can be coupled to a catheter (see catheter 2 of system 5 in FIG. 43) or other elongated and steerable tubular or transluminal device for insertion into a patient, while a proximal end 814 may include luminal access for passage of other devices, pull wires, and/or fluids through the handle 800 and the attached catheter.

Figure 48:
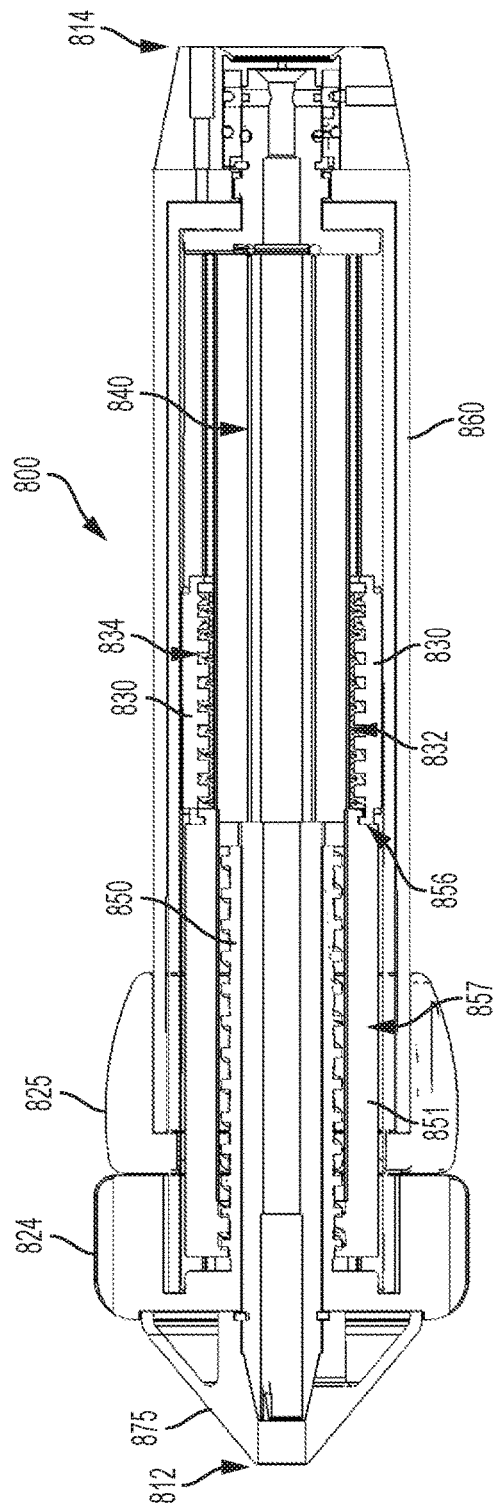
FIG. 48 shows a sectional view of the multi-direction control handle of FIG. 47 taken along the plane indicated by lines 48-48 in FIG. 47.
Figure 49:
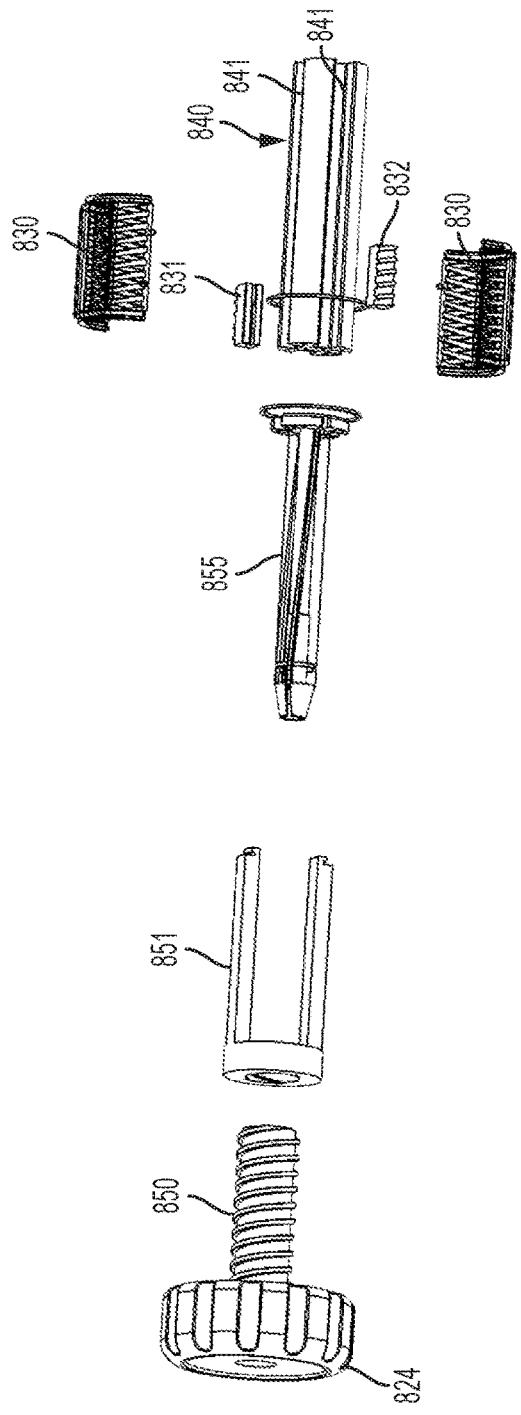
FIG. 49 shows exploded views of the driver and dual threaded nut and follower mechanisms of the control handle of FIG. 47.

With reference to FIGS. 48 and 49, the control handle 800 includes a drive nut 830, a first follower 831 and a second follower 832 respectively, and a driver 857 disposed inside of control handle 800. The followers 831, 832 are attached to pull wires (not shown). The driver 857 axially translates in response to adjustments of a drive knob or a flex knob 824 and causes axial motion of the drive nut 830. The axial motion of the drive nut 830 causes equal axial motion in the first and second followers 831, 832, in turn causing an equal adjustment in the tension of two pull wires (not shown). This adjustment in tension causes an adjustment in the magnitude of radial flex of the attached catheter (not shown).

The drive nut 830 rotates in response to adjustments of the flex knob 825. The rotation of the drive nut 830 causes the first and second followers 831, 832 to move in opposite axial directions. Rotating the steering knob 825 in one direction causes one follower to travel axially toward its attached pull wire and one follower to travel axially away from its attached pull wire, thereby creating greater tension in one pull wire and reducing tension in the other. This causes the attached catheter to flex in the direction of the tensed wire. Rotating steering knob 825 in the opposite direction causes the opposite effect on the axial motion of the followers 830, 831, thereby causing the attached catheter to flex in the direction of the other tensed wire. Thus, steering knob 825 controls direction of flex of an attached catheter. Embodiments of control handle 800 may further include cap 875 and housing 860.

In embodiments disclosed herein and as shown in FIGS. 48-49, the driver 857 is comprised of a threaded drive screw 850 and a threaded drive shaft 851. In the control handle 800, adjusting the drive knob 825 causes rotation of threaded drive screw 850, which is engaged with internal threads of the drive shaft 851. Rotation of the threaded drive screw 850 causes the drive shaft 851 to move axially. A coupling 856 is formed between the end of the drive shaft 851 and the end of the drive nut 830. As such, the axial movement of the drive shaft results in pushing or pulling of the dual threaded nut 830. Since the first and second followers 831 and 832 are in the dual threaded nut 830, the first and second followers are moved by an equal axial amount. In the embodiment shown in FIGS. 48 and 49, the drive coupling 856 couples drive shaft 851 and dual threaded nut 830 such that distal or proximal axial motion of drive shaft 851 causes the same motion in dual threaded nut 830.

In FIGS. 50-53, the steering mechanism of the control handle 800 comprises the dual threaded nut 830, a follower guide 840 with follower slots 841, and a nut rotator 861. The first and second followers 831, 832 reside in different follower slots 841 of the follower guide 840. The follower guide 840 is stationary with respect to housing 860 and the rotator 861. When steering knob 825 is adjusted, nut rotator 861 rotates the dual threaded nut 830 with respect to housing 860 (without axial motion of dual threaded nut 830 relative to housing 860).

Figure 53:
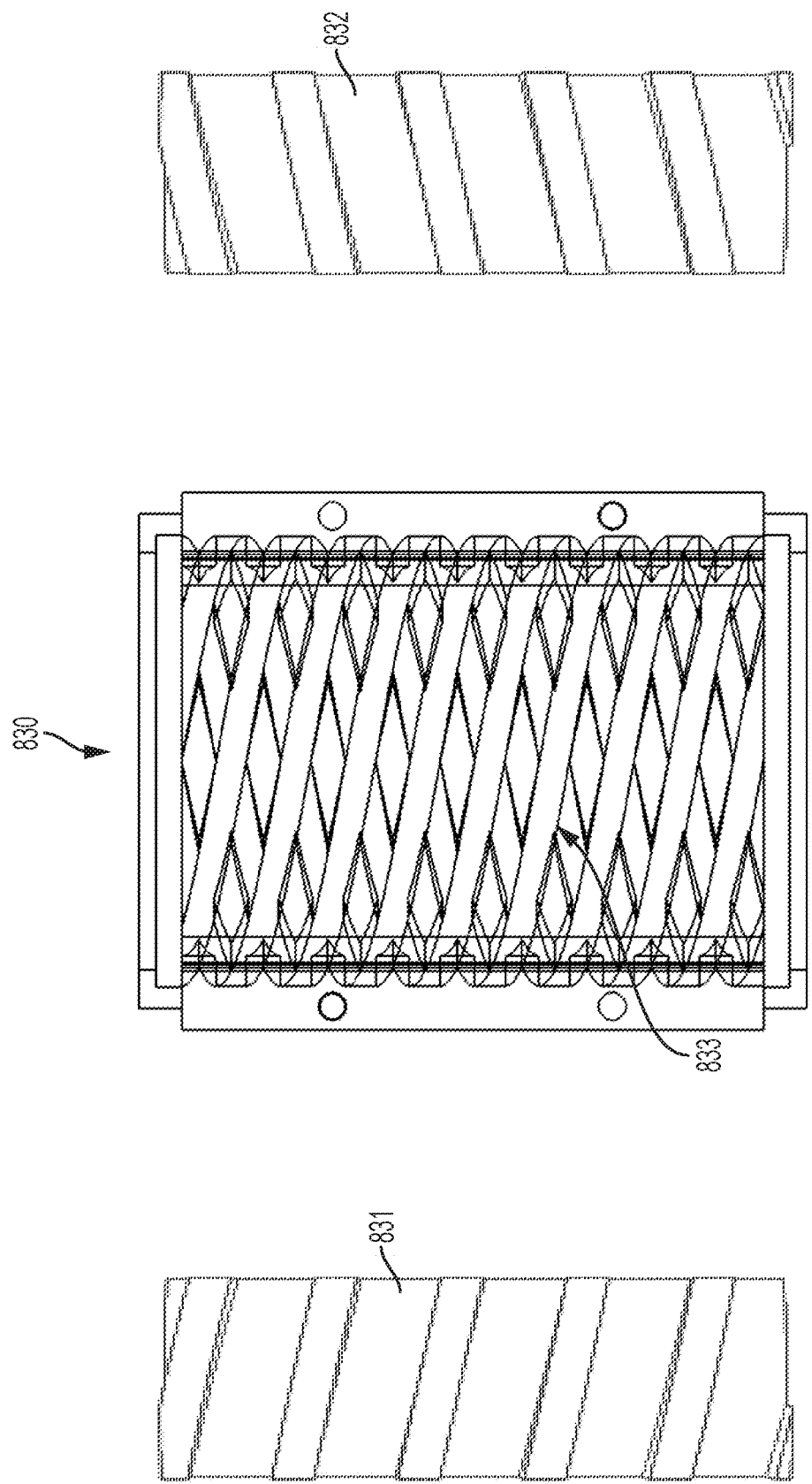
FIG. 53 shows an exploded view of an embodiment of a dual threaded nut and follower assembly.
Figure 54:
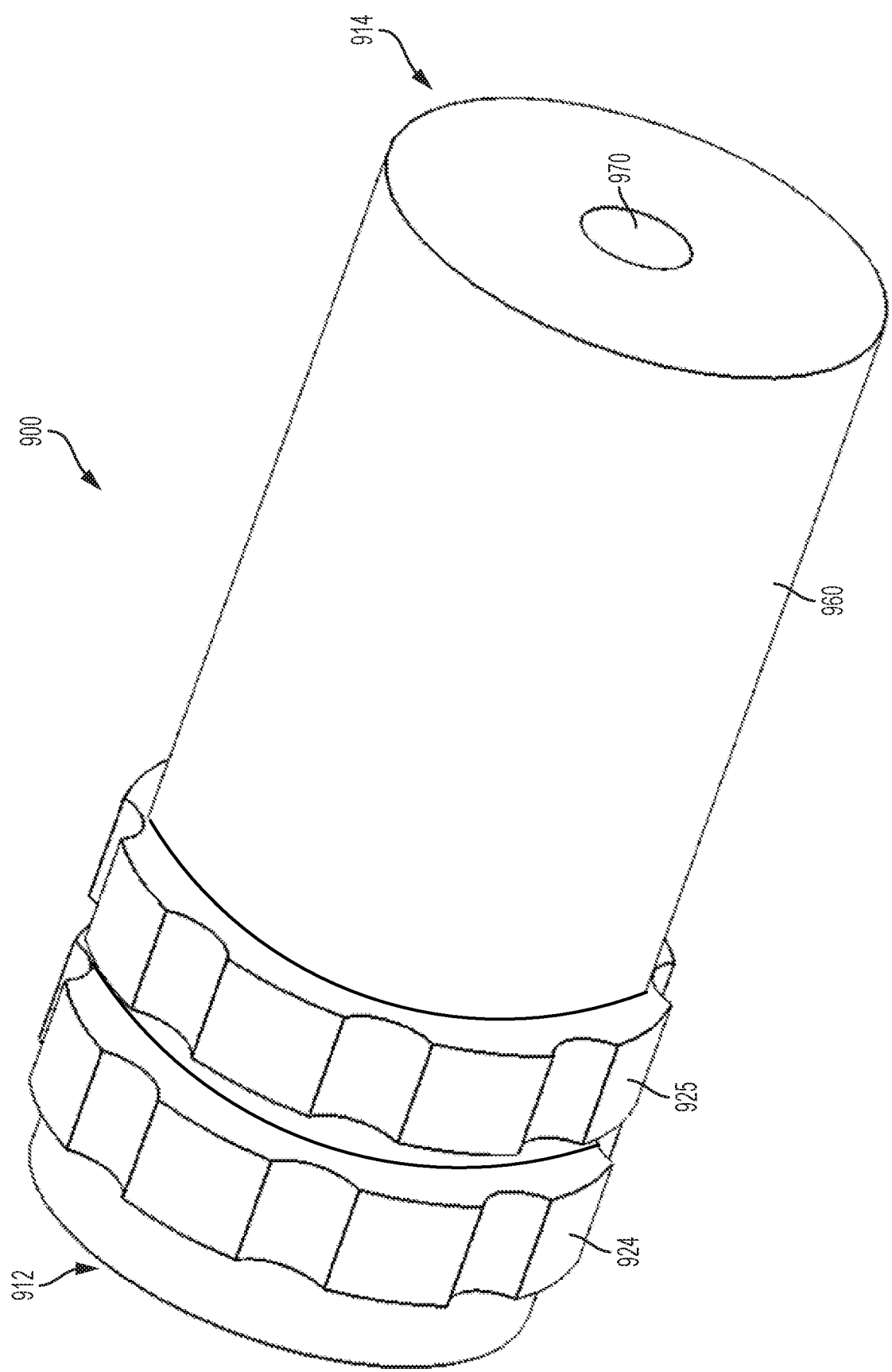
FIG. 54 shows a perspective view of an embodiment of a control handle with a planetary gear assembly.
Figure 55A:
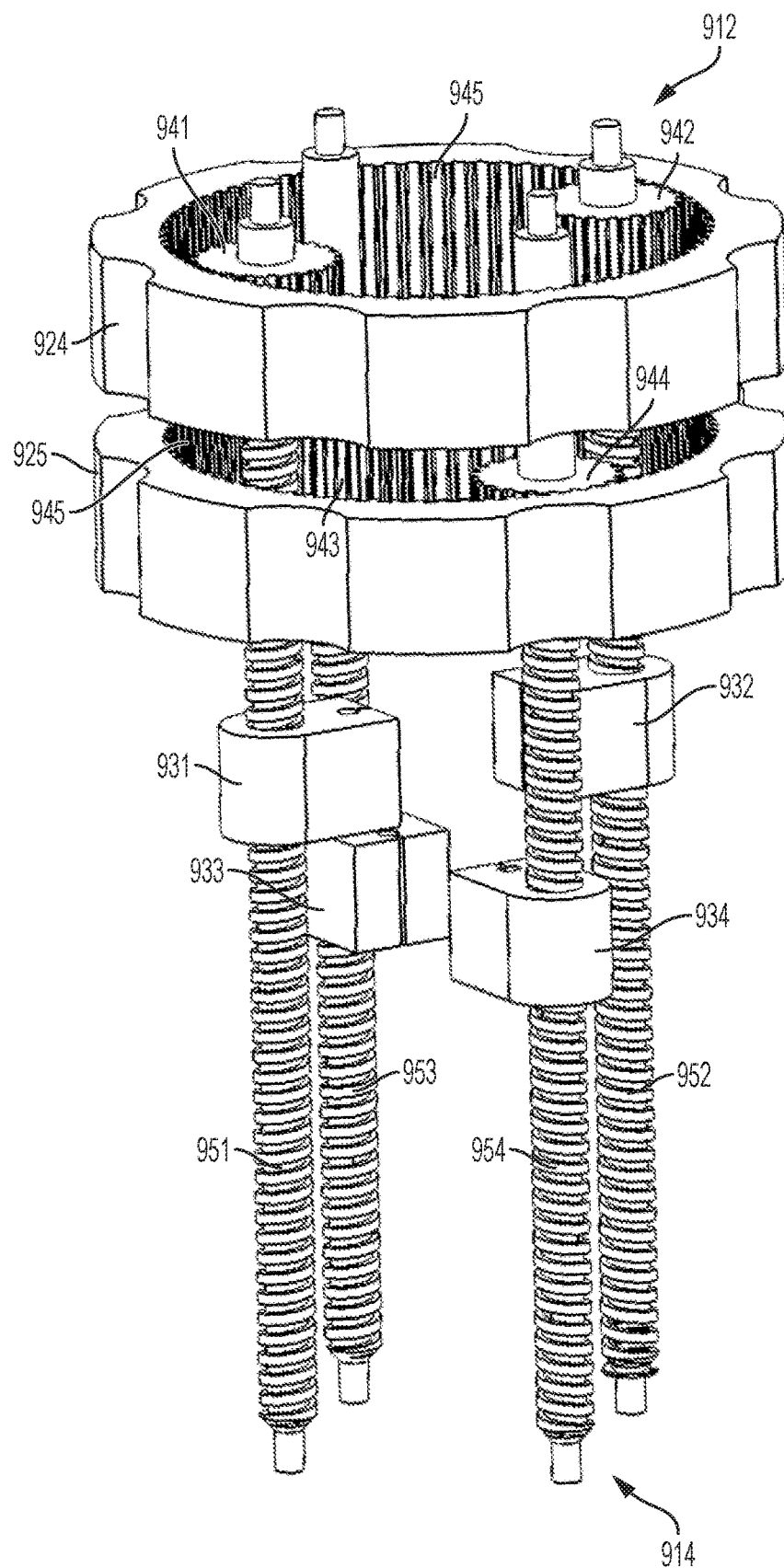
FIGS. 55A-55C show perspective views of the planetary gear assembly of the handle illustrated by FIG. 54.
Figure 55B:
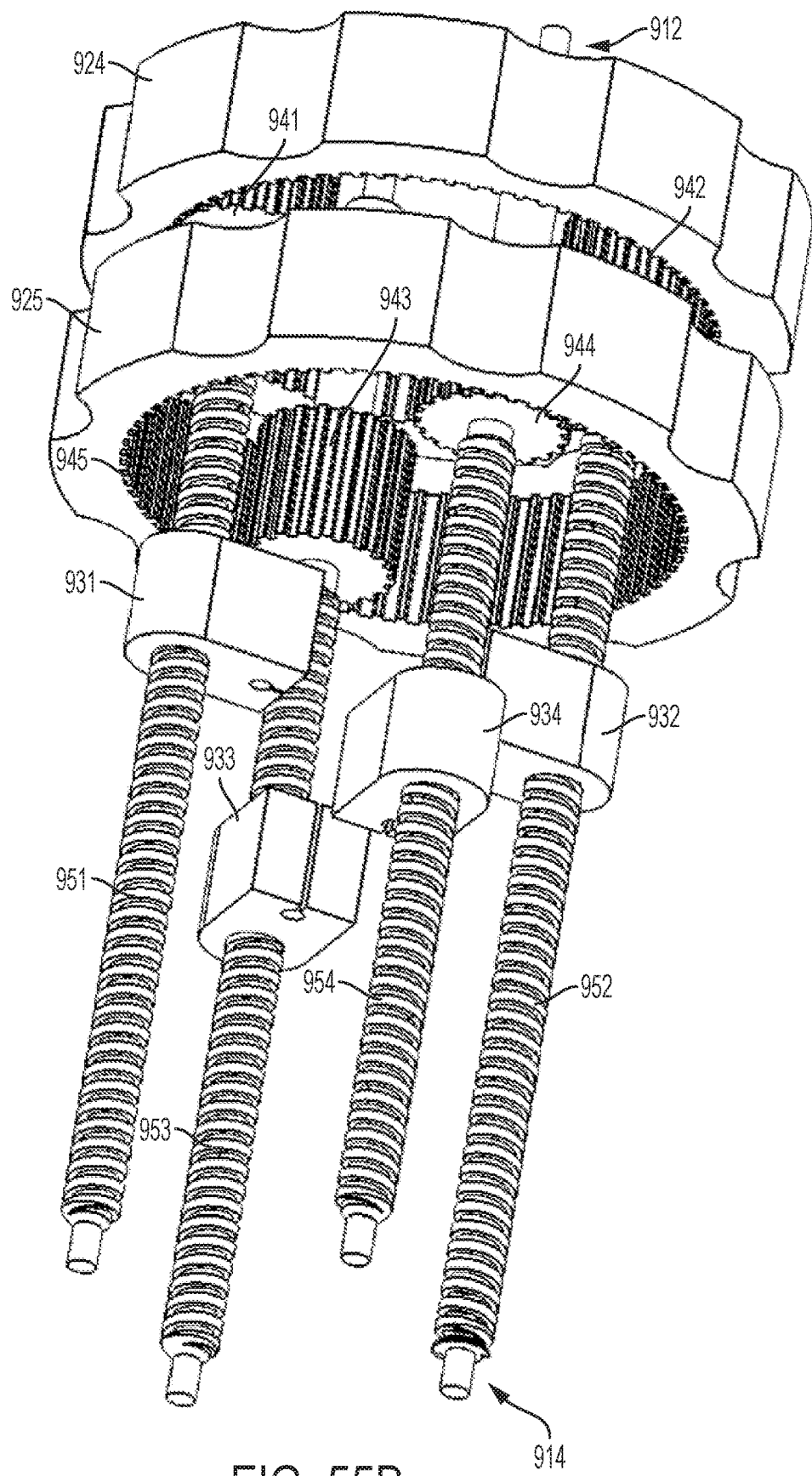
Figure 55C:
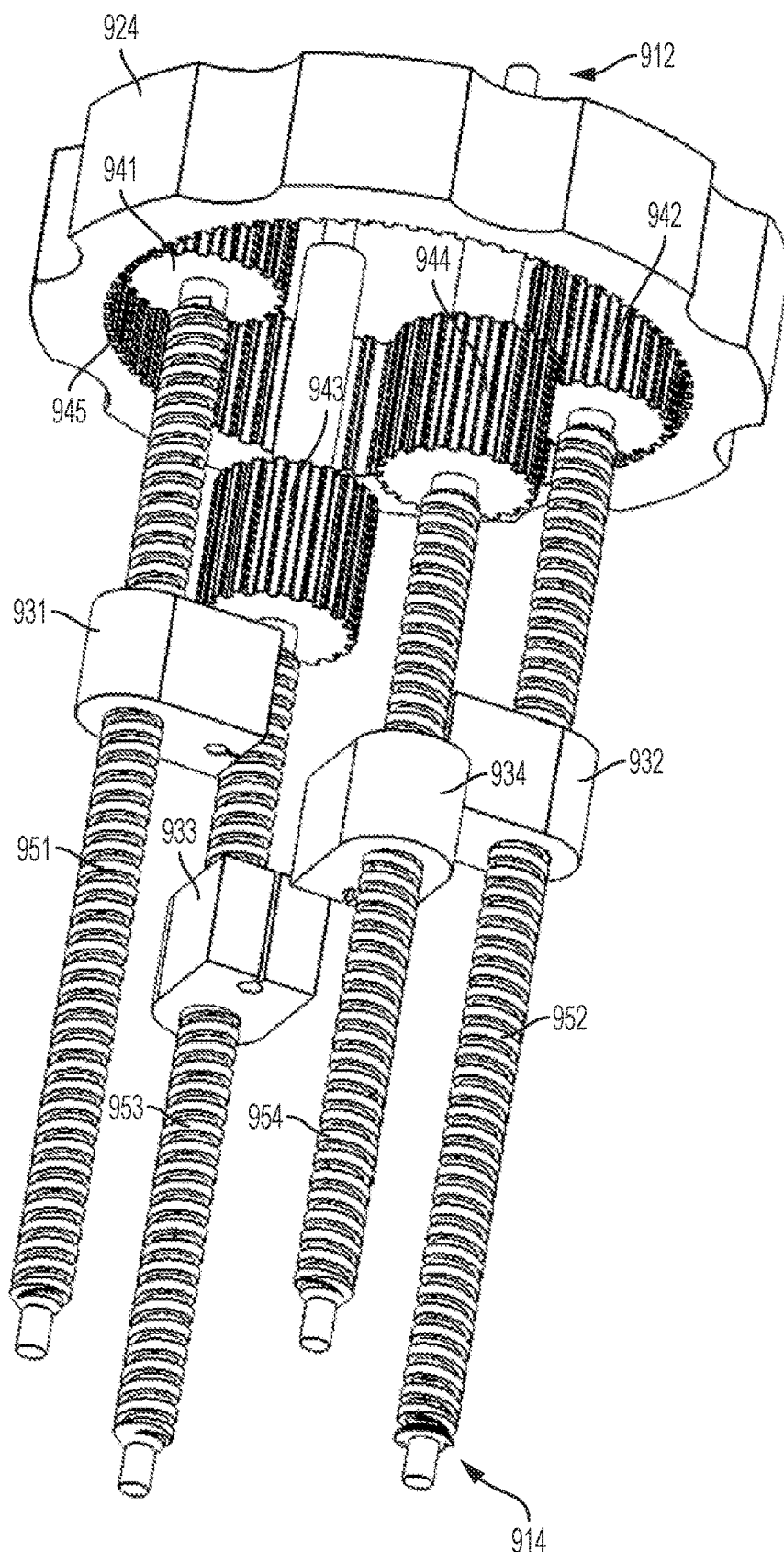
Figure 56A:
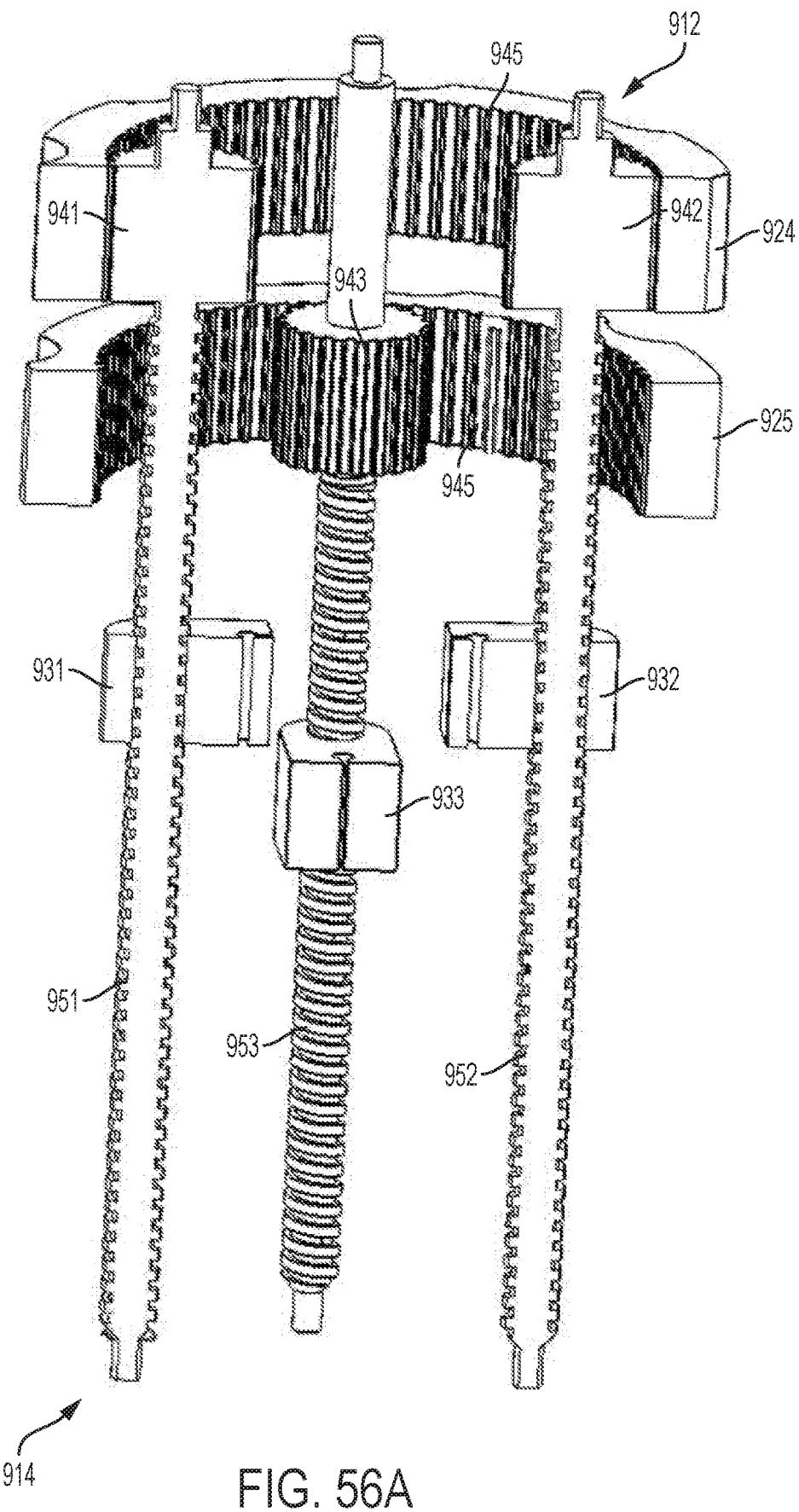
FIGS. 56A-56C show cut-away, perspective views of the planetary gear assembly of the handle illustrated by FIG. 54.
Figure 56B:
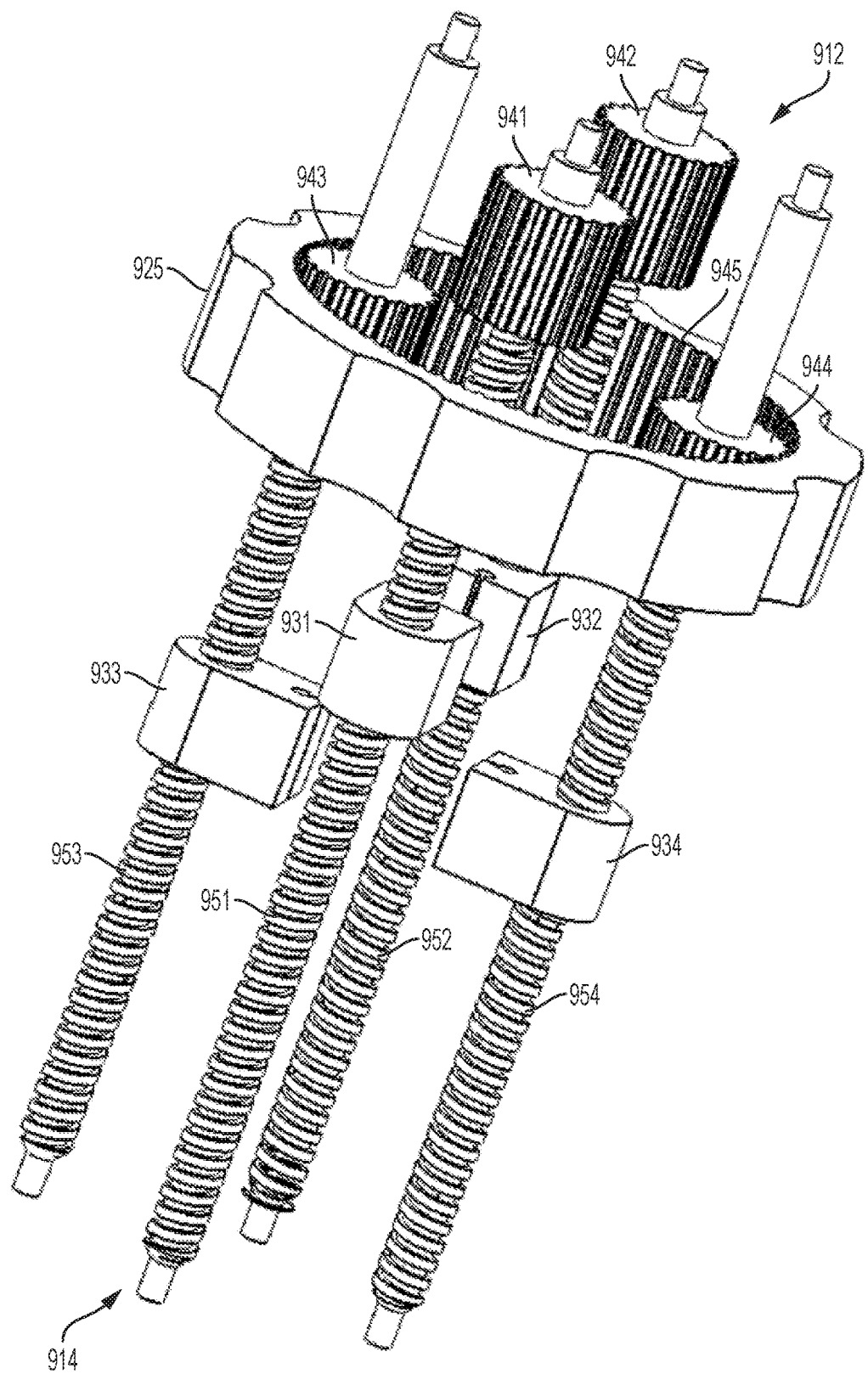
Figure 56C:
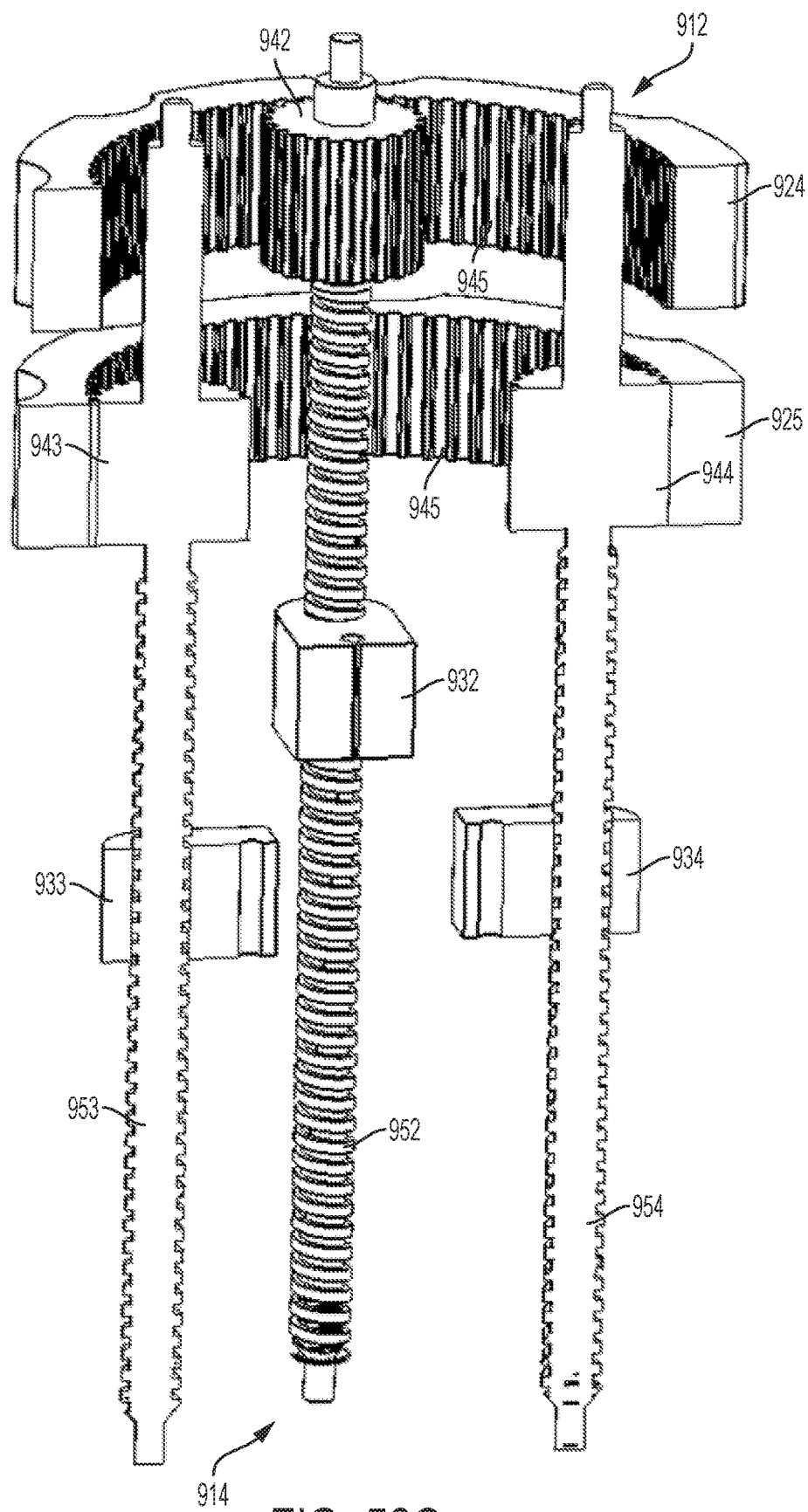
Figure 57:
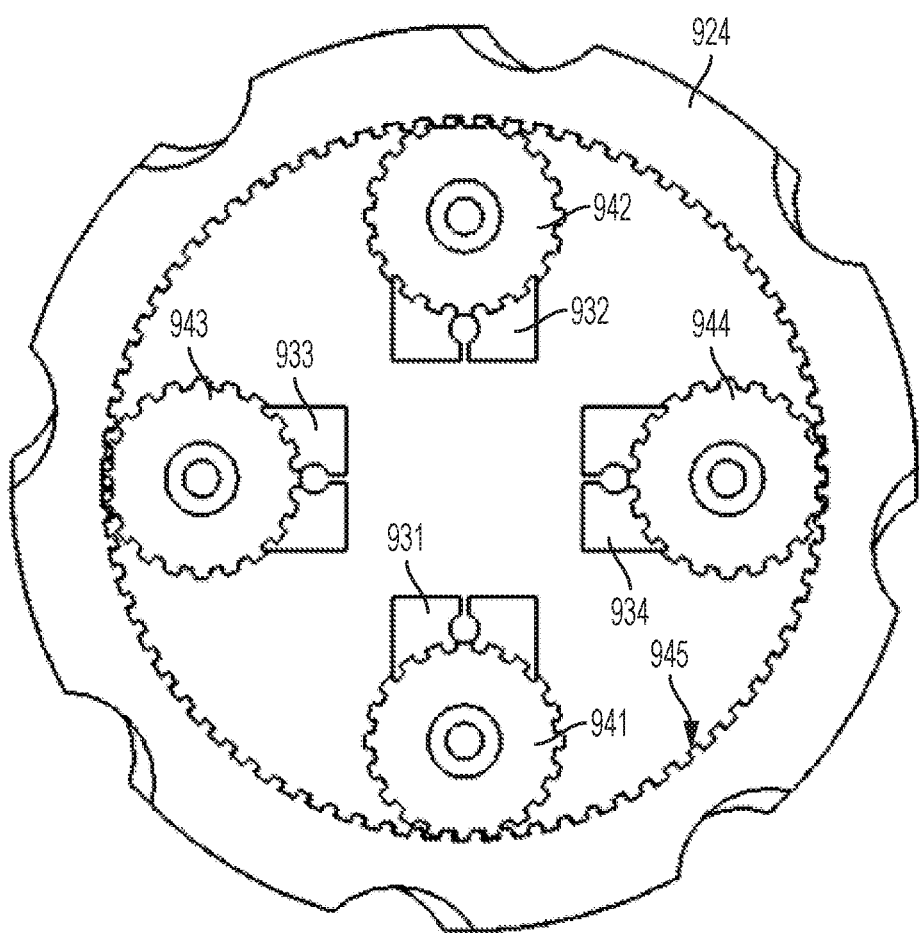
FIG. 57 shows a top-down, cut-away view of the planetary gear assembly of the handle illustrated by FIG. 54.

As shown in FIG. 53, dual threaded nut 830 is cut with internal, dual, left and right threads 833. First follower 831 has external, left-hand threads. The threads of first follower 831 engage the left-hand set of threads in dual threaded nut 830. Second follower 832 has external, right-hand threads. The threads of second follower 832 engage the right-hand set of threads in dual threaded nut 830. For the same turn of dual threaded nut 830 by the rotator 861, the first and second followers 831, 832 move in opposite axial directions in follower slots 841 with respect to housing 860 as a result of their opposite threading. Attached pull wires correspondingly tense or relax depending on the axial direction of movement of the followers 831 and 832. The pull wires (not shown) are routed through a pull wire guide 855 and to the proximal end of the handle 800.

FIGS. 54-57 are views of an exemplary embodiment of a catheter control handle 900 that provides steerability for an attached catheter 2 (not pictured in FIGS. 54-57). A distal end 914 of the handle 900 can be coupled to a catheter (see catheter 2 of system 5 in FIG. 43) or other elongated and steerable tubular or transluminal device for insertion into a patient. A luminal access 970 can extend from a proximal end 912 to the distal end 914 for passage of other devices, pull wires, and/or fluids through the handle 900 and the attached catheter.

The illustrated control handle 900 includes a first follower 931, a second follower 932, a third follower 933, and a fourth follower 934. A first driver 924 is coupled to the first and second followers 931 and 932, which are circumferentially oppositely disposed from one another. A second driver 925 is coupled to the third and fourth followers 933 and 934, which are also circumferentially oppositely disposed from one another and are positioned about 90° from the first and second followers 931, 932. Rotation of the first driver 924 moves the first and second followers 931 and 932 in opposite axial directions with respect to control handle 900. Rotation of the second driver 925 moves the third and fourth followers 933 and 934 in opposite axial directions with respect to control handle 900. Pull wires attached to followers that move proximally with respect to the housing 860 increase in tension and pull wires attached to followers that move distally relax. The attached catheter flexes in the direction of the tensed pull wires. Thus, control of magnitude and direction of flex is not independent for control handle 900. First and second drivers 924 and 925 may be rotatable drive rings with internal teeth 945.

As shown in section views with housing 960 removed in FIGS. 55A-57, control handle 900 can further comprise first, second, third, and fourth drive gears 941, 942, 943, and 944 respectively and first, second, third, and fourth drive screws 951, 952, 953, and 954 respectively. The drive screws are rotatably attached to the housing 960 and each drive gear is fixed to its corresponding drive screw such that rotation of a drive gear causes rotation of its corresponding drive screw without axial motion of the drive screw or drive gear with respect to the housing 960. In disclosed embodiments, first and second drive gears 941 and 942 engage internal teeth 945 of first driver 924, and third and fourth drive gears 943 and 944 engage internal teeth 945 of second driver 925. Further, first and third drive screws 951 and 953 are left-hand threaded, and second and fourth drive screws 952 and 954 are right-hand threaded. First and third followers 931 and 933 are set with internal left-hand threads and respectively engage the threads of first and third drive screws 951 and 953. Second and fourth followers 932 and 934 are set with internal right-hand threads and respectively engage the threads of second and fourth drive screws 952 and 954. Rotation of first driver 924 causes equal rotation of first and second drive gears 941 and 942 and thus of first and second drive screws 951 and 952. First follower 931 and second follower 932 move in opposite axial directions in response, because of their opposite threading. The attached catheter flexes in the direction of the follower that moves proximally and thus tenses its attached pull wire. Rotation of second driver 925 causes equal rotation of third and fourth drive gears 943 and 944 and thus of third and fourth drive screws 953 and 954. Third follower 933 and fourth follower 934 move in opposite axial directions in response, because of their opposite threading. The attached catheter flexes in the direction of the follower that moves proximally and thus tenses its attached pull wire.

It should be understood that the disclosed embodiments can be adapted to deliver and implant prosthetic devices in any of the native annuluses of the heart (e.g., the pulmonary, mitral, and tricuspid annuluses), and can be used with any of various approaches (e.g., retrograde, antegrade, transseptal, transventricular, transatrial, etc.). The disclosed embodiments can also be used to implant prostheses in other lumens of the body. Further, in addition to prosthetic valves, the delivery assembly embodiments described herein can be adapted to deliver and implant various other prosthetic devices such as stents and/or other prosthetic repair devices. In other embodiments, the disclosed devices can be used to perform various other transvascular surgical procedures other than implanting a prosthetic device.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the term "coupled" generally means physically, electrically, magnetically, and/or chemically coupled or linked and does not exclude the presence of intermediate elements between the coupled or associated items absent specific contrary language.

As used herein, the term "proximal" refers to a position, direction, or portion of a device that is closer to the user/operator of the device and further away from an end or destination of the device within a patient's body (e.g., the heart). As used herein, the term "distal" refers to a position, direction, or portion of a device that is further away from the user/operator of the device and closer to the end or destination of the device within a patient's body. Thus, for example, proximal motion of a catheter is motion of the catheter out of the body and/or toward the operator (e.g., retraction of the catheter out of the patient's body), while distal motion of the catheter is motion of the catheter away from the operator and further into the body (e.g., insertion of the catheter into the body toward the heart). The terms "longitudinal" and "axial" refer to an axis extending in the proximal and distal directions, unless otherwise expressly defined.

As used herein, the terms "integrally formed" and "unitary construction" refer to a one-piece construction that does not include any welds, fasteners, or other means for securing separately formed pieces of material to each other.

As used herein, operations that occur "simultaneously" or "concurrently" occur generally at the same time as one another, although delays in the occurrence of one operation relative to the other due to, for example, spacing, play or backlash between components in a mechanical linkage such as threads, gears, etc., are expressly within the scope of the above terms, absent specific contrary language.

In view of the many possible embodiments to which the principles of the disclosure may be applied, it should be recognized that the illustrated embodiments are only preferred examples and should not be taken as limiting the scope of the disclosure. Rather, the scope of the disclosed technology is at least as broad as the following claims. We therefore claim as our invention all that comes within the scope of these claims as well as their equivalents.

We claim:

1. A steerable catheter assembly comprising:
a catheter with first and second oppositely disposed pull wires and third and fourth oppositely disposed pull wires that flex the catheter;
a control handle coupled to the catheter, wherein the control handle has a longitudinal axis;
a first follower connected to the first pull wire;

a second follower connected to the second pull wire;
a first driver coupled to the control handle and coupled to the first and second followers;
wherein rotation of the first driver linearly moves the first and second followers in opposite directions along the longitudinal axis of the control handle;
a third follower connected to the third pull wire;
a fourth follower connected to the fourth pull wire;
a second driver coupled to the control handle and coupled to the third and fourth followers;
wherein rotation of the second driver linearly moves the third and fourth followers in opposite directions along the longitudinal axis of the control handle.

2. The steerable catheter assembly of claim 1, wherein the first driver comprises a first drive ring, a first drive screw coupled to the first drive ring, and a second drive screw coupled to the first drive ring.

3. The steerable catheter of claim 1, wherein the first driver comprises a first planetary gear that engages first and second drive screws, such that one adjustment of the first planetary gear turns the first and second drive screws, and the first and second followers move in opposite axial directions.

4. The steerable catheter assembly of claim 2, wherein the first follower is threaded and engages threads of the first drive screw and the second follower is threaded and engages threads of the second drive screw.

5. The steerable catheter of claim 2, wherein the first drive ring comprises internal gear teeth.

6. The steerable catheter of claim 2, wherein the first drive screw is left hand-threaded and the second drive screw is right hand-threaded.

7. The steerable catheter assembly of claim 2, wherein the second driver comprises a second drive ring, a third drive screw coupled to the second drive ring, and a fourth drive screw coupled to the second drive ring.

8. The steerable catheter of claim 5, wherein the first drive screw includes a first gear that engages the internal gear teeth and the second drive screw includes a second gear that engages the internal teeth.

9. The steerable catheter of claim 7, wherein the third follower is threaded and engages threads of the third drive screw and the fourth follower is threaded and engages threads of the fourth drive screw.

10. The steerable catheter of claim 7, wherein the second drive ring comprises internal gear teeth.

11. The steerable catheter of claim 7, wherein the third drive screw is left hand-threaded and the fourth drive screw is right hand-threaded.

12. The steerable catheter of claim 10, wherein the third drive screw includes a third gear that engages the internal gear teeth of the second drive ring and the fourth drive screw includes a fourth gear that engages the internal teeth of the second drive ring.

13. The steerable catheter of claim 3, wherein the second driver comprises a second planetary gear that engages third and fourth drive screws, such that one adjustment of the second planetary gear turns the third and fourth drive screws, and the third and fourth followers move in opposite axial directions.

14. A method of steering a catheter comprising:
rotating a first driver to move first and second followers in linearly opposite axial directions, wherein the first and second followers are connected to first and second catheter flex wires; and
rotating a second driver to move third and fourth followers in linearly opposite axial directions, wherein the third and fourth followers are connected to third and fourth catheter flex wires.

15. The method of claim 14, wherein the first and second followers are moved in opposite directions by first and second opposite handed screws that are rotated in the same direction.

16. The method of claim 15, wherein the third and fourth followers are moved in opposite directions by third and fourth opposite handed screws that are rotated in the same direction.

17. A steerable catheter assembly comprising:
a catheter with first and second oppositely disposed pull wires and third and fourth oppositely disposed pull wires that flex the catheter;
a control handle coupled to the catheter;
a first follower connected to the first pull wire;
a second follower connected to the second pull wire;
a first driver coupled to the control handle and coupled to the first and second followers, the first driver comprising:
a first drive ring comprising internal gear teeth;
a first drive screw coupled to the first drive ring; and
a second drive screw coupled to the first drive ring;
wherein the first drive screw includes a first gear that engages the internal gear teeth and the second drive screw includes a second gear that engages the internal teeth; and
wherein rotation of the first driver moves the first and second followers in opposite directions;
a third follower connected to the third pull wire;
a fourth follower connected to the fourth pull wire;
a second driver coupled to the control handle and coupled to the third and fourth followers;
wherein rotation of the second driver moves the third and fourth followers in opposite directions.

18. A steerable catheter assembly comprising:
a catheter with first and second oppositely disposed pull wires and third and fourth oppositely disposed pull wires that flex the catheter;
a control handle coupled to the catheter;
a first follower connected to the first pull wire;
a second follower connected to the second pull wire;
a first driver coupled to the control handle and coupled to the first and second followers;
wherein the first driver comprises a first planetary gear that engages first and second drive screws, such that one adjustment of the first planetary gear turns the first and second drive screws, and the first and second followers move in opposite axial directions;
a third follower connected to the third pull wire;
a fourth follower connected to the fourth pull wire;
a second driver coupled to the control handle and coupled to the third and fourth followers;
wherein rotation of the second driver moves the third and fourth followers in opposite directions.

19. The steerable catheter of claim 18, wherein the second driver comprises a second planetary gear that engages third and fourth drive screws, such that one adjustment of the second planetary gear turns the third and fourth drive screws, and the third and fourth followers move in opposite axial directions.

* * * * *